(12) United States Patent
Clark et al.

(10) Patent No.: US 8,354,422 B2
(45) Date of Patent: Jan. 15, 2013

(54) PYRIMIDINE INHIBITORS OF KINASE ACTIVITY

(75) Inventors: Richard F. Clark, Gurnee, IL (US); Randy L. Bell, Lindenhurst, IL (US); Nwe Y. Ba-maung, Niles, IL (US); Scott A. Erickson, Zion, IL (US); Steve D. Fidanze, Grayslake, IL (US); Robert A. Mantei, Franklin, WI (US); George S. Sheppard, Wilmette, IL (US); Bryan K. Sorensen, Antioch, IL (US); Gary T. Wang, Libertyville, IL (US); Jieyi Wang, Lake Bluff, IL (US)

(73) Assignee: Abbott Laboratories Inc., Abbott Park, IL (US)

( * ) Notice: Subject to any disclaimer, the term of this patent is extended or adjusted under 35 U.S.C. 154(b) by 59 days.

(21) Appl. No.: 12/788,008

(22) Filed: May 26, 2010

(65) Prior Publication Data

US 2010/0305126 A1 Dec. 2, 2010

Related U.S. Application Data

(60) Provisional application No. 61/181,561, filed on May 27, 2009.

(51) Int. Cl.
*C07D 403/14* (2006.01)
*C07D 413/14* (2006.01)
*A61K 31/5377* (2006.01)
*A61K 31/506* (2006.01)

(52) U.S. Cl. ......... 514/275; 514/248; 544/235; 544/333

(58) Field of Classification Search .................. 544/333, 544/235; 514/275, 248
See application file for complete search history.

(56) References Cited

FOREIGN PATENT DOCUMENTS

WO WO2005068452 A1 7/2005
WO WO2006074057 A2 7/2006

OTHER PUBLICATIONS

Wolff Manfred E. "Burger's Medicinal Chemistry, 5ed, Part 1" John Wiley & Sons, 1995, pp. 975-977.*
Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Banker, G.S. et al, "Modern Pharmaceutics, 3ed." Marcel Dekker, New York, 1996, pp. 451 and 596.*
Adams T. E., et al., "Structure and function of the type 1 insulin-like growth factor receptor", Cellular and Molecular Life Sciences, 2000, vol. 57 (7), pp. 1050-1093.
Alexia C., et al., "An evaluation of the role of insulin-like growth factors (IGF) and of type-I IGF receptor signalling in hepatocarcinogenesis and in the resistance of hepatocarcinoma cells against drug-induced apoptosis", Biochem Pharmacol, 2004, vol. 68 (6), pp. 1003-1015.
Arteaga C.L., et al., "Growth Inhibition of Human Breast Cancer Cells in Vitro with an Antibody Against The Type I Somatomedin Receptor," Cancer Research, 1989, vol. 49 (22), pp. 6237-6241.
Bateman J. M., et al., "Insulin/IGF Signalling in Neurogenesis," Cellular and Molecular Life Sciences, 2006, vol. 63 (15), pp. 1701-1705.
Benito M., et al., "IGF-I: A Mitogen also Involved in Differentiation Processes in Mammalian Cells," The International Journal of Biochemistry & Cell Biology, 1996, vol. 28 (5), pp. 499-510.
Berge S. M., et al., "Pharmaceutical Salts", J Pharmaceutical Sciences, 1977, vol. 66 (1), pp. 1-19.
Bergmann U., et al., "Insulin-like growth factor I overexpression in human pancreatic cancer: evidence for autocrine and paracrine roles", Cancer Research, 1995, vol. 55 (10), pp. 2007-2011.
Bohula E. A., et al., "Targeting the type 1 insulin-like growth factor receptor as anti-cancer treatment", Anti-cancer Drugs., 2003, vol. 14 (9), pp. 669-682.
Brady G., et al., "Serum levels of insulin-like growth factors (IGFs) and their binding proteins (IGFBPs), -1, -2, -3, in oral cancer", International Journal of Oral and Maxillofacial Surgery, 2007, vol. 36 (3), pp. 259-262.
Brown Guy C., "Control of respiration and ATP synthesis in mammalian mitochondria and cells", Biochemical, 1992, vol. 248, pp. 1-13.
Bruning Jens C., et al., "A Muscle-Specific Insulin Receptor Knockout Exhibits Features of the Metabolic Syndrome of NIDDM without Altering Glucose Tolerance", Molecular Cell, 1998, vol. 2 (5), pp. 559-569.
Burfeind P., et al., "Antisense RNA to the type I insulin-like growth factor receptor suppresses tumor growth and prevents invasion by rat prostate cancer cells in vivo", The Proceedings of the National Academy of Sciences of the United States of America, 1996, vol. 93 (14), pp. 7263-7268.

(Continued)

*Primary Examiner* — Kahsay T Habte
(74) *Attorney, Agent, or Firm* — Glen J. Gesicki

(57) ABSTRACT

The present invention relates to compounds of formula (I) or pharmaceutical acceptable salts or solvates thereof,

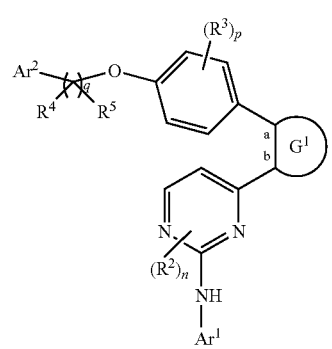

(I)

wherein $G^1$, $R^2$, $R^3$, $R^4$, $R^5$, n, p, q, $Ar^1$, and $Ar^2$ are defined in the description. The present invention relates also to methods of making said compounds, and compositions comprising said compounds which are useful for inhibiting kinases such as IGF-1R.

18 Claims, No Drawings

OTHER PUBLICATIONS

Coppola D., et al., "A Functional Insulin-Like Growth Factor I Receptor is Required for the Mitogenic and Transforming Activities of the Epidermal Growth Factor Receptor," Molecular and Cellular Biology, 1994, vol. 14 (7), pp. 4588-4595.

Cross L.C., et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.

Dandekar Ajai A., et al., "Comparison of the Signaling Abilities of the Cytoplasmic Domains of the Insulin Receptor and the Insulin Receptor-Related Receptor in 3T3-L1 Adipocytes", Endocrinology, 1998, vol. 139 (8), pp. 3578-3584.

Deangelis T., et al., "Insulin-Like Growth Factor I Receptor is Required for the Mitogenic and Transforming Activities of the Platelet-Derived Growth Factor Receptor," Journal of Cellular Physiology, 1995, vol. 164 (1), pp. 214-221.

Del Valle L., et al., "nsulin-like growth factor I receptor activity in human medulloblastomas", Clinical Cancer Research, 2002, vol. 8 (6), pp. 1822-1830.

Djavan B., et al., "Insulin-like growth factors and prostate cancer", World Journal of Urology, 2001, vol. 19 (4), pp. 225-233.

Durai R., et al., "The role of the insulin-like growth factor system in colorectal cancer: review of current knowledge", International Journal Colorectal Diseases., 2005, vol. 20 (3), pp. 203-220.

Greene T., et al., "Protective Groups in Organic Synthesis," Protecting Groups in Organic Synthesis, 1999, Third Edition, Table of Contents.

Guo Y S., et al., "Characterization of insulinlike growth factor I receptors in human colon cancer", Gastroenterology, 1992, vol. 102 (4 pt 1), pp. 1101-1108.

Harrington E. A., et al., "C-Myc-Induced Apoptosis in Fibroblasts is Inhibited by Specific Cytokines," The EMBO Journal, 1994, vol. 13 (14), pp. 3286-3295.

Jiang Y., et al., "A high expression level of insulin-like growth factor I receptor is associated with increased expression of transcription factor Sp1 and regional lymph node metastasis of human gastric cancer", 2004, vol. 21 (8), pp. 755-764.

Jiang Y., et al., "Induction of Tumor Suppression and Glandular Differentiation of A549 Lung Carcinoma Cells by Dominant-Negative IGF-I Receptor," Oncogene, 1999, vol. 18 (14), pp. 6071-6077.

Kaleko M., et al., "Overexpression of the Human Insulinlike Growth Factor I Receptor Promotes Ligand-Dependent Neoplastic Transformation," Molecular and Cellular Biology, 1990, vol. 10 (2), pp. 464-473.

Kellerer M., et al., "Insulin- and insulin-like growth-factor-I receptor tyrosine-kinase activites in human renal carcinoma", 1995, vol. 62 (5), pp. 501-507.

Kurmasheva R.T., et al., "IGF-I Mediated Survival Pathways in Normal and Malignant Cells," Biochimica et Biophysica Acta, 2006, vol. 1766, pp. 1-22.

Leroith D., et al., "The Insulin-Like Growth Factor System and Cancer," Cancer Letters, 2003, vol. 195, pp. 127-137.

Li, et al., "Two New Monoclonal Antibodies against the ? Subunit of the Human Insulin-Like Growth Factor-I Receptor," Biochemical and Biophysical Research Communications, 1993, vol. 196 (1), pp. 92-98.

Li Wanqing, et al., "Role of the Activation Loop Tyrosines in Regulation of the Insulin-like Growth Factor I Receptor-tyrosine Kinase", The Journal of Biological Chemistry, 2006, vol. 281 (33), pp. 23785-23791.

Mathis G.,, "HTRF(R) Technology", J Biomol Screen, 1999, 4 (6), 309-314.

Morrione A., et al., "Failure of the Bovine Papillomavirus to Transform Mouse Embryo Fibroblasts with a Targeted Disruption of the Insulin-Like Growth Factor I Receptor Genes," Journal of Virology, 1995, vol. 69 (9), pp. 5300-5303.

Neuvians T P., et al., "Differential expression of IGF components and insulin receptor isoforms in human seminoma versus normal testicular tissue", 2005, vol. 7 (5), pp. 446-456.

O'Brien M F., et al., "Insulin-like growth factor I and prostate cancer", Urology, 2001, vol. 58 (1), pp. 1-7.

Pollak M N., et al., "Insulin and insulin-like growth factor signalling in neoplasia", 2008, vol. 8 (12), pp. 915-928.

Pollak Michael N., et al., "Insulin-Like Growth Factors and Neoplasia", Nature Reviews Cancer, 2004, vol. 4, pp. 505-518.

Prescott et al., "Lipid Vesicles as Carriers for Introducing Biologically Active Materials into Cells," Methods in Cell Biology, 1976, Academic Press, vol. 14 (33) pp. 33-71.

Qi H., et al., "Expression of type 1 insulin-like growth factor receptor in marrow nucleated cells in malignant hematological disorders: correlation with apoptosis," 2006, vol. 85 (2), pp. 95-101.

Samani A.A., et al., "The Role of the IGF System in Cancer Growth and Metastasis: Overview and Recent Insights," Endocrine Reviews, 2007, vol. 28 (1), pp. 20-47.

Sciacca Laura, et al., "In IGF-I receptor-de®cient leiomyosarcoma cells autocrine IGF-II induces cell invasion and protection from apoptosis via the insulin receptor isoform A", Oncogene, 2002, vol. 21, pp. 8240-8250.

Scotlandi K., et al., "Blockage of Insulin-like Growth Factor-I Receptor Inhibits the Growth of Ewing's Sarcoma in Athymic Mice," Cancer Research, 1998, vol. 58, pp. 4127-4131.

Sell C., et al., "Effect of a Null Mutation of the Insulin-Like Growth Factor I Receptor Gene on Growth and Transformation of Mouse Embryo Fibroblasts," Molecular and Cellular Biology, 1994, vol. 14 (6), pp. 3604-3612.

Sell C., et al., "Simian Virus 40 Large Tumor Antigen is Unable to Transform Mouse Embryonic Fibroblasts Lacking Type 1 Insulin-Like Growth Factor Receptor," Proceedings of the National Academy of Sciences, 1993, vol. 90, pp. 11217-11221.

Sohda M., et al., "The role of insulin-like growth factor 1 and insulin-like growth factor binding protein 3 in human esophageal cancer", Anticancer Res., 2004, vol. 24 (5A), pp. 3029-3034.

Surmacz E., et al., "Function of the IGF-I Receptor in Breast Cancer," Journal of Mammary Gland Biology and Neoplasia, 2000, vol. 5 (1), pp. 95-105.

Trent J C., et al., "Early effects of imatinib mesylate on the expression of insulin-like growth factor binding protein-3 and positron emission tomography in patients with gastrointestinal stromal tumor", Cancer, 2006, vol. 107 (8), pp. 1898-1908.

Trojan J., et al., "Loss of tumorigenicity of rat glioblastoma directed by episome-based antisense cDNA transcription of insulin-like growth factor I", Proc Natl Acad Sci, 1992, vol. 89 (11), pp. 4874-4878.

Van Nimwegen M. J. et al., "Focal Adhesion Kinase: A Potential Target in Cancer Therapy," Biochemical Pharmacology, 2007, vol. 73, pp. 597-609.

Vella V., et al., "A novel autocrine loop involving IGF-II and the insulin receptor isoform-A stimulates growth of thyroid cancer", J Clin Endocrinol Metab., 2002, vol. 87 (1), pp. 245-254.

Vella V., et al., "The IGF system in thyroid cancer: new concepts", Mol Pathol., 2001, vol. 54 (3), pp. 121-124.

Walenkamp M.J.E., et al., "Genetic Disorders in the Growth Hormone—Insulin-Like Growth Factor-I Axis," Hormone Research, 2006, vol. 66, pp. 221-230.

Wu X., et al., "Serum levels of insulin growth factor (IGF-I) and IGF-binding protein predict risk of second primary tumors in patients with head and neck cancer", Clinical Cancer Research, 2004, vol. 10 (12 pt 1), pp. 3988-3995.

Yeh A H., et al., "Human melanoma cells expressing V600E B-RAF are susceptible to IGF1R targeting by small interfering RNAs", Oncogene, 2006, vol. 25 (50), pp. 6574-6581.

Zhao H., et al., "Plasma levels of insulin-like growth factor-1 and binding protein-3, and their association with bladder cancer risk", The Journal of urology, 2003, vol. 169 (2), pp. 714-717.

Zumkeller W., et al., "Insulin-like growth factor system in neuroblastoma tumorigenesis and apoptosis: potential diagnostic and therapeutic perspectives", Horm Metab Res., 1999, vol. 31 (2-3), pp. 138-141.

Zumkeller W., et al., "The IGF/IGFBP system in CNS malignancy", Mol Pathol., 2001, vol. 54 (4), pp. 227-229.

Zumkeller W., et al., "The insulin-like growth factor system in hematopoietic cells", Leuk Lymphoma., 2002, vol. 43 (3), pp. 487-491.

* cited by examiner

PYRIMIDINE INHIBITORS OF KINASE ACTIVITY

This application claims priority to U.S. Provisional Patent Application Ser. No. 61/181,561, which was filed on May 27, 2009 and is incorporated herein by reference.

TECHNICAL FIELD

Provided herein are compounds that inhibit protein kinases such as IGF-1R, compositions containing the compounds, and methods of treating diseases using the compounds.

BACKGROUND

Receptor tyrosine kinases (RTKs) have been implicated in cellular signaling pathways that control various cellular functions, including cell division, growth, metabolism, differentiation and survival, through reversible phosphorylation of the hydroxyl groups of tyrosine residues in proteins. Extracellular signals are transduced via activation of the cell surface receptors, with amplification and propagation using a complex choreography of cascades of protein phosphorylation and protein dephosphorylation events to avoid uncontrolled signaling. These signaling pathways are highly regulated, often by complex and intermeshed kinase pathways where each kinase may itself be regulated by one or more other kinases and protein phosphatases. The biological importance of these finely tuned systems is such that a variety of cell proliferative disorders have been linked to defects in one or more of the various cell signaling pathways mediated by tyrosine or serine/threonine kinases.

Receptor tyrosine kinases (RTKs) catalyze phosphorylation of certain tyrosyl amino acid residues in various proteins, including themselves, which govern cell growth, proliferation and differentiation. Insulin-like growth factor-1 receptor (IGF-1R) is a transmembrane tyrosine kinase ubiquitous among fetal and post-natal cell types. The IGF signaling axis is made up of multiple ligands (IGF-1, IGF-2 and Insulin), at least six high affinity ligand binding proteins and proteases, multiple receptors (IGF-1R & IGF-2R, IR and IRR), and many other down stream signaling proteins (Pollak, M N et al., Nature Reviews Cancer (2004) 4(7):505-518). The structure and function of the IGF-1R has been reviewed by Adams et al., Cell. Mol. Life Sci. (2000) 57:1050-1093 and Benito, M et al., Int J Biochem Cell Biol (1996) 28(5):499-510. The receptor is activated by the ligands IGF-1 and IGF-2, which are mitogenic proteins that signal through the IGF-1R and IR in an endocrine, paracrine or autocrine manner. Activation of the IGF-1 receptor tyrosine kinase elicits cellular responses which include cellular proliferation and protection of cells from apoptosis. (Id.) Over expression of IGF-1R leads to malignant transformation of cultured cells, while down regulation can reverse the transformed phenotype of tumor cells and potentially render them susceptible to apoptosis. (Id.) There are two splice variants of the IR gene, the IR-β isoform which regulates glucose uptake and is expressed in liver, muscle and adipose tissue, and the exon 11 variant human insulin receptor isoform A (IR-A) binds IGF-2 with high affinity and promotes proliferation and protection from apoptosis (Sciacca L. Oncogene (2002) 21(54):8240-8250). IR-A is predominantly expressed in fetal tissue and malignancies and at this receptor, IGF-2 is more potent than insulin in stimulating cancer cell migration. (Sciacca, Oncogene (2002) supra). Insulin receptor-related receptor tyrosine kinase (IRR) has 79% homology with the kinase domain of IR and is expressed only in a few limited cell types (Dandekar, A A et al., Endocrinology (1998) 139(8):3578-3584).

IGF-1R is a hetero-tetrameric, transmembrane, cell surface receptor tyrosine kinase. (Benito, Int J Biochem Cell Biol (1996)) An IGF-1 binding domain is part of the extracellular alpha-chain of IGF-1R, whereas the intracellular beta-chain contains the tyrosine kinase domain. Three tyrosine residues represent autophosphorylation sites, specifically $Tyr^{1131}$, $Tyr^{1135}$, and $Tyr^{1136}$ within the activation loop of the IGF-1R beta catalytic domain (Li, W et al., J. Biol. Chem. (2006) 281(33):23785-23791). Phosphorylation of all three is required for full receptor activation, and precedes phosphorylation of juxtamembrane tyrosines and carboxy terminus serines. The insulin receptor has three similar autophosphorylation sites on the activation loop and juxtamembrane region. Activation and autophoshorylation results in the recruitment of multiple docking proteins and the generation of intracellular signaling (Benito, Int J Biochem Cell Biol (1996)). Once activated, IGF-1R and IR can phosphorylate or interact directly with a number of intracellular protein substrates, including IRS-1, IRS-2, Grb2, Grb10, Grb14, Shc, SOC, 14.3.3, FAK, or indirectly with other proteins like PI3K and MAPK (Benito, M et al. Int J Biochem Cell Biol (1996) 28(5):499-510) (Brown, G C et al., Biochem. J (1992) 284: 1-13; Bruning, J C et al., Mol. Cell (1998) 2(5):559-569). Focal adhesion kinase (FAK) is of particular interest because of its role as a regulator of cell survival, proliferation, migration and invasion. FAK is activated by growth factor receptors such as IGF-1R, by binding through its N-terminal domain and autophosphorylation at $Tyr^{397}$. Activated or over expressed FAK is common in a wide variety of cancers, and may play a role in human carcinogenesis (van Nimwegen, M J et al., Biochem. Pharmacol. (2007) 73(5):597-609).

In addition to its role in cancers, the IGF receptor plays important and diverse roles in growth and development (Benito, M et al. Int J Biochem Cell Biol (1996) 28(5):499-510). IGF-1R has been implicated in several metabolic, and immunological diseases (Walenkamp, M J et al., Horm. Res. (2006) 66(5):221-230; Kurmasheva, R. T et al., Biochim. Biophys. Acta—Rev on Cancer (2006) 1766(1):1-22; Bateman, J M et al., Cell. Mol. Life Sci. (2006) 63(15):1701-1705, LeRoith, D, et al., Can. Lett. (2003) 195:127-137 and Samani A, et al., Endocrine Reviews 28(1):20-47.)

The role of the IGF/IGF-1R signaling system in cancer has been thoroughly examined over the last 15 years. In particular, the implication of IGF-1R in human cancer stems from its roles in stimulating mitogenesis, mobility and metastasis and in protecting against apoptosis. (Kurmasheva, Biochim. Biophys. Acta (2006).) Interest has grown with the understanding that in addition to its antiapoptotic and mitogenic roles, IGF/IGF-1R signaling seems to be necessary for the establishment and continuation of a transformed phenotype. It has been well established that constitutive activation or over expression, often results in non-adherent cell growth, even under serum depleted conditions in vitro, and is associated with the formation of tumors in nude mice. (Kaleko M et al, Mol Cell Biol. (1990) 10(2): 464-473). Perhaps even more importantly, it has been firmly established that cells, in which the gene encoding for IGF-1R has been deactivated, are totally resistant to transformation by agents which are normally capable of immortalizing normal cells, such as over expression of PDGFR or EGFR, the T antigen of the SV40 virus, the ES protein of bovine papilloma virus, and activated ras. (DeAngelis T et al., Cell. Physiol. (1995) 1640:214-221; Coppola D et al., Mol. Cell. Biol. (1994) 14(7):4588-4595; Morrione A J, Virol. 1995 695300-5303; Sell C et al., Mol. Cell. Biol. (1994) 14(6):3604-3612; Sell C et al., Proc. Natl. Acad. Sci.

USA (1993) 90(23):11217-11221). Thus, IGF-1R has been identified as the major survival factor that protects from oncogene induced cell death (Harrington et al., EMBO J. (1994) 13( ):3286-3295). IGF-1R is expressed in a large number and variety of tumors and the IGFs amplify the tumor growth through their interaction with the receptor. Evidence supporting the role of IGF-1R in carcinogenesis can be found in studies using monoclonal antibodies directed towards the receptor which inhibit the proliferation of numerous cell lines in culture and in vivo (Arteaga C et al., Cancer Res. (1989) 49(22):6237-6241; Li et al., Biochem. Biophys. Res. Com. (1993) 196(1):92-98; Scotlandi K et al., Cancer Res. (1998) 58(18):4127-4131). Dominant negative IGF-1R is capable of inhibiting tumor proliferation (Jiang et al., Oncogene (1999) 18(44):6071-6077). The IGF signaling axis is implicated in various tumor types including:

breast cancer (Surmacz, J. Mammary Gland Bio. Neoplasia (2000) 5(1):95-105, LeRoith, Can. Lett. (2003) and Artega, Cancer Res. (1989)), sarcoma including soft-tissue sarcoma (e.g., cartilage sarcoma, connective tissue (chondrosarcoma) and fibrous matrix (fibrosarcoma)) and hard bony sarcomas (e.g., Ewing's sarcoma, osteosarcoma and giant cell tumor of bone) (Scotlandi, Cancer Res. (1998), lung cancer, including non-small cell and small cell lung carcinomas and mesotheliomas (Jiang, Y et al., Oncogene (1999) 18:6071-6077 and LeRoith, Can. Lett. (2003), prostate cancer (Djavan et al., World J Urol. (2001) 19(4): 225-233; O'Brien et al., Urology (2001) 58(1):1-7 and LeRoith, Can. Lett. (2003)), colorectal cancer (Guo et al., Gastroenterology, 1992, 102, 1101-1108; Durai, R et al., Int. J Colorectal Dis. (2005) 20(3):203-220 and LeRoith, Can. Lett. (2003)), renal cancer (Kellerer M. et al., Int. J. Cancer (1995) 62(5): 501-507), pancreatic cancer (Bergmann, U et al., Cancer Res. (1995) 55(10):2007-2011), hematologic cancers, including lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, acute megakaryocytic leukemia, promyelocytic leukemia, erythroleukemia, malignant lymphoma, Hodgkins lymphoma, non-Hodgkins lymphoma, lymphoblastic T cell lymphoma, Burkitt's lymphoma, follicular lymphoma, myelodysplastic syndromes, (Zumkeller W et al., Leuk. Lymph (2002) 43(3): 487-491; and Qi, Ann Hematol. (2006) 85:95-101.), neuroblastomas (Zumkeller, W et al., Horm. Metab. Res. 1999, 31, 138-141), primary CNS tumors including: astrocytomas (also known as "gliomas") including glioblastoma multiforme; meningiomas and medulloblastomas (Zumkeller, W et al., Mol. Pathol. (2001) 54(4):227-229, Del Valle L, et al., Clin. Cancer Res. (2002) 8:1822-1830 and Trojan et al., Proc. Natl. Acad. Sci. USA (1992) 89:4874-4878.), secondary CNS tumors, i.e., metastases in the central nervous system (e.g., the brain), of a tumor originating outside of the central nervous system (Burfeind P, et al, PNAS (1996) 93:7263-7268), head and neck cancer (Wu X., et al, Clin. Cancer Res. (2004) 10:3988-95), thyroid cancer (Vella V et al., J. Clin. Endocrinol. Metab. (2002) 87:245-254; Vella V et al., Mol. Pathol. (2001) 54(3): 121-124), hepatocarcinoma (Alexia, C et al., Biochem. Pharmacol. (2004) 68:1003-1015), ovarian cancer, vulval cancer, cervical cancer, endometrial cancer, testicular cancer (Neuvians T P, et al, Neoplasia (2005) 7:446-56), bladder cancer (Zhao H., et al, J. Urology (2003) 169:714-717), esophageal cancer (Sohda M, et al, Anticancer Research. (2004) 24:3029-3034), gastric cancer (Jiang, Y, et al, Clinical & Experimental Metastasis (2004) 21:755-64), buccal cancer, cancer of the mouth, (Brady G et al., Int. J. of Oral & Maxillofacial Surg. (2007) 36:259-62).

GIST (gastrointestinal stromal tumor) (Trent J C, et al, Cancer. (2006) 107:1898-908), and skin cancer including melanoma (Yeh A H, et al, Oncogene. (2006) 25:6574-81).

Thus, in virtually all types of human cancers there is a strong association between dysregulation of IGF signaling and carcinogenesis (Bohula E A et al., Anticancer Drugs (2003) 14(9):669-682). Inhibition of IGF-1R and/or IR expression or function has been shown to block tumor growth and metastasis and also enhance sensitivity to other antineoplastic therapies, including cytotoxic drugs and radiation. (Bohula, Anticancer Drugs (2003).

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY

One embodiment pertains to compounds that have formula (I)

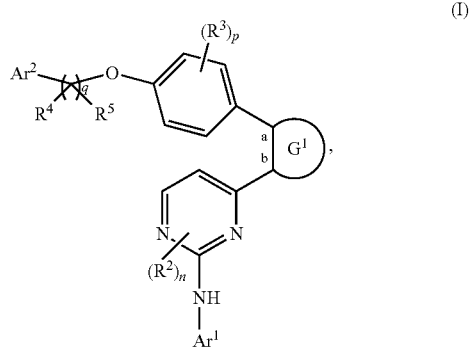

or pharmaceutically acceptable salts, solvates, prodrugs, salts of prodrugs, or combinations thereof, wherein G¹ is formula (i), (ii), (iii), or (iv)

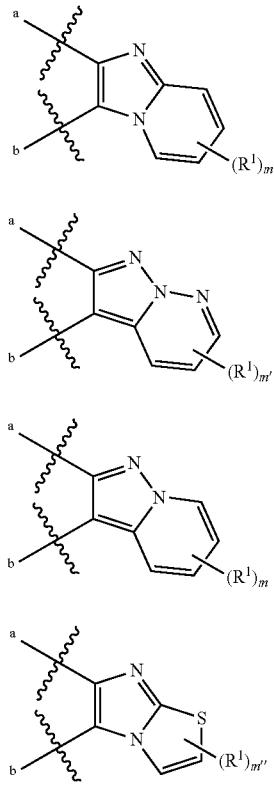

m is 0, 1, 2, 3, or 4;
m' is 0, 1, 2, or 3;
m'' is 0, 1, or 2;
n is 0, 1, or 2;
p is 0, 1, 2, 3, or 4;
$R^1$, $R^2$, and $R^3$ are optional substituents, and if present, are each independently alkyl, halogen, —O(alkyl), —O(haloalkyl), or haloalkyl;
a and b designate the points of attachment at which formula (i), (ii), (iii), (iv) are bound to formula (I);
$R^4$ and $R^5$, at each occurrence, are each independently hydrogen, alkyl, halogen, or haloalkyl;
q is 1, 2, 3, or 4;
$Ar^1$ is aryl or heteroaryl; each of which is independently unsubstituted or substituted with 1, 2, 3, 4, or 5 substituents as represented by T, wherein each T is selected from the group consisting of oxo, alkyl, alkenyl, alkynyl, halogen, haloalkyl, CN, $NO_2$, $G^2$, —$OR^6$, —$OC(O)R^7$, —$SR^6$, —$S(O)R^7$, —$S(O)_2R^7$, —$S(O)_2N(R^8)(R^9)$, —$N(R^8)(R^9)$, —$N(R^8)C(O)R^7$, —$N(R^8)C(O)OR^7$, —$N(R^8)S(O)_2R^7$, —$N(R^8)C(O)N(R^8)(R^9)$, —$N(R^8)C(O)$—($C_{1-6}$ alkylenyl)-$N(R^8)(R^9)$, —$N(R^8)S(O)_2N(R^8)(R^9)$, —$C(O)R^6$, —$C(O)OR^6$, —$C(O)N(R^8)(R^9)$, —($C_{1-6}$ alkylenyl)-$G^2$, —($C_{1-6}$ alkylenyl)-$OR^6$, —($C_{1-6}$ alkylenyl)-$OC(O)R^7$, —($C_{1-6}$ alkylenyl)-$SR^6$, —($C_{1-6}$ alkylenyl)-$S(O)R^7$, —($C_{1-6}$ alkylenyl)-$S(O)_2R^7$, —($C_{1-6}$ alkylenyl)-$S(O)_2N(R^8)(R^9)$, —($C_{1-6}$ alkylenyl)-$N(R^8)(R^9)$, —($C_{1-6}$ alkylenyl)-$N(R^8)C(O)R^7$, —($C_{1-6}$ alkylenyl)-$N(R^8)C(O)OR^7$, —($C_{1-6}$ alkylenyl)-$N(R^8)S(O)_2R^7$, —($C_{1-6}$ alkylenyl)-$N(R^8)C(O)N(R^8)(R^9)$, —($C_{1-6}$ alkylenyl)-$N(R^8)S(O)_2N(R^8)(R^9)$, —($C_{1-6}$ alkylenyl)-$C(O)R^6$, —($C_{1-6}$ alkylenyl)-$C(O)OR^6$, and —($C_{1-6}$ alkylenyl)-$C(O)N(R^8)(R^9)$, two substituents on the vicinal carbon atoms of $Ar^1$, together with the carbon atoms to which they are attached, optionally form a monocyclic 5- or 6-membered heterocycle containing one or two heteroatoms selected from N(H), O, S, S(O), or $S(O)_2$, wherein each of the monocyclic ring is optionally substituted with 1, 2, 3, or 4 alkyl groups;
each occurrence of $R^6$ and $R^9$ are each independently hydrogen, alkyl, haloalkyl, —($C_{1-6}$ alkylenyl)-CN, —($C_{1-6}$ alkylenyl)-OH, —($C_{1-6}$ alkylenyl)-C(O)OH, $G^3$, or —($C_{1-6}$ alkylenyl)-$G^3$;
each occurrence of $R^7$ is independently alkyl, haloalkyl, —($C_{1-6}$ alkylenyl)-CN, —($C_{1-6}$ alkylenyl)-OH, $G^3$, or —($C_{1-6}$ alkylenyl)-$G^3$;
each occurrence of $R^8$ is independently hydrogen, alkyl, or haloalkyl;
each occurrence of $G^2$ is independently aryl, heteroaryl, heterocycle, cycloalkyl, or cycloalkenyl, each of which is independently unsubstituted or substituted with 1, 2, 3, 4, or 5 substituents selected from the group consisting of $G^3$, —($C_{1-6}$ alkylenyl)-$G^3$, and $R^{10}$,
each occurrence of $G^3$ is independently aryl, heteroaryl, heterocycle, cycloalkyl, or cycloalkenyl, each of which is independently unsubstituted or substituted with 1, 2, 3, 4, or 5 $R^{10}$ groups;
$Ar^2$ is aryl or heteroaryl, each of which is independently unsubstituted or substituted with 1, 2, 3, 4, or 5 $R^{10}$ groups;
each occurrence of $R^{10}$ is independently alkyl, alkenyl, alkynyl, halogen, haloalkyl, oxo, CN, $NO_2$, —$OR^{Z1}$, —$OC(O)R^{Z2}$, —$SR^{Z1}$, —$S(O)R^{Z2}$, —$S(O)_2R^{Z2}$, —$S(O)_2N(R^{Z3})(R^{Z4})$, —$N(R^{Z3})(R^{Z4})$, —$N(R^{Z3})C(O)R^{Z2}$, —$N(R^{Z3})C(O)OR^{Z2}$, —$N(R^{Z3})S(O)_2R^{Z2}$, —$N(R^{Z3})C(O)N(R^{Z3})(R^{Z4})$, —$N(R^{Z3})S(O)_2N(R^{Z3})(R^{Z4})$, —$C(O)R^{Z1}$, —$C(O)OR^{Z1}$, —$C(O)N(R^{Z3})(R^{Z4})$, —($C_{1-6}$ alkylenyl)-$OR^{Z1}$, —($C_{1-6}$ alkylenyl)-$OC(O)R^{Z2}$, —($C_{1-6}$ alkylenyl)-$SR^{Z1}$, —($C_{1-6}$ alkylenyl)-$S(O)R^{Z2}$, —($C_{1-6}$ alkylenyl)-$S(O)_2R^{Z2}$, —($C_{1-6}$ alkylenyl)-$S(O)_2N(R^{Z3})(R^{Z4})$, —($C_{1-6}$ alkylenyl)-$N(R^{Z3})(R^{Z4})$, —($C_{1-6}$ alkylenyl)-$N(R^{Z3})C(O)R^{Z2}$, —($C_{1-6}$ alkylenyl)-$N(R^{Z3})C(O)OR^{Z2}$, —($C_{1-6}$ alkylenyl)-$N(R^{Z3})S(O)_2R^{Z2}$, —($C_{1-6}$ alkylenyl)-$N(R^{Z3})C(O)N(R^{Z3})(R^{Z4})$, —($C_{1-6}$ alkylenyl)-$N(R^{Z3})S(O)_2N(R^{Z3})(R^{Z4})$, —($C_{1-6}$ alkylenyl)-$C(O)R^{Z1}$, —($C_{1-6}$ alkylenyl)-$C(O)OR^{Z1}$, or —($C_{1-6}$ alkylenyl)-$C(O)N(R^{Z3})(R^{Z4})$,
each occurrence of $R^{Z1}$, $R^{Z3}$, and $R^{Z4}$, are each independently hydrogen, alkyl, or haloalkyl; and
each occurrence of $R^{Z2}$ is independently alkyl or haloalkyl.

Also provided are pharmaceutical compositions comprising therapeutically effective amounts of one or more compounds of formula (I) pharmaceutically acceptable salts thereof in combination with one or more pharmaceutically acceptable carriers. These pharmaceutical compositions are useful for the treatment of diseases or conditions described herein.

One embodiment is directed to methods of treating cancers in mammals comprising administering thereto therapeutically effective amounts of one or more compounds described herein, or pharmaceutically acceptable salts or solvates thereof, alone or in combination with one or more pharmaceutically acceptable carriers.

Yet another embodiment pertains to methods of decreasing tumor volume in mammals comprising administering thereto therapeutically effective amounts of one or more compounds described herein, or pharmaceutically acceptable salts or solvates thereof, alone or in combination with one or more pharmaceutically acceptable carriers.

Still another embodiment pertains to methods of treating bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer in mammals, the methods comprising administering thereto therapeutically effective amounts of one or more compounds described herein or pharmaceutically acceptable salts or solvates thereof, with or without also administering radiotherapy thereto, and alone or in combination with one or more pharmaceutically acceptable carriers.

Provided herein are also the use of one or more compounds described herein, or pharmaceutically acceptable salts or solvates thereof for the preparation of medicaments for use in the treatment of diseases or conditions described herein, particularly, for use in the treatment of bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer, in mammals (e.g., human) in need thereof.

The compounds, compositions comprising the compounds, and methods for treating or preventing conditions and disorders by administering the compounds and pharmaceutical compositions are further described herein.

These and other objectives of the invention are described in the following paragraphs. These objectives should not be deemed to narrow the scope of the invention.

DETAILED DESCRIPTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Provided are compounds of formula (I)

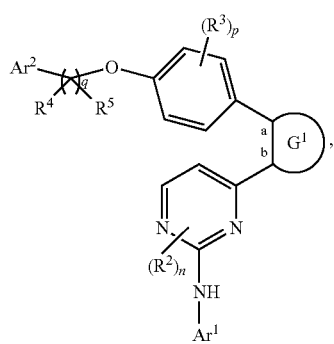

wherein $Ar^1$, $Ar^2$, $R^2$, $R^3$, $R^4$, $R^5$, $G^1$, n, p, and q are as disclosed above in the Summary and below in the Detailed Description. Compositions comprising such compounds and methods for treating conditions and disorders using such compounds and compositions are also disclosed.

In various embodiments, there may be variables that occur more than one time in any substituent or in the compound or any other formulae herein. Definition of a variable on each occurrence is independent of its definition at another occurrence. Further, combinations of variables are permissible only if such combinations result in stable compounds. Stable compounds are compounds that can be isolated from a reaction mixture.

a. Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. Non-limiting examples of alkenyl include ethenyl, 3-methylbut-2-enyl, prop-1-enyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a saturated, straight or branched hydrocarbon chain containing from 1 to 10 carbon atoms. The term "$C_{1-6}$ alkyl" as used herein, means a saturated, straight or branched chain hydrocarbon containing from 1 to 6 carbon atoms. Non-limiting examples of alkyl include methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a saturated, straight or branched hydrocarbon chain of from 1 to 10 carbon atoms. The term "$C_{1-6}$ alkylenyl" means a divalent group derived from a saturated, straight or branched hydrocarbon chain of from 1 to 6 carbon atoms. Non-limiting examples of alkylene include —CH$_2$—, —CH(CH$_3$)—, —CH$_2$C(CH$_3$)$_2$—, —CH(C$_2$H$_5$), —CH(CH(CH$_3$)(C$_2$H$_5$))—, —C(H)(CH$_3$)CH$_2$CH$_2$—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched hydrocarbon chain containing from 2 to 10 carbon atoms and containing at least one carbon-carbon triple bond. Non-limiting examples of alkynyl include acetylenyl, 1-propynyl, 2-propynyl, 1,1-dimethylprop-2-ynyl, 1-propyl-pent-3-ynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the bicyclic aryl include dihydroindenyl, indenyl, naphthyl, dihydronaphthalenyl, and tetrahydronaphthalenyl. The phenyl and the bicyclic aryls, with the exception of the bicyclic aryls represented by $Ar^1$ and $Ar^2$, are attached to the parent molecular moiety through any carbon atom contained within the phenyl and the bicyclic aryls respectively. The bicyclic aryls represented by $Ar^1$ and $Ar^2$ are attached to the parent moiety through any substitutable carbon atoms of the phenyl moiety within the group.

The term "cycloalkenyl" as used herein, means a monocyclic or bicyclic ring system containing zero heteroatoms in the ring. The monocyclic cycloalkenyl has three-, four-, five-, six-, seven- or eight carbon atoms and zero heteroatoms. The three or four-membered ring systems have one double bond, the five- or six-membered ring systems have one or two double bonds, and the seven- or eight-membered ring systems have one, two or three double bonds. Non-limiting examples of monocyclic cycloalkenyls include 2-cyclohexen-1-yl, 3-cyclohexen-1-yl, 2,4-cyclohexadien-1-yl and 3-cyclopenten-1-yl. Bicyclic cycloalkenyls are exemplified by a monocyclic cycloalkenyl fused to a monocyclic cycloalkyl, or a monocyclic cycloalkenyl fused to a monocyclic cycloalkenyl. Non-limiting examples of bicyclic ring systems include 3a,4,5,6,7,7a-hexahydro-1H-indenyl, 4,5,6,7-tetrahydro-3aH-indene, and octahydronaphthalenyl. The cycloalkenyl groups are appended to the parent molecular moiety through any substitutable carbon atom within the groups, and may contain one or two alkylene bridges of 1, 2, 3, or 4 carbon atoms, wherein each bridge links two non-adjacent atoms within the groups.

The term "cycloalkyl" as used herein, means a monocyclic, or a bicyclic cycloalkyl, or a spirocyclic cycloalkyl. The monocyclic cycloalkyl is a carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Non-limiting examples of bicyclic cycloalkyls include bicyclo[4.1.0]heptane, bicyclo[6.1.0]nonane, octahydroindene, and decahydronaphthalene. The monocyclic and the bicyclic cycloalkyl groups may contain one or two alkylene bridges of 1, 2, 3, or 4 carbon atoms, wherein each bridge links two non-adjacent atoms within the groups. Examples of such bridged cycloalkyls include, but are not limited to, bicyclo[2.2.1]heptyl, bicyclo[3.1.1]heptyl, bicyclo[2.2.2]octyl, bicyclo[3.3.1]nonyl, adamantyl (tricyclo[3.3.1.1$^{3,7}$]decane), and noradamantyl (octahydro-2,5-methanopentalene). Spirocyclic cycloalkyl is exemplified by a monocyclic or a bicyclic cycloalkyl, wherein two of the substituents on the same carbon atom of the ring, together with said carbon atom, form a 3-, 4-, 5-, or 6-membered monocyclic cycloalkyl. An example of a spirocyclic cycloalkyl is spiro[2.5]octane. The monocyclic, bicyclic, and spirocyclic cycloalkyl groups can be appended to the parent molecular moiety through any substitutable carbon atom of the groups.

The term "$C_{3-6}$ cycloalkyl" as used herein, means a 3-, 4-, 5-, or 6-membered monocyclic cycloalkyl as defined herein.

The term "halo" or "halogen" as used herein, means —Cl, —Br, —I or —F.

The term "haloalkyl" as used herein, means an alkyl group, as defined herein, in which one, two, three, four, five, six, or seven hydrogen atoms are replaced by halogen. Non-limiting examples of haloalkyl include, but are not limited to, chloromethyl, 2-fluoroethyl, 2-fluoropropyl, 2-fluoro-1-methylethyl, 2,2-difluoroethyl, trifluoromethyl, 2,2,2-trifluoroethyl, 2,2,2-trifluoro-1,1-dimethylethyl, difluoromethyl, 3-fluoro-3-methylbutyl, 3,3,3-trifluoropropyl, pentafluoroethyl, 2-chloro-3-fluoropentyl, and 2-iodoethyl.

The term "$C_{1-6}$ haloalkyl" as used herein, means a $C_{1-6}$ alkyl group, as defined herein, in which one, two, three, four, five, six, or seven hydrogen atoms are replaced by halogen.

The term "heteroaryl," as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Non-limiting examples of monocyclic heteroaryl include furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryls include, but are not limited to, benzofuranyl, benzoxadiazolyl, 1,3-benzothiazolyl, benzimidazolyl, benzodioxolyl, benzothienyl, chromenyl, cinnolinyl, furopyridine, indolyl, indazolyl, isoindolyl, isoquinolinyl, naphthyridinyl, oxazolopyridine, quinolinyl, and thienopyridinyl. The monocyclic and the bicyclic heteroaryl groups, with the exception of the bicyclic heteroaryl represented by Ar$^1$ and Ar$^2$, are connected to the parent molecular moiety through any substitutable carbon atom or any substitutable nitrogen atom contained within the groups. The bicyclic heteroaryls represented by Ar$^1$ and Ar$^2$ are connected to the parent molecular moiety through any substitutable carbon atoms of the monocyclic heteroaryl moiety of the group. The nitrogen and sulfur heteroatoms of the heteroaryl rings may optionally be oxidized, and are contemplated within the scope of the invention.

The term "heterocycle" or "heterocyclic" as used herein, means a monocyclic or a bicyclic, or a spirocyclic ring system containing at least one heteroatom. The monocyclic heterocycle is a 3-, 4-, 5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6-, 7-, or 8-membered ring contains zero, one, or two double bonds, and one, two, or three heteroatoms in the ring selected from the group consisting of O, N and S, Non-limiting examples of monocyclic heterocycles include azetidinyl, azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Non-limiting examples of bicyclic heterocycle include 1,3-benzodioxol-4-yl, 1,3-benzodithiolyl, 2,3-dihydro-1,4-benzodioxinyl, dihydrobenzofuranyl, 2,3-dihydro-1-benzothienyl, 2,3-dihydro-1H-indolyl, and 1,2,3,4-tetrahydroquinolinyl. Spirocyclic heterocycle means a monocyclic or bicyclic heterocycle ring wherein two substituents on the same carbon atom, together with said carbon atom, form a 3-, 4-, 5-, or 6-membered monocyclic cycloalkyl or a monocyclic heterocycle. One example of a spirocyclic heterocycle is 5-oxaspiro[3,4]octane. The monocyclic, bicyclic, and spirocyclic heterocycle groups are connected to the parent molecular moiety through any substitutable carbon atom or any substitutable nitrogen atom contained within the group. The monocyclic or bicyclic heterocycle groups may contain an alkenylene bridge of 2, 3, or 4 carbon atoms, or one or two alkylene bridges of 1, 2, 3, or 4 carbon atoms, wherein each bridge links two non-adjacent carbon atoms within the groups. Examples of such bridged heterocycles include, but are not limited to, oxaadamantane (2-oxatricyclo[3.3.1.1$^{3,7}$]decane), octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4- dioxabicyclo[4.2.1]nonane. The nitrogen and sulfur heteroatoms in the heterocycle rings may optionally be oxidized (e.g. 1,1-dioxidothiomorpholinyl (thiomorpholine sulfone)), and the nitrogen atoms may optionally be quarternized.

If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 5 non-hydrogen radicals, then any heteroaryl with less than 5 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical.

The term "oxo" as used herein, means a =O group.

The terms "treat", "treating," and "treatment" refer to a method of alleviating or abrogating a disease and/or its attendant symptoms.

The terms "prevent", "preventing," and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

b. Compounds

IGF-1R inhibitors have formula (I) as described in the Summary.

Particular values of variable groups in compounds of formula (I) are as follows. Such values may be used where appropriate with any of the other values, definitions, claims or embodiments defined hereinbefore or hereinafter.

In compounds of formula (I), ring $G^1$ has values as disclosed in the Summary.

In certain embodiments, ring $G^1$ is formula (I). Thus, examples of compounds include herein, but not limited to, are those of formula (I-i)

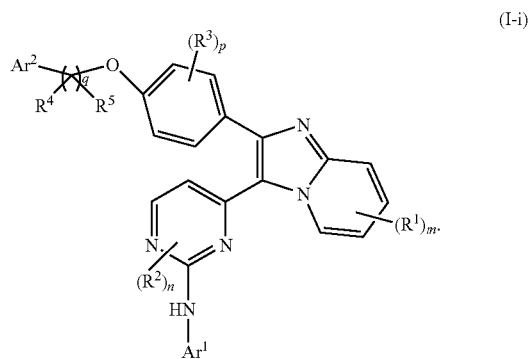

(I-i)

Other embodiments provide compounds of formula (I) wherein $G^1$ is formula (ii). Examples include those having formula (I-ii)

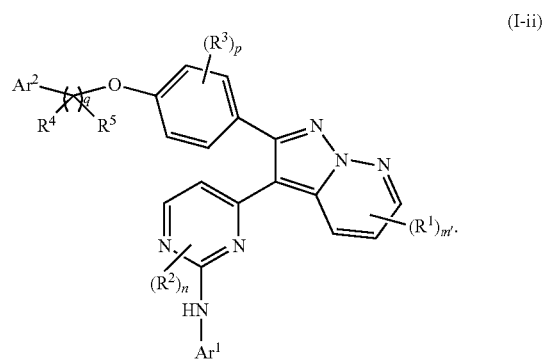

(I-ii)

Yet other embodiments include those wherein ring $G^1$ is formula (iii) such as those of formula (I-iii)

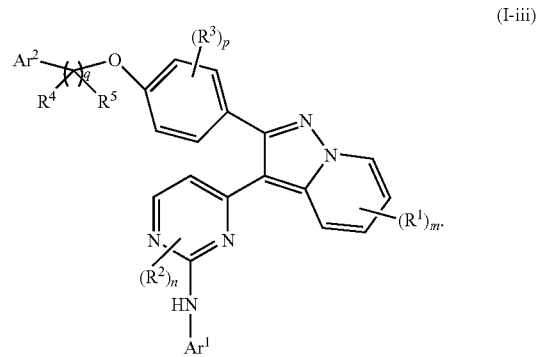

(I-iii)

Still another class of compounds of formula (I) include those wherein $G^1$ is formula (iv), such as those of formula (I-iv)

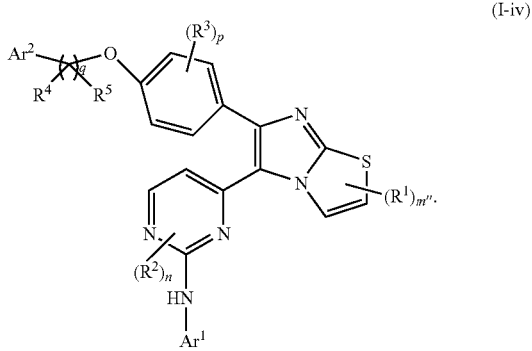
(I-iv)

Variables $Ar^1$, $Ar^2$, $R^1$, $R^2$, $R^3$, $R^4$, $R^5$, m, m', m'', n, p, and q for compounds of formula (I-i), (I-ii), (I-iii), (I-iv) are as disclosed above in the Summary and below in the Detailed Description sections.

In conjunction with any above or below embodiments, m for compounds of formula (I), (I-i), or (I-iii) has meanings as provided for in the Summary section. For example, one embodiment pertains to compounds of formula (I), (I-i), or (I-iii) wherein m is 0. In one embodiment of compounds of formula (I), (I-i), or (I-iii), m is 1 or 2.

In conjunction with any above or below embodiments, m' for compounds of formula (I) or (I-ii) has meanings as provided for in the Summary section. For example, one class of compounds of formula (I) or (I-ii) include those defined wherein m' is 0. In another embodiment m' is 1 or 2.

In conjunction with any above or below embodiments, m' for compounds of formula (I) or (I-iv) has meanings as provided for in the Summary section. For example, one class of compounds of formula (I) or (I-iv) include those defined wherein m'' is 0. In another embodiment m'' is 1 or 2.

One class of compounds of formula (I), (I-i), (I-ii), (I-iii), or (I-iv) includes those defined wherein each of the optional substituent, $R^1$, is independently $C_{1-6}$ alkyl, halogen, or $C_{1-6}$ haloalkyl. In one embodiment, each of the optional substituent, $R^1$, is independently $C_{1-6}$ alkyl or halogen. For example, $R^1$ is methyl or F.

In one class of compounds of formula (I), (I-i), (I-ii), (I-iii), or (I-iv), n is 0. In another class of compounds, n is 1 or 2.

In the class of compounds of formula (I), (I-i), (I-ii), (I-iii), or (I-iv) wherein n is 1 or 2, $R^2$ is as defined in the Summary. In certain embodiments, $R^2$ is $C_{1-6}$ alkyl, halogen, or $C_{1-6}$ haloalkyl. In one embodiment, the optional substituent, $R^2$, is $C_{1-6}$ alkyl. For example, $R^2$ is methyl.

In one class of compounds of formula (I), (I-i), (I-ii), (I-iii), or (I-iv), p is 0. In another class of compounds, p is 1 or 2.

In the class of compounds of formula (I), (I-i), (I-ii), (I-iii), or (I-iv) wherein p is 1 or 2, $R^3$ is as defined in the Summary. In certain embodiments, each $R^3$ is independently selected from the group consisting of $C_{1-6}$ alkyl, halogen, —O($C_{1-6}$ alkyl), —O($C_{1-6}$ haloalkyl), and $C_{1-6}$ haloalkyl. For example, each $R^3$ is independently selected from the group consisting of methyl, ethyl, F, Cl, —O(methyl), —O(trifluoromethyl), and trifluoromethyl.

One class of compounds of formula (I), (I-i), (I-ii), (I-iii), or (I-iv) includes those wherein p is 1 or 2, and at least one of $R^3$ is —O($C_{1-6}$ alkyl), particularly, —O(methyl).

One class of compounds of formula (I), (I-i), (I-ii), (I-iii), or (I-iv) includes those wherein p is 1, $R^3$ is —O($C_{1-6}$ alkyl), particularly, —O(methyl), located on the meta position relative to the carbon atom that is bound to ring $G^1$.

One class of compounds of formula (I), (I-i), (I-ii), (I-iii), or (I-iv) includes those wherein q is 1 or 2. In certain embodiments, q is 1.

$R^4$ and $R^5$ have values as disclosed in the Summary. In one embodiment of compounds of formula (I), (I-i), (I-ii), (I-iii), or (I-iv), $R^4$ and $R^5$ are the same or different, and are each independently selected from the group consisting of hydrogen and alkyl (for example, $C_{1-6}$ alkyl such as, but not limited to, methyl). In other embodiment, $R^4$ and $R^5$ are both hydrogen. In another embodiment, one of $R^4$ and $R^5$ is hydrogen, and the other is $C_{1-6}$ alkyl such as, but not limited to, methyl.

$Ar^2$ has values as described in the Summary. In one embodiment, $Ar^2$ is optionally substituted aryl. In another embodiment, $Ar^2$ is optionally substituted heteroaryl. In yet another embodiment, $Ar^2$ is optionally substituted phenyl.

The optional substituents of $Ar^2$ are as defined in the Summary. In conjunction with any above or below embodiments of compounds of formula (I), (I-i), (I-ii), (I-iii), or (I-iv), each of these optional substituents of $Ar^2$ can be the same or different and are, for example, independently alkyl (e.g. $C_{1-6}$ alkyl such as but not limited to, methyl), halogen, (e.g. Cl, F, and the like), haloalkyl (e.g. $C_{1-6}$ haloalkyl such as but not limited to, trifluoromethyl), or —$OR^{z1}$ wherein $R^{z1}$ is as disclosed in the Summary. In certain embodiments, $R^{z1}$ is $C_{1-6}$ alkyl such as but not limited to, methyl.

$Ar^1$ has values as described in the Summary. For example, in conjunction with any above or below embodiments of compounds of formula (I), (I-i), (I-ii), (I-iii), or (I-iv), $Ar^1$ is phenyl or monocyclic heteroaryl, each of which is optionally substituted as described in the Summary and Detailed Description sections. In one embodiment, $Ar^1$ is optionally substituted aryl. In another embodiment, $Ar^1$ is an optionally substituted heteroaryl, for example, an optionally substituted monocyclic heteroaryl. In yet another embodiment, $Ar^1$ is optionally substituted phenyl. In still another embodiment, $Ar^1$ is optionally substituted pyrazolyl.

The optional substituents of $Ar^1$ are as defined in the Summary. For example, in conjunction with any above or below embodiments of compounds of formula (I), (I-i), (I-ii), (I-iii), or (I-iv), each of the optional substituents of $Ar^1$ are the same or different, and are each independently alkyl (e.g. $C_{1-6}$ alkyl such as, but not limited to, methyl), halogen (e.g. F, Cl, and the like), haloalkyl (e.g. $C_{1-6}$ haloalkyl such as, but not limited to, trifluoromethyl), $G^2$ (e.g. heterocycle such as, but not limited to, morpholinyl, piperazinyl, pyrrolidinyl, thiomorpholinyl, piperidinyl, 1,1-dioxidothiomorpholinyl, and the like; and $C_{3-6}$ monocyclic cycloalkyl such as, but not limited to, cyclopropyl; each of these rings is optionally substituted as described in the Summary), —$OR^6$, —$S(O)_2R^7$, —$S(O)_2N(R^8)(R^9)$, —$N(R^8)(R^9)$, —$N(R^8)C(O)$—($C_{1-6}$ alkylenyl)-$N(R^8)(R^9)$, —($C_{1-6}$ alkylenyl)-$G^2$ ($G^2$, for example, is heterocycle such as, but not limited to, morpholinyl, piperazinyl, pyrrolidinyl, thiomorpholinyl, piperidinyl, and the like, each of which is optionally substituted as described in the Summary), —($C_{1-6}$ alkylenyl)-$OR^6$, or —($C_{1-6}$ alkylenyl)-$N(R^8)(R^9)$ wherein $R^6$, $R^7$, $R^8$, and $R^9$ are as described in the Summary. When $Ar^1$ is phenyl, two substituents on the vicinal carbon atoms of $Ar^1$, together with the carbon atoms to which they are attached, may form a monocyclic heterocycle ring as described in the Summary, for example, they may form a monocyclic heterocycle such as

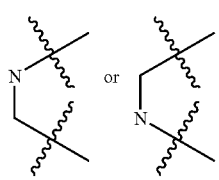

wherein each of these rings is optionally substituted as described in the Summary.

It is appreciated that compounds of formula (I), (I-i), (I-ii), (I-iii), and (I-iv) with combinations of the above embodiments and subsets of the particular groups defined, including particular, more particular and preferred embodiments are contemplated.

Accordingly, one aspect relates to a group of compounds of formula (I), (I-i), (I-ii), (I-iii), and (I-iv) wherein $Ar^2$ and $Ar^1$ are optionally substituted phenyl.

Another aspect relates to a group of compounds of formula (I), (I-i), (I-ii), (I-iii), or (I-iv) wherein $Ar^2$ is optionally substituted phenyl, and $Ar^1$ is optionally substituted heteroaryl.

Yet another aspect relates to a group of compounds of formula (I), (I-i), (I-ii), (I-iii), or (I-iv) wherein $Ar^2$ is optionally substituted phenyl, and $Ar^1$ is optionally substituted monocyclic heteroaryl.

Yet another aspect relates to a group of compounds of formula (I), (I-i), (I-ii), (I-iii), or (I-iv) wherein $Ar^2$ is optionally substituted phenyl, and $Ar^1$ is optionally substituted pyrazolyl.

Within each group of compounds of formula (I), (I-i), (I-ii), (I-iii), or (I-iv) as described in the preceding paragraphs, $R^1$, $R^2$, $R^3$, $R^4$, $R^5$, m, m', m", n, p, q, and the optional substituents of $Ar^1$ and $Ar^2$, are as described in the Summary and Detailed Description.

Thus, of each group of compounds of formula (I), (I-i), (I-ii), (I-iii), or (I-iv) as described in the preceding paragraphs, examples of a subgroup include, but are not limited to, those wherein m, m', m", and n are 0.

Examples of another subgroup of compounds of formula (I), (I-i), (I-ii), (I-iii), or (I-iv) include, but are not limited to, those wherein m, m', m", n, and p are 0

Examples of another subgroup of compounds of formula (I), (I-i), (I-ii), (I-iii), or (I-iv) include, but are not limited to, those wherein m, m', m", and n are 0, p is 1 or 2, $R^3$ is selected from the group consisting of $C_{1-6}$ alkyl, halogen, —O($C_{1-6}$ alkyl), —O($C_{1-6}$ haloalkyl), and $C_{1-6}$ haloalkyl. For example, $R^3$ is selected from the group consisting of methyl, ethyl, F, Cl, —O(methyl), —O(trifluoromethyl), and trifluoromethyl.

Yet other examples of a subgroup of compounds of formula (I), (I-i), (I-ii), (I-iii), or (I-iv) include, but are not limited to, those wherein m, m', m", and n are 0, p is 1, and $R^3$ is —O($C_{1-6}$ alkyl) (e.g. —O(methyl)).

For each of the groups and subgroups of compounds of formula (I), (I-i), (I-ii), (I-iii), or (I-iv) described above, $R^4$, $R^5$, and q are as described in the Summary and Detailed description. For example, q is 1 or 2. In certain embodiments, q is 1. For example, $R^4$ and $R^5$ are the same or different, and are each independently selected from the group consisting of hydrogen and alkyl (for example, $C_{1-6}$ alkyl such as, but not limited to, methyl). In other embodiment, $R^4$ and $R^5$ are both hydrogen. In another embodiment, one of $R^4$ and $R^5$ is hydrogen, and the other is $C_{1-6}$ alkyl such as, but not limited to, methyl.

Non limiting examples of compounds of formula (I), (I-i), (I-ii), (I-iii), and (I-iv) include, but are not limited to, 4-{2-[4-(benzyloxy)phenyl]imidazo[1,2-a]pyridin-3-yl}-N-{3-[2-(dimethylamino)ethyl]phenyl}pyrimidin-2-amine;
4-{2-[4-(benzyloxy)phenyl]imidazo[1,2-a]pyridin-3-yl}-N-(2-methoxy-4-morpholin-4-ylphenyl)pyrimidin-2-amine;
4-{2-[4-(benzyloxy)phenyl]imidazo[1,2-a]pyridin-3-yl}-N-(2-methoxyphenyl)pyrimidin-2-amine;
4-{2-[4-(benzyloxy)phenyl]imidazo[1,2-a]pyridin-3-yl}-N-[3-(methylsulfonyl)phenyl]pyrimidin-2-amine;
3-[(4-{2-[4-(benzyloxy)phenyl]imidazo[1,2-a]pyridin-3-yl}pyrimidin-2-yl)amino]-N,N-dimethylbenzenesulfonamide;
4-{2-[4-(benzyloxy)phenyl]imidazo[1,2-a]pyridin-3-yl}-N-[4-(methylsulfonyl)phenyl]pyrimidin-2-amine;
4-{2-[4-(benzyloxy)phenyl]imidazo[1,2-a]pyridin-3-yl}-N-phenylpyrimidin-2-amine;
4-{2-[4-(benzyloxy)-2-fluorophenyl]imidazo[1,2-a]pyridin-3-yl}-N-{3-[2-(dimethylamino)ethyl]phenyl}pyrimidin-2-amine;
4-{2-[4-(benzyloxy)-3-fluorophenyl]imidazo[1,2-a]pyridin-3-yl}-N-{3-[2-(dimethylamino)ethyl]phenyl}pyrimidin-2-amine;
4-{2-[4-(benzyloxy)-2-methylphenyl]imidazo[1,2-a]pyridin-3-yl}-N-{3-[2-(dimethylamino)ethyl]phenyl}pyrimidin-2-amine;
4-{2-[4-(benzyloxy)-3-chlorophenyl]imidazo[1,2-a]pyridin-3-yl}-N-{3-[2-(dimethylamino)ethyl]phenyl}pyrimidin-2-amine;
4-{2-[4-(benzyloxy)-3-methoxyphenyl]imidazo[1,2-a]pyridin-3-yl}-N-{3-[2-(dimethylamino)ethyl]phenyl}pyrimidin-2-amine;
4-{2-[4-(benzyloxy)phenyl]imidazo[1,2-a]pyridin-3-yl}-N-{2-methoxy-4-[4-(4-methylpiperazin-1-yl)piperidin-1-yl]phenyl}pyrimidin-2-amine;
4-{2-[4-(benzyloxy)phenyl]imidazo[1,2-a]pyridin-3-yl}-N-(5-methyl-1H-pyrazol-3-yl)pyrimidin-2-amine;
4-{2-[4-(benzyloxy)phenyl]imidazo[1,2-a]pyridin-3-yl}-N-(3-cyclopropyl-1H-pyrazol-5-yl)pyrimidin-2-amine;
N-{3-[2-(dimethylamino)ethyl]phenyl}-4-(2-{4-[(2-methoxybenzyl)oxy]phenyl}imidazo[1,2-a]pyridin-3-yl)pyrimidin-2-amine;
N-{3-[2-(dimethylamino)ethyl]phenyl}-4-(2-{4-[(4-methoxybenzyl)oxy]phenyl}imidazo[1,2-a]pyridin-3-yl)pyrimidin-2-amine;
N-{3-[2-(dimethylamino)ethyl]phenyl}-4-(2-{4-[(2-fluorobenzyl)oxy]phenyl}imidazo[1,2-a]pyridin-3-yl)pyrimidin-2-amine;
N-{3-[2-(dimethylamino)ethyl]phenyl}-4-(2-{4-[(3-fluorobenzyl)oxy]phenyl}imidazo[1,2-a]pyridin-3-yl)pyrimidin-2-amine;
N-{3-[2-(dimethylamino)ethyl]phenyl}-4-(2-{4-[(4-fluorobenzyl)oxy]phenyl}imidazo[1,2-a]pyridin-3-yl)pyrimidin-2-amine;
N-{3-[2-(dimethylamino)ethyl]phenyl}-4-{2-[4-(1-phenylethoxy)phenyl]imidazo[1,2-a]pyridin-3-yl}pyrimidin-2-amine;
4-{2-[4-(benzyloxy)phenyl]imidazo[1,2-a]pyridin-3-yl}-N-(4-chloro-2-methoxyphenyl)pyrimidin-2-amine;
4-{2-[4-(benzyloxy)-3-methoxyphenyl]imidazo[1,2-a]pyridin-3-yl}-N-[4-(2-pyrrolidin-1-ylethyl)phenyl]pyrimidin-2-amine;
4-{2-[4-(benzyloxy)-3-methoxyphenyl]imidazo[1,2-a]pyridin-3-yl}-N-[3-(2-pyrrolidin-1-ylethyl)phenyl]pyrimidin-2-amine;
4-{2-[4-(benzyloxy)-3-methoxyphenyl]imidazo[1,2-a]pyridin-3-yl}-N-(3-morpholin-4-ylphenyl)pyrimidin-2-amine;

4-{2-[4-(benzyloxy)phenyl]imidazo[1,2-a]pyridin-3-yl}-N-(1-methyl-1H-pyrazol-4-yl)pyrimidin-2-amine;

2-{4-[(4-{2-[4-(benzyloxy)phenyl]imidazo[1,2-a]pyridin-3-yl}pyrimidin-2-yl)amino]-1H-pyrazol-1-yl}ethanol;

4-{2-[4-(benzyloxy)phenyl]imidazo[1,2-a]pyridin-3-yl}-N-(4-fluorophenyl)pyrimidin-2-amine;

4-{2-[4-(benzyloxy)phenyl]imidazo[1,2-a]pyridin-3-yl}-N-(2,4-difluorophenyl)pyrimidin-2-amine;

4-{2-[4-(benzyloxy)-3-methoxyphenyl]imidazo[1,2-a]pyridin-3-yl}-N-[3-(2-pyrrolidin-1-ylethoxy)phenyl]pyrimidin-2-amine;

2-[{3-[(4-{2-[4-(benzyloxy)-3-methoxyphenyl]imidazo[1,2-a]pyridin-3-yl}pyrimidin-2-yl)amino]phenyl}(ethyl)amino]ethanol;

4-{2-[4-(benzyloxy)-3-methoxyphenyl]imidazo[1,2-a]pyridin-3-yl}-N-[4-(1,1-dioxidothiomorpholin-4-yl)phenyl]pyrimidin-2-amine;

4-{2-[4-(benzyloxy)-3-methoxyphenyl]imidazo[1,2-a]pyridin-3-yl}-N-{4-[4-(dimethylamino)piperidin-1-yl]-2-methoxyphenyl}pyrimidin-2-amine;

4-{2-[4-(benzyloxy)-3-methoxyphenyl]imidazo[1,2-a]pyridin-3-yl}-N-[2-methoxy-5-(methylsulfonyl)phenyl]pyrimidin-2-amine;

4-{2-[4-(benzyloxy)phenyl]imidazo[1,2-a]pyridin-3-yl}-N-[2-methoxy-5-(methylsulfonyl)phenyl]pyrimidin-2-amine;

4-{2-[4-(benzyloxy)-3-methoxyphenyl]imidazo[1,2-a]pyridin-3-yl}-N-{4-[4-(dimethylamino)piperidin-1-yl]phenyl}pyrimidin-2-amine;

4-{2-[4-(benzyloxy)-3-methoxyphenyl]imidazo[1,2-a]pyridin-3-yl}-N-[1-(2-pyrrolidin-1-ylethyl)-1H-pyrazol-4-yl]pyrimidin-2-amine;

2-[(2-{3-[(4-{2-[4-(benzyloxy)-3-methoxyphenyl]imidazo[1,2-a]pyridin-3-yl}pyrimidin-2-yl)amino]phenyl}ethyl)(methyl)amino]ethanol;

4-{2-[4-(benzyloxy)-3-methoxyphenyl]imidazo[1,2-a]pyridin-3-yl}-N-(2-methoxy-4-morpholin-4-ylphenyl)pyrimidin-2-amine;

4-{2-[4-(benzyloxy)-3-methoxyphenyl]imidazo[1,2-a]pyridin-3-yl}-N-[2-methoxy-5-(trifluoromethyl)phenyl]pyrimidin-2-amine;

4-{2-[4-(benzyloxy)phenyl]imidazo[1,2-a]pyridin-3-yl}-N-[2-methoxy-5-(trifluoromethyl)phenyl]pyrimidin-2-amine;

$N^1$-(4-{2-[4-(benzyloxy)-3-methoxyphenyl]imidazo[1,2-a]pyridin-3-yl}pyrimidin-2-yl)-2-methoxy-$N^4$,$N^4$-dimethylbenzene-1,4-diamine;

4-{2-[4-(benzyloxy)-3-methoxyphenyl]imidazo[1,2-a]pyridin-3-yl}-N-{1-[2-(dimethylamino)ethyl]-1H-pyrazol-4-yl}pyrimidin-2-amine;

2-(4-{4-[(4-{2-[4-(benzyloxy)-3-methoxyphenyl]imidazo[1,2-a]pyridin-3-yl}pyrimidin-2-yl)amino]phenyl}piperazin-1-yl)ethanol;

1-({4-[(4-{2-[4-(benzyloxy)-3-methoxyphenyl]imidazo[1,2-a]pyridin-3-yl}pyrimidin-2-yl)amino]-3-methoxyphenyl}amino)-2-methylpropan-2-ol;

$N^1$-(4-{2-[4-(benzyloxy)-3-methoxyphenyl]imidazo[1,2-a]pyridin-3-yl}pyrimidin-2-yl)-2-methoxybenzene-1,4-diamine;

2-{4-[(4-{2-[4-(benzyloxy)-3-methoxyphenyl]imidazo[1,2-a]pyridin-3-yl}pyrimidin-2-yl)amino]-1H-pyrazol-1-yl}ethanol;

2-[{4-[(4-{2-[4-(benzyloxy)-3-methoxyphenyl]imidazo[1,2-a]pyridin-3-yl}pyrimidin-2-yl)amino]-3-methoxyphenyl}(methyl)amino]ethanol;

4-{2-[4-(benzyloxy)-3-(trifluoromethyl)phenyl]imidazo[1,2-a]pyridin-3-yl}-N-{3-[2-(dimethylamino)ethyl]phenyl}pyrimidin-2-amine;

4-{2-[4-(benzyloxy)-3-ethylphenyl]imidazo[1,2-a]pyridin-3-yl}-N-{3-[2-(dimethylamino)ethyl]phenyl}pyrimidin-2-amine;

4-{2-[4-(benzyloxy)-3-methoxyphenyl]imidazo[1,2-a]pyridin-3-yl}-N-(2-methoxy-4-thiomorpholin-4-ylphenyl)pyrimidin-2-amine;

4-{2-[4-(benzyloxy)-3-methoxyphenyl]imidazo[1,2-a]pyridin-3-yl}-N-(2-methoxy-5-morpholin-4-ylphenyl)pyrimidin-2-amine;

N-{4-[(4-{2-[4-(benzyloxy)-3-methoxyphenyl]imidazo[1,2-a]pyridin-3-yl}pyrimidin-2-yl)amino]-3-methoxyphenyl}glycine;

4-{2-[4-(benzyloxy)-3-methoxyphenyl]imidazo[1,2-a]pyridin-3-yl}-N-[1-(2-piperidin-1-ylethyl)-1H-pyrazol-4-yl]pyrimidin-2-amine;

4-{2-[4-(benzyloxy)-3-methoxyphenyl]imidazo[1,2-a]pyridin-3-yl}-N-[1-(2-morpholin-4-ylethyl)-1H-pyrazol-4-yl]pyrimidin-2-amine;

4-{2-[4-(benzyloxy)-3-methoxyphenyl]imidazo[1,2-a]pyridin-3-yl}-N-[2-methoxy-4-(4-thiomorpholin-4-ylpiperidin-1-yl)phenyl]pyrimidin-2-amine;

4-{2-[4-(benzyloxy)-3-methoxyphenyl]imidazo[1,2-a]pyridin-3-yl}-N-(2-methoxy-4-piperidin-4-ylphenyl)pyrimidin-2-amine;

4-{2-[4-(benzyloxy)-3-(trifluoromethoxy)phenyl]imidazo[1,2-a]pyridin-3-yl}-N-[3-(2-pyrrolidin-1-ylethyl)phenyl]pyrimidin-2-amine;

4-{2-[4-(benzyloxy)-3-methoxyphenyl]imidazo[1,2-a]pyridin-3-yl}-N-{5-[2-(dimethylamino)ethyl]-2-methoxyphenyl}pyrimidin-2-amine;

N-(4-{2-[4-(benzyloxy)-3-methoxyphenyl]imidazo[1,2-a]pyridin-3-yl}pyrimidin-2-yl)-2-methyl-1,2,3,4-tetrahydroisoquinolin-7-amine;

N-(4-{2-[4-(benzyloxy)-3-methoxyphenyl]imidazo[1,2-a]pyridin-3-yl}pyrimidin-2-yl)-1,2,3,4-tetrahydroisoquinolin-6-amine;

N-(4-{2-[4-(benzyloxy)-3-methoxyphenyl]imidazo[1,2-a]pyridin-3-yl}pyrimidin-2-yl)-1,2,3,4-tetrahydroisoquinolin-7-amine;

4-{2-[4-(benzyloxy)-3-methoxyphenyl]imidazo[1,2-a]pyridin-3-yl}-N-[4-(1,1-dioxidothiomorpholin-4-yl)-2-methoxyphenyl]pyrimidin-2-amine;

2-[{3-[(4-{2-[4-(benzyloxy)-3-methoxyphenyl]imidazo[1,2-a]pyridin-3-yl}pyrimidin-2-yl)amino]-4-methoxybenzyl}(methyl)amino]ethanol;

$N^1$-{4-[(4-{2-[4-(benzyloxy)-3-methoxyphenyl]imidazo[1,2-a]pyridin-3-yl}pyrimidin-2-yl)amino]phenyl}-$N^2$,$N^2$-dimethylglycinamide;

$N^1$-{3-[(4-{2-[4-(benzyloxy)-3-methoxyphenyl]imidazo[1,2-a]pyridin-3-yl}pyrimidin-2-yl)amino]phenyl}-$N^2$,$N^2$-dimethylglycinamide;

$N^1$-{3-[(4-{2-[4-(benzyloxy)phenyl]imidazo[1,2-a]pyridin-3-yl}pyrimidin-2-yl)amino]phenyl}-$N^2$,$N^2$-dimethylglycinamide;

4-{2-[4-(benzyloxy)-3-methylphenyl]imidazo[1,2-a]pyridin-3-yl}-N-{3-[2-(dimethylamino)ethyl]phenyl}pyrimidin-2-amine;

4-{2-[4-(benzyloxy)-3-methoxyphenyl]imidazo[1,2-a]pyridin-3-yl}-N-{4-[2-(dimethylamino)ethyl]phenyl}pyrimidin-2-amine;

1-{3-[(4-{2-[4-(benzyloxy)-3-methoxyphenyl]imidazo[1,2-a]pyridin-3-yl}pyrimidin-2-yl)amino]benzyl}pyrrolidin-3-ol;

N¹-{3-[(4-{2-[4-(benzyloxy)-3-methoxyphenyl]imidazo[1,2-a]pyridin-3-yl}pyrimidin-2-yl)amino]-4-methoxyphenyl}-N²,N²-dimethylglycinamide;

N¹-{3-[(4-{2-[4-(benzyloxy)phenyl]imidazo[1,2-a]pyridin-3-yl}pyrimidin-2-yl)amino]-4-methoxyphenyl}-N²,N²-dimethylglycinamide;

4-{2-[4-(benzyloxy)-3-methoxyphenyl]imidazo[1,2-a]pyridin-3-yl}-N-(2-methoxy-5-thiomorpholin-4-ylphenyl)pyrimidin-2-amine;

4-{2-[4-(benzyloxy)-3-methoxyphenyl]imidazo[1,2-a]pyridin-3-yl}-N-[5-(1,1-dioxidothiomorpholin-4-yl)-2-methoxyphenyl]pyrimidin-2-amine;

4-{2-[4-(benzyloxy)phenyl]pyrazolo[1,5-a]pyridin-3-yl}-N-{3-[2-(dimethylamino)ethyl]phenyl}pyrimidin-2-amine;

4-{2-[4-(benzyloxy)phenyl]pyrazolo[1,5-b]pyridazin-3-yl}-N-{3-[2-(dimethylamino)ethyl]phenyl}pyrimidin-2-amine;

4-{2-[4-(benzyloxy)phenyl]-6-fluoropyrazolo[1,5-a]pyridin-3-yl}-N-{3-[2-(dimethylamino)ethyl]phenyl}pyrimidin-2-amine;

4-{6-[4-(benzyloxy)phenyl]imidazo[2,1-b][1,3]thiazol-5-yl}-N-phenylpyrimidin-2-amine;

4-{6-[4-(benzyloxy)phenyl]imidazo[2,1-b][1,3]thiazol-5-yl}-N-(2-methoxyphenyl)pyrimidin-2-amine;

4-{6-[4-(benzyloxy)phenyl]imidazo[2,1-b][1,3]thiazol-5-yl}-N-{4-[4-(dimethylamino)piperidin-1-yl]-2-methoxyphenyl}pyrimidin-2-amine;

N¹-(4-{6-[4-(benzyloxy)-3-methoxyphenyl]imidazo[2,1-b][1,3]thiazol-5-yl}pyrimidin-2-yl)-2-methoxy-N⁴,N⁴-dimethylbenzene-1,4-diamine 4-{6-[4-(benzyloxy)-3-methoxyphenyl]imidazo[2,1-b][1,3]thiazol-5-yl}-N-[2-(pyrrolidin-1-ylmethyl)phenyl]pyrimidin-2-amine;

4-{6-[4-(benzyloxy)-3-methoxyphenyl]imidazo[2,1-b][1,3]thiazol-5-yl}-N-{4-[(dimethylamino)methyl]phenyl}pyrimidin-2-amine;

4-{6-[4-(benzyloxy)-3-methoxyphenyl]imidazo[2,1-b][1,3]thiazol-5-yl}-N-{4-[4-(dimethylamino)piperidin-1-yl]-2-methoxyphenyl}pyrimidin-2-amine; and 4-{6-[4-(benzyloxy)-3-methoxyphenyl]imidazo[2,1-b][1,3]thiazol-5-yl}-N-{3-[2-(dimethylamino)ethyl]phenyl}pyrimidin-2-amine;

or pharmaceutically acceptable salts or solvates thereof.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It will be appreciated that two or more asymmetric centers may be present in the present compounds, hence several diastereomers and enantiomers of the exemplified structures will often be possible. It is intended that pure diasteromers, pure enantiomers, and mixtures thereof, are within the scope of the invention.

Various stereoisomers (including enantiomers and diastereomers) and mixtures thereof (including racemates) are contemplated. Individual stereoisomers of present compounds may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed herein may exist as individual tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

Though structural representations or names of the compounds within this specification may show only one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within the naming of the compounds or drawings.

The present compounds can exist in radiolabeled or isotope labeled form containing one or more atoms having an atomic mass or mass number different from the atomic mass or mass number most abundantly found in nature. Isotopes of atoms such as hydrogen, carbon, phosphorous, sulfur, fluorine, chlorine, and iodine include, but are not limited to $^{2}H$, $^{3}H$, $^{14}C$, $^{32}P$, $^{35}S$, $^{18}F$, $^{36}Cl$, and $^{125}I$. Compounds that contain other radioisotopes of these and/or other atoms are within the scope of this invention. In one embodiment, the isotope-labeled compounds contain deuterium ($^{2}H$), tritium ($^{3}H$) or $^{14}C$ radioisotopes. Isotope and radiolabeled compounds of this invention can be prepared by the general methods well known to persons having ordinary skill in the art. Such isotope and radiolabeled compounds can be conveniently prepared by carrying out the procedures disclosed in the above Examples and Schemes by substituting a readily available isotope or radiolabeled reagent for a non-labeled reagent. The isotope and radiolabeled compounds of the invention may be used as standards to determine the effectiveness of IGF-IR ligands or modulators in the binding assays. The isotope and radiolabeled compounds of the invention or pharmaceutically acceptable salts or sovates thereof may also be used for treating or preventing diseases or conditions described herein.

c. Biological Data

The following example describes the assay that may be used to identify compounds having kinase activity.

IGF-1R kinase activity was assayed by a homogenous time-resolved fluorescence (HTRF) in vitro kinase assay (Mathis, G., HTRF(R) Technology. J Biomol Screen, 1999. 4(6): p. 309-314). Specifically, 10 µL C-terminal GST-tagged, recombinant, human IGF-1R, amino acids 954-1367 expressed by baculovirus in Sf21 cells (Cell Singaling Technology) was mixed with 10 µL inhibitor (various concentrations, 2% final DMSO) and 10 µL of ATP (50 µM final concentration) in reaction buffer (50 mM HEPES, pH 7.5, mM MgCl₂, 2 mM MnCl₂, 0.1% BSA and 1 mM DTT, 40 µL final volume). The reaction was initiated by addition of 10 µL of biotinylated peptide substrate (Biotin-Ahx-AEEEYF-FLFA, 0.5 µM final concentration) in a black 384-well plate (Packard). After 60 minutes incubation at room temperature, the reaction was quenched by addition of 60 μL stop/revelation buffer to give 30 mM EDTA, 1 μg/mL streptavidin-APC (Prozyme), 50 ng/mL anti-phosphotyrosine mAb PT66-K Europium Cryptate, 30 mM HEPES, pH 7.5, 120 mM KF, 0.005% Tween-20, 0.05% BSA). The quenched reaction was allowed to stand at room temperature for 1 hour and then read in a time-resolved fluorescence detector (Envision, Perkin Elmer) at 615 nm and 665 nm simultaneously. The ratio between the signal of 615 nm and 665 nm was used in the calculation of the $IC_{50}$.

Table 1 demonstrates the utility of the representative examples of compounds described herein as inhibitors of IGF-1R kinases. In Table 1, "A" represents $IC_{50}$ of less than 25 nM; "B" represents $IC_{50}$ of between 25 nM and 100 nM; "C" represents $IC_{50}$ of between 101 nM and 500 nM; "D" represents $IC_{50}$ of between 501 nM and 1 μM; and "E" represents $IC_{50}$ of greater than 1 μM.

TABLE 1

| Example # | $IC_{50}$ |
|---|---|
| 1 | A |
| 2 | C |
| 3 | E |
| 4 | E |
| 5 | E |
| 6 | E |
| 7 | E |
| 8 | B |
| 9 | B |
| 10 | C |
| 11 | C |
| 12 | C |
| 13 | C |
| 14 | E |
| 15 | E |
| 16 | C |
| 17 | C |
| 18 | C |
| 19 | C |
| 20 | C |
| 21 | C |
| 22 | E |
| 23 | B |
| 24 | B |
| 25 | C |
| 26 | C |
| 27 | C |
| 28 | E |
| 29 | E |
| 30 | A |
| 31 | C |
| 32 | C |
| 33 | B |
| 34 | B |
| 35 | C |
| 36 | A |
| 37 | C |
| 38 | B |
| 39 | C |
| 40 | E |
| 41 | E |
| 42 | C |
| 43 | C |
| 44 | B |
| 45 | C |
| 46 | B |
| 47 | B |
| 48 | C |
| 49 | E |
| 50 | E |
| 51 | D |
| 52 | C |
| 53 | C |
| 54 | C |
| 55 | B |
| 56 | C |
| 57 | A |
| 58 | E |
| 59 | B |
| 60 | B |
| 61 | A |
| 62 | B |
| 63 | B |
| 64 | C |
| 65 | B |
| 66 | B |
| 67 | C |
| 68 | D |
| 69 | A |
| 70 | B |
| 71 | A |
| 72 | A |
| 73 | C |
| 74 | A |
| 75 | A |
| 76 | A |
| 77 | E |
| 78 | E |
| 79 | E |
| 80 | B |
| 81 | B |
| 82 | E |
| 83 | B |
| 84 | A |
| 85 | B |

Compounds assessed by the above-described assay were found to have IGF-1R inhibiting activity.

d. Methods of Using the Compounds

In one aspect, the present invention provides methods of using one or more compounds or composition described herein to treat or prevent a disease or condition involving mediation, overexpression or disregulation of IGF-1R kinases in a mammal. In particular, compounds described herein are expected to have utility in treatment of diseases or conditions during which protein kinases such as IGF-1R kinase family members are expressed.

In one group of embodiments, diseases and conditions of humans or other animals that can be treated with inhibitors of IGF-1R kinases, include, but are not limited to, diseases involving overexpression or unregulation of a protein kinase family member such as but not limited to cancer. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds described herein would be useful in treating pediatric cancers or neoplasms including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Involvement of IGF and IGFR in cancer is reported in Nature Reviews Cancer 8, 915 (2008).

The methods of the present invention typically involve administering to a subject in need of therapeutic treatment therapeutically effective amounts of one or more compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

e. Combination Therapy

Further provided herein are methods of using one or more compounds or composition of the invention in combination with one or more additional active agents. Compounds described herein are expected to be useful when used with:

alkylating agents, angiogenesis inhibitors, antibodies, antimetabolites, antimitotics, antiproliferatives, aurora kinase inhibitors, other apoptosis promoters (for example, Bcl-xL, Bcl-w and Bfl-1) inhibitors, Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, DVD Ig's, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAP's) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteosome inhibitors, purine analogs, pyrimidine analogs, receptor tyrosine kinase inhibitors, retinoids/deltoids plant alkaloids, small inhibitory ribonucleic acids (siRNA's), topoisomerase inhibitors, combinations thereof and the like.

A BiTE antibody is a bi-specific antibody that directs T-cells to attach cancer cells by simultaneously binding the two cells. The T-cell then attacks the target cancer cell. Exemplary BiTE antibodies include adecatumumab (Micromet MT201), blinatumomab (Micromet MT103) and the like.

SiRNA's are molecules having endogenous RNA bases or chemically modified nucleotides. The modifications shall not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides or a combination thereof. The siRNA can have varying lengths (10-200 bps) and structures (hairpins, single/double strands, bulges, nicks/gaps, mismatches) and processed in the cell to provide active gene silencing. In certain embodiments, a double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. The multivalent binding protein is preferably engineered to have the three or more antigen binding sites and is generally not a naturally occurring antibody. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific, i.e., capable of binding one antigen or multispecific, i.e., capable of binding two or more antigens. DVD binding proteins comprising two heavy chain DVD polypeptides and two light chain DVD polypeptides are referred to as DVD Ig. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORE- TAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (metrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Bcl-2 proteins inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like. HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of apoptosis proteins include ApoMab (a fully human affinity-matured IgG1 monoclonal antibody), antibodies that target TRAIL or death receptors (e.g., pro-apoptotic receptor agonists DR4 and DR5), conatumumab, ETR2-ST01, GDC0145, (lexatumumab), HGS-1029, LBY-135, PRO-1762 and tratuzumab.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like. Platinum chemotherapeutics include cisplatin, ELOXATIN® (oxaliplatin) eptaplatin, lobaplatin, nedaplatin, PARAPLATIN® (carboplatin), satraplatin and the like. Polo-like kinase inhibitors include BI-2536 and the like.

Thrombospondin analogs include ABT-510, ABT-567, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofuran, picibanil PF-3512676 (CpG-8954), ubenimex and the like. Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Compounds described herein can also be used as radiosensitiseser that enhance the efficacy of radiotherapy. Examples of radiotherapy include external beam radiotherapy, teletherapy, brachtherapy and sealed, unsealed source radiotherapy and the like.

Additionally, compounds described herein may be combined with other chemptherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); 0: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Combination therapy includes administration of a single pharmaceutical dosage formulation containing one or more of the compounds and one or more additional pharmaceutical agents, as well as administration of the compounds and each additional pharmaceutical agent in its own separate pharmaceutical dosage formulation. For example, one or more active ingredients (including present compounds and additional pharmaceutical agents) may be administered to the patient together, in a single oral dosage composition having a fixed ratio of each active ingredient, such as a tablet or capsule; or each active ingredient may be administered in separate oral dosage formulations.

Separate dosage formulations may be administered at essentially the same time (e.g., concurrently) or at separately staggered times (e.g., sequentially).

f. Pharmaceutical Compositions

Pharmaceutical compositions comprising compounds described herein or pharmaceutically acceptable salts or solvates thereof are also provided. The pharmaceutical compositions comprise compounds of interest formulated together with one or more non-toxic pharmaceutically acceptable carriers.

Another aspect relates to pharmaceutical compositions comprising compounds described herein, or pharmaceutically acceptable salts or solvates thereof, and one or more pharmaceutically acceptable carriers, alone or in combination with one or more additional active agents.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

This invention also is directed, in part, to all salts of the compounds described herein. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient, the salt preferably is pharmaceutically acceptable and/or physiologically compatible. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

g. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $G^1$, $Ar^1$, $Ar^2$, $R^1$, $R^2$, $R^3$, $R^4$, $R^5$, m, m', m", n, p, and q, have meanings as set forth in the summary section unless otherwise noted, can be synthesized as shown in Schemes 1-3.

Abbreviations which have been used in the descriptions of the Schemes and the Examples that follow are: DMF for N,N-dimethylformamide, and DMSO for dimethyl sulfoxide.

Compounds of formula (I-i) can be prepared as illustrated in Scheme 1.

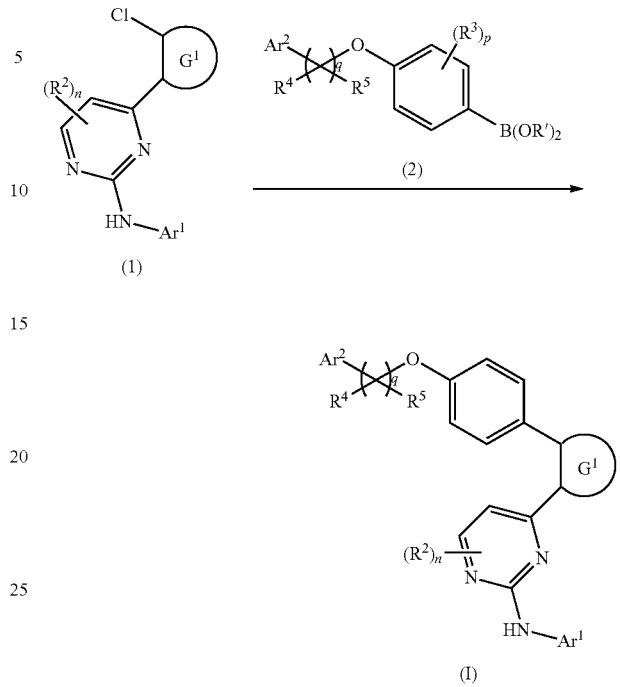

Scheme 1

Compounds of formula (I) may be prepared by reacting compounds of formula (1) with an appropriate boronic acids of formula (2) wherein R' is H, or an appropriate boronic esters of formula (2) wherein R' is alkyl. The reaction can be carried out in the presence of a palladium (0) source, a base, and a suitable solvent. Suitable source of palladium (0) includes, but are not limited to, tetrakis(triphenylphosphine) palladium(0). Typical bases for use in the reaction include, for example, cesium carbonate and cesium fluoride. Lower alcohol such as methanol, toluene, 1,2-dimethoxyethane, and mixtures thereof are examples of suitable solvent. The foregoing processes for converting the chloro substituent to the ether group is described as occurring at the end of the synthesis, however, one skilled in the art will readily appreciate that the conversion can occur at earlier stages. The various permutations of the synthesis described herein wherein the conversion of the chloro substituent to the ether occurs earlier in the synthesis are contemplated by the instant invention and encompassed within its scope.

Intermediates of formula (1) wherein $G^1$ is formula (i) used in the foregoing step can be prepared as shown using general procedures as shown in Scheme 2.

Scheme 2

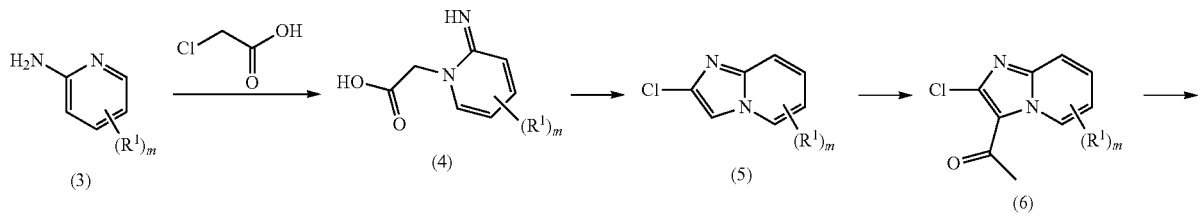

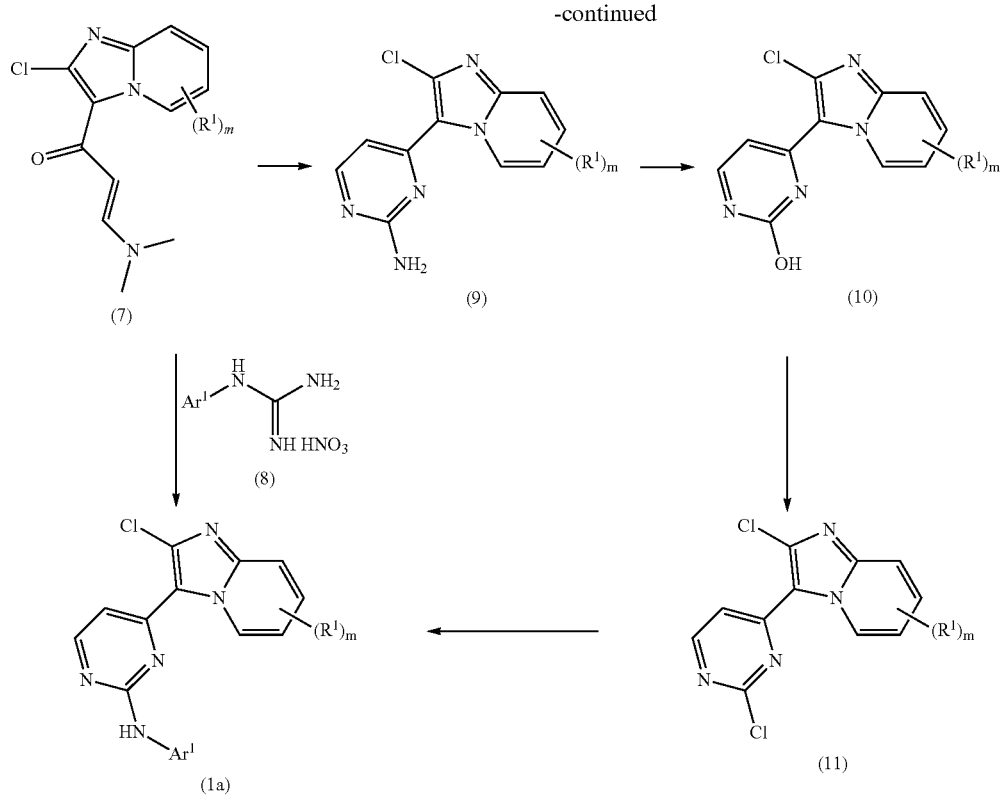

Compounds of formula (4) can be prepared by treating amines (3) with chloroacetic acid and a base, in a suitable solvent. Examples of suitable bases include but are not limited to, tertiary amines such as triethylamine and diisopropylethyl amine. Water is an example of a suitable solvent.

Treatment of (4) with phosphorusoxychloride at elevated temperature and in a suitable solvent (e.g. toluene) provides compounds of formula (5).

Compounds of formula (6) may be prepared from compounds of formula (5) using an acylating procedure. Typically the acylation is conducted by treating (5) with an acylating agent, optionally in the presence of an acid or Lewis acid catalyst and optionally in a suitable solvent with optional heating. Typical acylating agents will be readily determined by those skilled in the art. One particular acylating agent is acetic anhydride. Typical acid for use in this reaction is sulfuric acid.

Compounds of formula (7) may be prepared by reacting compounds of formula (6) with a dimethylformamide dialkyl acetal of formula $(CH_3)_2NCH(OR^{101})_2$ wherein $R^{101}$ is alkyl or cycloalkyl. Typical dimethylformamide dialkyl acetal for use in this method include but are not limited to dimethylformamide dimethylacetal and dimethylformamide di-tert-butyl acetal. The reaction is carried out by mixing compounds of formula (6) with the dimethylformamide dialkyl acetal, optionally with heating. Typical solvent includes but is not limited to N-methyl 2-pyrrolidinone.

Mixing compounds of formula (7) with amidines of formula (8) in a suitable solvent, optionally in the presence of a base (particularly when the amidine is in a salt form), and heating the reaction mixture to about 50° C.-150° C., afford compounds of formula (1). Typical solvents include lower alcohols such as methanol, ethanol, isopropanol, dimethylformamide and the like. The base is typically sodium alkoxide, potassium carbonate, or an amine base such as triethylamine.

Alternatively, the conversion of compounds of formula (7) to intermediates (1a) may be carried out by: (a) treating (7) with guanidine hydrochloride and a base as described in the preceding paragraph to obtain compounds of formula (9), (b) treaing amines (9) with sodium nitrite in acetic acid and water to provide compounds of formula (10), (c) treaing (10) with phosphorusoxy chloride at elevated temperature to provide chloro compounds of formula (11), and (d) treating compounds of formula (11) with an appropriate amines of formula $Ar^1NH_2$ in the presence of an acid such as but not limited to HCl, and a suitable solvent at elevated temperature. Examples of suitable solvent include but are not limited to lower alcohols such as 2-propanol.

Alternatively, (11) may be converted to (1a) in the presence of a suitable base at elevated temperature. Examples of suitable bases include but not limited to tertiary amines such as diiethylisopropyl amine.

Conversion of (11) to (1a) may also be accomplished by metal catalysed cross coupling reaction conditions known to those skilled in the art, for example, by utilizing a palladium catalyst and a suitable ligand (e.g. palladium (II) acetate and Xantphos) to facilitate the reaction.

Compounds of general formula (I) wherein $G^1$ is formula (ii) or (iii) can be prepared as shown in Scheme 3.

Scheme 3

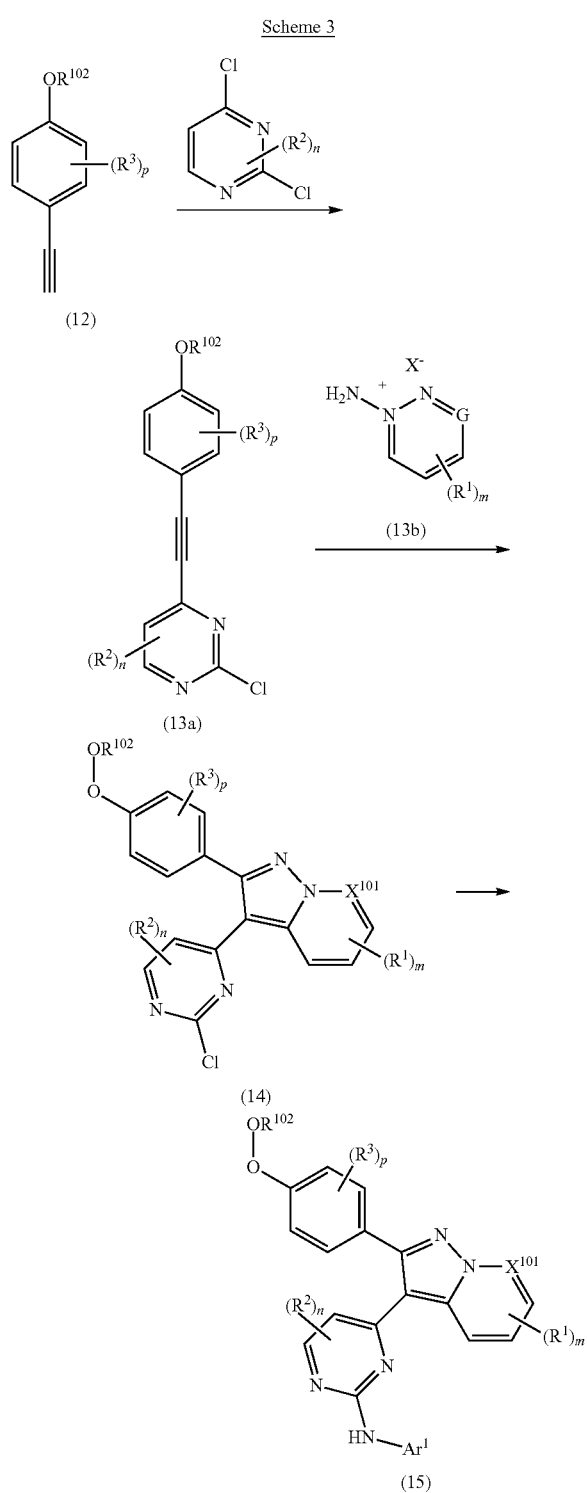

Alkynes of formula (12) wherein $R^{102}$ is —$(CR^4R^5)_q Ar^2$ can be treated with 2,4-dichloropyrimidine using coupling reaction conditions known to one skilled in the art, to provide compounds of formula (13a). Typically, the reaction can be conducted in the presence of a palladium source (e.g. bis (triphenylphosphine)palladium (II) dichloride), a Cu(I) co-catalyst such as but not limited to copper (I) iodide, and a base such as but not limited to trimethylamine, at elevated temperature (e.g. about 45° C. to about 150° C.), in a suitable solvent (e.g. tetrahydrofuran, DMF, toluene, and the like).

Treatment of (13a) with (13b) wherein X is ioidide or bromide in a suitable solvent such as but not limited to DMSO and in the presence of a suitable base, provide compounds of formula (14) wherein $R^{102}$ is as defined above and $X^{101}$ is C or N. Suitable bases include but are not limited to sodium or potassium hydroxide, sodium or potassium carbonate.

Treatment of compounds of formula (14) with suitable amines of formula $Ar^1NH_2$ in the presence of an acid such as but not limited to HCl, and a suitable solvent at elevated temperature affords compounds of formula (15). The reaction may also be facilitated by microwave irradiation. Typical solvents include lower alcohols such as methanol, ethanol, isopropanol, dimethylformamide and the like. Other conditions, for example, conditons that are described in Scheme 2, for the conversion of (14) to (15) are also known to those skilled in the art.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

h. EXAMPLES

Example 1

4-{2-[4-(benzyloxy)phenyl]imidazo[1,2-a]pyridin-3-yl}-N-{3-[2-(dimethylamino)ethyl]phenyl}pyrimidin-2-amine The title compound was prepared as described in EXAMPLE 12K substituting 4-(benzyloxy)phenylboronic acid for 4-(benzyloxy)-3-methoxyphenylboronic acid. MS (ESI(+)) m/e 541.3 (M+H)$^+$; $^1$H NMR (500 MHz, dimethylsulfoxide-d$_6$) δ ppm 9.69 (s, 1 H) 9.57 (d, 1 H) 8.33 (d, 1 H) 7.73 (d, 1 H) 7.64 (s, 1 H) 7.59 (m, 3 H) 7.48 (m, 3 H) 7.42 (t, 2 H) 7.35 (t, 1 H) 7.20 (t, 1 H) 7.11 (m, 2 H) 7.05 (t, 1 H) 6.85 (d, 1 H) 6.62 (d, 1 H) 5.16 (s, 2 H) 2.67 (m, 2 H) 2.45 (m, 2 H) 2.16 (s, 6 H).

Example 2

4-{2-[4-(benzyloxy)phenyl]imidazo[1,2-a]pyridin-3-yl}-N-(2-methoxy-4-morpholin-4-ylphenyl)pyrimidin-2-amine

Example 2A 4-(2-chloroimidazo[1,2-a]pyridin-3-yl)-N-(2-methoxy-4-morpholin-4-ylphenyl)pyrimidin-2-amine The trifluoroacetic acid salt of the title compound was prepared as described in EXAMPLE 12J, substituting 2-methoxy-4-morpholinoaniline for EXAMPLE 12I. MS (ESI(+)) m/e 437.0 (M+H)$^+$.

Example 2B

4-{2-[4-(benzyloxy)phenyl]imidazo[1,2-a]pyridin-3-yl}-N-(2-methoxy-4-morpholin-4-ylphenyl)pyrimidin-2-amine The title compound was prepared as described in EXAMPLE 12K, substituting EXAMPLE 2A for EXAMPLE 12J and 4-(benzyloxy)-phenylboronic acid for 4-(benzyloxy)-3-methoxyphenylboronic acid. MS (ESI(+)) m/e 585.3 (M+H)$^+$; $^1$H NMR (300 MHz, dimethylsulfoxide-d$_6$) δ ppm 9.53 (bds, 1 H) 8.22 (d, 1 H), 7.79 (d, 1 H), 7.67 (m, 1H), 7.58 (d, 2H), 7.50 (m, 2H), 7.38 (m, 5H), 7.16 (m, 3H), 6.72 (d, 1H), 6.54 (dd, 1H), 6.51 (d, 1H), 5.18 (s, 2H), 3.82 (s, 3H), 3.76 (m, 4H), 3.15 (m, 4H).

Example 3

4-{2-[4-(benzyloxy)phenyl]imidazo[1,2-a]pyridin-3-yl}-N-(2-methoxyphenyl)pyrimidin-2-amine

Example 3A 4-(2-chloroimidazo[1,2-a]pyridin-3-yl)-N-(2-methoxyphenyl)pyrimidin-2-amine The title compound was prepared as described in EXAMPLE 12J, substituting 2-methoxyaniline for EXAMPLE 12I. MS (ESI(+)) m/e 351.0 (M+H)$^+$.

Example 3B

4-{2-[4-(benzyloxy)phenyl]imidazo[1,2-a]pyridin-3-yl}-N-(2-methoxyphenyl)pyrimidin-2-amine The title compound was prepared as described in EXAMPLE 12K, substituting EXAMPLE 3A for EXAMPLE 12J and 4-(benzyloxy)-phenylboronic acid for 4-(benzyloxy)-3-methoxyphenylboronic acid. MS (ESI(+)) m/e 500.1 (M+H)$^+$; $^1$H NMR (300 MHz, dimethylsulfoxide-d$_6$) δ ppm 9.44 (d, 1H), 8.52 (s, 1H), 8.29 (d, 1H), 7.87 (d, 1H), 7.71 (d, 1H), 7.57 (d, 2H), 7.48-7.35 (m, 6H), 7.12 (m, 4H), 6.98 (m, 2H), 6.59 (d, 1H), 5.16 (s, 2H), 3.86 (s, 3H).

Example 4

4-{2-[4-(benzyloxy)phenyl]imidazo[1,2-a]pyridin-3-yl}-N-[3-(methylsulfonyl)phenyl]pyrimidin-2-amine

Example 4A 4-(2-chloroimidazo[1,2-a]pyridin-3-yl)-N-[3-(methylsulfonyl)phenyl]pyrimidin-2-amine The title compound was prepared as described in EXAMPLE 12J, substituting 3-methylsulfonylaniline for EXAMPLE 12I. MS (ESI(+)) m/e 399.0 (M+H)$^+$.

Example 4B

4-{2-[4-(benzyloxy)phenyl]imidazo[1,2-a]pyridin-3-yl}-N-[3-(methylsulfonyl)phenyl]pyrimidin-2-amine The trifluoroacetic acid salt of the title compound was prepared as described in EXAMPLE 12K, substituting EXAMPLE 4A for EXAMPLE 12J and 4-(benzyloxy)-phenylboronic acid for 4-(benzyloxy)-3-methoxyphenylboronic acid. MS (ESI(+)) m/e 548.2 (M+H)$^+$; $^1$H NMR (300 MHz, dimethylsulfoxide-d$_6$) δ ppm 10.19 (s, 1H), 9.61 (d, 1H), 8.44 (d, 1H), 8.38 (m, 1H), 8.09 (d, 1H), 7.80 (d, 1H), 7.61 (d, 2H), 7.59-7.32 (m, 8H), 7.19 (m, 1H), 7.14 (d, 2H), 6.73 (d, 1H), 5.18 (s, 2H), 3.18 (s, 3H).

Example 5

3-[(4-{2-[4-(benzyloxy)phenyl]imidazo[1,2-a]pyridin-3-yl}pyrimidin-2-yl)amino]-N,N-dimethylbenzenesulfonamide

Example 5A 3-(4-(2-chloroimidazo[1,2-a]pyridin-3-yl)pyrimidin-2-ylamino)-N,N-dimethylbenzenesulfonamide The title compound was prepared as described in EXAMPLE 12J, substituting 3-amino-N,N-dimethylbenzenesulfonamide for EXAMPLE 12I. MS (ESI(+)) m/e 429.0 (M+H)$^+$.

Example 5B

3-[(4-{2-[4-(benzyloxy)phenyl]imidazo[1,2-a]pyridin-3-yl}pyrimidin-2-yl)amino]-N,N-dimethylbenzenesulfonamide The trifluoroacetic acid salt of the title compound was prepared as described in EXAMPLE 12K, substituting EXAMPLE 5A for EXAMPLE 12J and 4-(benzyloxy)-phenylboronic acid for 4-(benzyloxy)-3-methoxyphenylboronic acid. MS (ESI(+)) m/e 577.2 (M+H)$^+$; $^1$H NMR (300 MHz, dimethylsulfoxide-$d_6$) δ ppm 10.14 (s, 1H), 9.57 (d, 1H), 8.40 (d, 1H), 8.21 (m, 1H), 8.13 (m, 1H), 7.74 (d, 1H), 7.63-7.30 (m, 10H), 7.13 (m, 3H), 6.71 (d, 1H), 5.17 (s, 2H), 2.61 (s, 6H).

Example 6

4-{2-[4-(benzyloxy)phenyl]imidazo[1,2-a]pyridin-3-yl}-N-[4-(methylsulfonyl)phenyl]pyrimidin-2-amine

Example 6A 4-(2-chloroimidazo[1,2-a]pyridin-3-yl)-N-[4-(methylsulfonyl)phenyl]pyrimidin-2-amine The title compound was prepared as described in EXAMPLE 12J, substituting 4-methylsulfonylaniline for EXAMPLE 12I. MS (ESI(+)) m/e 399.0 (M+H)$^+$.

Example 6B

4-{2-[4-(benzyloxy)phenyl]imidazo[1,2-a]pyridin-3-yl}-N-[4-(methylsulfonyl)phenyl]pyrimidin-2-amine The trifluoroacetic acid salt of the title compound was prepared as described in EXAMPLE 12K, substituting EXAMPLE 6A for EXAMPLE 12J and 4-(benzyloxy)-phenylboronic acid for 4-(benzyloxy)-3-methoxyphenylboronic acid. MS (ESI(+)) m/e 548.2 (M+H)$^+$; $^1$H NMR (300 MHz, dimethylsulfoxide-$d_6$) δ ppm 10.35 (s, 1H), 9.60 (d, 1H), 8.50 (d, 1H), 8.00 (d, 2H), 7.85-7.81 (m, 3H), 7.69-7.59 (m, 3H), 7.51-7.35 (m, 5H), 7.27 (m, 1H), 7.15 (d, 2H), 6.80 (d, 1H), 5.18 (s, 2H), 3.16 (s, 3H).

Example 7

4-{2-[4-(benzyloxy)phenyl]imidazo[1,2-a]pyridin-3-yl}-N-phenylpyrimidin-2-amine

Example 7A 4-(2-chloroimidazo[1,2-a]pyridin-3-yl)-N-phenylpyrimidin-2-amine

The title compound was prepared as described in EXAMPLE 12J substituting aniline for EXAMPLE 12I. MS (ESI(+)) m/e 321.9 (M+H)$^+$.

Example 7B

4-{2-[4-(benzyloxy)phenyl]imidazo[1,2-a]pyridin-3-yl}-N-phenylpyrimidin-2-amine

The title compound was prepared as described in EXAMPLE 12K substituting EXAMPLE 7A for EXAMPLE 12J and 4-(benzyloxy)phenylboronic acid for 4-(benzyloxy)-3-methoxyphenylboronic acid. MS (ESI(+)) m/e 470.1 (M+H)$^+$; $^1$H NMR (500 MHz, dimethylsulfoxide-$d_6$) δ ppm 9.75 (s, 1 H) 9.57 (d, 1 H) 8.35 (d, 1 H) 7.75 (m, 3 H) 7.59 (d, 2 H) 7.48 (m, 3 H) 7.42 (t, 2 H) 7.35 (t, 1 H) 7.30 (t, 2 H) 7.12 (d, 2 H) 7.06 (t, 1 H) 6.99 (t, 1 H) 6.64 (d, 1 H) 5.16 (s, 2 H).

Example 8

4-{2-[4-(benzyloxy)-2-fluorophenyl]imidazo[1,2-a]pyridin-3-yl}-N-{3-[2-(dimethylamino)ethyl]phenyl}pyrimidin-2-amine The trifluoroacetic acid salt of the title compound was prepared as described in EXAMPLE 12K substituting 4-(benzyloxy)-2-fluorophenylboronic acid for 4-(benzyloxy)-3-methoxyphenylboronic acid. MS (ESI(+)) m/e 559.3 (M+H)$^+$; $^1$H NMR (300 MHz, dimethylsulfoxide-$d_6$) δ ppm 2.83 (d, 6 H) 2.94 (m, 2 H) 3.30 (m, 2 H) 5.20 (s, 2 H) 6.51 (d, 1 H) 6.92 (m, 1 H) 7.04 (m, 1 H) 7.14 (m, 1 H) 7.30 (t, 1 H) 7.37-7.64 (m, 8 H) 7.70 (m, 1 H) 7.78 (m, 1 H) 8.34 (d, 1 H) 9.34 (brs, 1 H) 9.77 (m, 2 H).

Example 9

4-{2-[4-(benzyloxy)-3-fluorophenyl]imidazo[1,2-a]pyridin-3-yl}-N-{3-[2-(dimethylamino)ethyl]phenyl}pyrimidin-2-amine The trifluoroacetic acid salt of the title compound was prepared as described in EXAMPLE 12K, substituting 4-(benzyloxy)-3-fluorophenylboronic acid for 4-(benzyloxy)-3-methoxyphenylboronic acid. MS (ESI(+)) m/e 559.3 (M+H)$^+$; $^1$H NMR (300 MHz, dimethylsulfoxide-$d_6$) δ ppm 2.82 (d, 6 H) 2.92 (m, 2 H) 3.28 (m, 2 H) 5.24 (s, 2 H) 6.70 (d, 1 H) 6.92 (m, 1 H) 7.11 (m, 1 H) 7.28 (t, 1 H) 7.33-7.56 (m, 9 H) 7.62 (m, 1 H) 7.71 (m, 1 H) 7.76 (m, 1 H) 8.40 (d, 1 H) 9.36 (brs, 1 H) 9.51 (d, 1 H) 9.81 (s, 1 H).

Example 10

4-{2-[4-(benzyloxy)-2-methylphenyl]imidazo[1,2-a]pyridin-3-yl}-N-{3-[2-(dimethylamino)ethyl]phenyl}pyrimidin-2-amine The trifluoroacetic acid salt of the title compound was prepared as described in EXAMPLE 12K substituting 4-(benzyloxy)-2-methylphenylboronic acid for 4-(benzyloxy)-3-methoxyphenylboronic acid. MS (ESI(+)) m/e 555.3 (M+H)$^+$; $^1$H NMR (300 MHz, dimethylsulfoxide-d$_6$) δ ppm 2.12 (s, 3 H) 2.84 (d, 6 H) 2.96 (m, 2 H) 3.30 (m, 2 H) 5.19 (s, 2 H) 6.28 (d, 1 H) 6.94 (m, 1 H) 7.00 (m, 1 H) 7.10 (m, 1 H) 7.23-7.52 (m, 8 H) 7.60-7.72 (m, 3 H) 7.85 (m, 1 H) 8.28 (d, 1 H) 9.43 (brs, 1 H) 9.78 (s, 1 H) 10.06 (d, 1 H).

Example 11

4-{2-[4-(benzyloxy)-3-chlorophenyl]imidazo[1,2-a]pyridin-3-yl}-N-{3-[2-(dimethylamino)ethyl]phenyl}pyrimidin-2-amine The trifluoroacetic acid salt of the title compound was prepared as described in EXAMPLE 12K, substituting 4-(benzyloxy)-3-chlorophenylboronic acid for 4-(benzyloxy)-3-methoxyphenylboronic acid. MS (ESI(+)) m/e 575.2 (M+H)$^+$; $^1$H NMR (300 MHz, dimethylsulfoxide-d$_6$) δ ppm 2.82 (d, 6 H) 2.92 (m, 2 H) 3.28 (m, 2 H) 5.27 (s, 2 H) 6.71 (d, 1 H) 6.92 (m, 1 H) 7.11 (m, 1 H) 7.28 (t, 1 H) 7.33-7.47 (m, 4 H) 7.50-7.63 (m, 5 H) 7.75 (m, 3 H) 8.41 (d, 1 H) 9.35 (brs, 1 H) 9.51 (d, 1 H) 9.81 (s, 1 H).

Example 12

4-{2-[4-(benzyloxy)-3-methoxyphenyl]imidazo[1,2-a]pyridin-3-yl}-N-{3-[2-(dimethylamino)ethyl]phenyl}pyrimidin-2-amine Example 12A 2-(2-iminopyridin-1(2H)-yl)acetic acid In a 100 mL round bottom flask, 2-chloroacetic acid (10 g, 106 mmol) in water (16.3 mL) was treated with triethylamine (16.67 mL, 120 mmol) dropwise over 6 minutes. After stirring the reaction at ambient temperature for 10 minutes, 2-aminopyridine (11.76 g, 125 mmol) was added and the mixture was heated at 90° C. for 5 hours. The reaction mixture was cooled to ambient temperature and diluted with ethanol (11 mL). The resulting suspension was stirred in an ice bath for 1 hour and filtered. The solid collected was washed with ~30 mL cold ethanol and dried under vacuum to constant weight to provide the title compound. MS (DCI(+)) m/e 152.9 (M+H)$^+$.

Example 12B 2-chloroimidazo[1,2-a]pyridine

To a 250 mL round bottom flask was charged EXAMPLE 12A (15.19 g, 100 mmol) and toluene (64 mL). The mixture was heated to 112° C. and POCl$_3$ (27.9 mL) was added dropwise over 15 minutes. The mixture became very thick with initial portions added. Upon complete addition, the suspension was stirred at 112° C. for 16 hours. The reaction was allowed to cool to ambient temperature and was added slowly to 320 mL of stirring cold (~5° C.) water over 15 minutes. After stirring vigorously for 30 minutes, the layers were separated in a separatory funnel. The aqueous layer was cooled in an ice bath and neutralized to pH 7 with 10% aqueous NaOH (~400 mL) with stirring. The resulting suspension was filtered, and the solid collected was dissolved in CH$_2$Cl$_2$ (300 mL) and dried over MgSO$_4$. The aqueous filtrate was extracted with CH$_2$Cl$_2$ (4×120 mL). The combined organic extracts were washed with brine and dried over MgSO$_4$. The two CH$_2$Cl$_2$ solutions drying over MgSO$_4$ were filtered, combined, and concentrated to provide the title compound. MS (DCI(+)) m/e 153.0 (M+H)$^+$ Example 12C To a 500 mL round bottom flask was charged EXAMPLE 12B (12.2 g, 80 mmol), acetic anhydride (320 mL), and sulfuric acid (0.852 mL, 16 mmol). The mixture was heated at 140° C. for 2 hours. The reaction was cooled to ambient temperature, poured into 400 mL cold water, and extracted with 2×400 mL CH$_2$Cl$_2$. The combined organic extracts were washed with 350 mL 1N NaOH and brine, dried over Na$_2$SO$_4$, filtered, and concentrated under high vacuum to provide the title compound. MS (ESI(+)) m/e 194.9 (M+H)$^+$ Example 12D (E)-1-(2-chloroimidazo[1,2-a]pyridin-3-yl)-3-(dimethylamino)prop-2-en-1-one In a 100 mL round bottom flask, a solution of EXAMPLE 12C (4.25 g, 21.84 mmol), 1,1-di-tert-butoxy-N,N-dimethylmethanamine (28.8 mL, 120 mmol), and N-methyl-2-pyrrolidinone (15 mL) was heated at 85° C. for 2 hours. The reaction was concentrated under high vacuum on a rotavap at 60° C. The residual solid was triturated with 5 mL diethyl ether, filtered and dried to provide the title compound. MS (ESI(+)) m/e 249.8 (M+H)$^+$.

Example 12E 4-(2-chloroimidazo[1,2-a]pyridin-3-yl)pyrimidin-2-amine

A 500 mL round bottom flask was charged EXAMPLE 12D (11.3 g, 45.3 mmol), guanidine carbonate (12.2 g, 67.9 mmol) and N-methyl-2-pyrrolidinone (140 mL) and the reaction mixture was heated at 92° C. for 72 hours. The reaction was allowed to cool to ambient temperature and was poured into 750 mL water. The resulting suspension was stirred 45 minutes and filtered. The collected solids were washed with water and air dried on the filter under vacuum overnight to provide the title compound. MS (DCI(+)) m/e 246.0 (M+H)$^+$.

Example 12F 4-(2-chloroimidazo[1,2-a]pyridin-3-yl)pyrimidin-2-ol

To a 500 mL round bottom flask was charged EXAMPLE 12E (9.95 g, 40.5 mmol) and acetic acid (167 mL). The suspension was heated at 85° C. until a homogeneous solution formed. The reaction was allowed to cool to 65° C. and a solution of sodium nitrite (8.38 g, 122 mmol) in water (26 mL) was added dropwise over 10 min. Upon complete addition, the solution was stirred at 65° C. for 35 minutes. The reaction mixture was cooled to ambient temperature and then further cooled in an ice bath at 0° C. The reaction was quenched to pH 6-7 with 3 N NaOH (~910 mL). The resulting cold suspension was filtered and the solid collected was washed with 3×400 mL water and 2×130 mL diethyl ether.

The solid was dried in a vacuum oven at 70° C. to provide the title compound. MS (ESI(+)) m/e 246.8 (M+H)+.

Example 12G 2-chloro-3-(2-chloropyrimidin-4-yl)imidazo[1,2-a]pyridine

To a 500 mL round bottom flask was charged EXAMPLE 12F (9.1 g, 36.9 mmol) and POCl$_3$ (86 mL, 922 mmol). The suspension was heated to 80° C. for 5 hours. The reaction was cooled to ambient temperature and the suspension was added slowly to 500 mL of vigorously stirring water in an ice bath via an addition funnel at such a rate that the internal temperature did not exceed 20° C. Upon complete addition, the suspension was stirred for 30 minutes and then was basified to pH 10 with 15% aqueous NaOH (1280 mL) added in a rapid dropwise manner at such a rate to keep the internal temperature below 20° C. Upon basification, suspension was stirred 30 minutes and filtered. The collected solid was washed with 4×400 mL water, and dried in a vacuum oven at 65° C. to provide the title compound. MS (ESI(+)) m/e 264.8 (M+H)+

Example 12H

N,N-dimethyl-2-(3-nitrophenyl)ethanamine

In a 250 mL round bottom flask was charged 1-(2-bromoethyl)-3-nitrobenzene (10 g, 43.5 mmol) and acetonitrile (36 mL). The suspension was treated with triethylamine (18.1 mL, 130 mmol) and dimethylamine (2 M in tetrahydrofuran, 65.2 mL, 130 mmol). The resulting mixture was stirred at ambient temperature for 48 hours. The mixture was concentrated. The residual solid was partitioned between ethyl acetate (130 mL) and 60 ml saturated aqueous sodium bicarbonate. The aqueous layer was washed with ethyl acetate (75 mL). The combined organic layers were washed with brine, dried over MgSO$_4$, filtered, and concentrated. The concentrate was purified by flash chromatography on an 80 g silica gel column using an AnaLogix IntelliFlash 280 system eluting with a gradient of from 0% to 7% methanol in CH$_2$Cl$_2$ to provide the title compound. MS (DCI(+)) m/e 195.1 (M+H)+.

Example 12I 3-(2-(dimethylamino)ethyl)aniline

In a 250 mL stainless steel pressure bottle, EXAMPLE 12H (5.02 g, 25.8 mmol) in methanol (70 mL) was treated with 5% Pd—C (wet, 1.40 g, 25.8 mmol) and the suspension was shaken under 30 psi of hydrogen for 1.3 hours at ambient temperature. The mixture was filtered through a nylon membrane and concentrated to provide the title compound. MS (DCI(+)) m/e 165.1 (M+H)+.

Example 12J 4-(2-chloroimidazo[1,2-a]pyridin-3-yl)-N-(3-(2-(dimethylamino)ethyl)phenyl)pyrimidin-2-amine A 20 mL reaction vial equipped with a stir bar was charged with EXAMPLE 12G (0.67 g, 2.53 mmol), EXAMPLE 12I (0.46 g, 2.80 mmol)), 4 M HCl in 1,4-dioxane (0.69 mL, 2.77 mmol) and 2-propanol (13 ml). The vessel was sealed and the mixture was heated on a thermal block at 120° C. for 3.5 hours. The reaction was cooled to ambient temperature and concentrated. The concentrate was dissolved in 50 mL 15% methanol/CH$_2$Cl$_2$ and washed with 15 mL saturated aqueous sodium carbonate and 15 mL brine. The organic layer was dried over Na$_2$SO$_4$ and concentrated. The concentrate was purified by flash chromatography on a 20 g silica gel column eluting with methanol in CH$_2$Cl$_2$ to provide the title compound. MS (ESI(+)) m/e 393.0 (M+H)+.

Example 12K

4-{2-[4-(benzyloxy)-3-methoxyphenyl]imidazo[1,2-a]pyridin-3-yl}-N-{3-[2-(dimethylamino)ethyl]phenyl}pyrimidin-2-amine A 2 mL Biotage microwave reaction vial was charged with EXAMPLE 12J (0.04 g, 0.102 mmol), 4-(benzyloxy)-3-methoxyphenylboronic acid (0.031 g, 0.120 mmol), cesium fluoride (0.046 g, 0.305 mmol), 1,2-dimethoxyethane (0.85 mL) and methanol (0.4 mL). The mixture was treated with tetrakis(triphenylphosphine)palladium (0) (5.9 mg, 0.005 mmol) and the vessel was sealed under nitrogen. The reaction was heated at 155° C. for 35 minutes in a Biotage Initiator microwave reactor. The reaction was cooled to ambient temperature, diluted with 5 mL water, and extracted with 20 mL 10% methanol/CH$_2$Cl$_2$. The organic phase was concentrated and the residue was purified by reverse-phase HPLC on a Phenomenex C18 column (3×15 cm, 10 µm particle size) eluting with a gradient of acetonitrile in 0.15% aqueous trifluoroacetic acid to provide the title compound as a trifluoroacetic acid salt. MS (ESI(+)) m/e 571.3 (M+H)+; $^1$H NMR (300 MHz, dimethylsulfoxide-d$_6$) δ ppm 2.82 (d, 6 H) 2.93 (m, 2 H) 3.29 (m, 2 H) 3.75 (s, 3 H) 5.15 (s, 2 H) 6.73 (d, 1 H) 6.92 (m, 1 H) 7.17 (m, 3 H) 7.28 (m, 2 H) 7.37-7.50 (m, 5 H) 7.59 (m, 2 H) 7.70 (m, 1 H) 7.79 (m, 1 H) 8.40 (d, 1 H) 9.37 (brs, 1 H) 9.60 (d, 1 H) 9.80 (s, 1 H).

Example 13

4-{2-[4-(benzyloxy)phenyl]imidazo[1,2-a]pyridin-3-yl}-N-{2-methoxy-4-[4-(4-methylpiperazin-1-yl)piperidin-1-yl]phenyl}pyrimidin-2-amine Example 13A 1-(1-(3-methoxy-4-nitrophenyl)piperidin-4-yl)-4-methylpiperazine Into a 5 mL microwave tube was charged 4-fluoro-2-methoxy-1-nitrobenzene (0.1 g, 0.584 mmol), 1-methyl-4-(piperidin-4-yl)piperazine (0.321 g, 1.753 mmol), triethylamine (0.244 ml, 1.753 mmol), and acetonitrile (1.948 ml). The reaction was heated in Biotage microwave reactor at 130° C. for 40 minutes. The solvent was removed under reduced pressure, and the reaction purified by flash chromatography using a gradient 100% CH$_2$Cl$_2$ to 1:1 CH$_2$Cl$_2$/methanol to provide the title compound. MS (ESI) m/e 335 (M+H)+.

Example 13B 2-methoxy-4-(4-(4-methylpiperazin-1-yl)piperidin-1-yl)aniline

EXAMPLE 13A (1.16 g, 3.47 mmol) and methanol (20 ml) were added to 5% Pd—C, wet (0.232 g, 2.180 mmol) in a 250 mL stainless steel pressure bottle and stirred for 2 hours under H$_2$ at 30 psi at room temperature. The mixture was filtered through a nylon membrane and concentrated to provide the title compound. MS (ESI) m/e 305 (M+H)+.

Example 13C 4-(2-chloroimidazo[1,2-a]pyridin-3-yl)-N-(2-methoxy-4-(4-(4-methylpiperazin-1-yl)piperidin-1-yl)phenyl)pyrimidin-2-amine The title compound was prepared as described in EXAMPLE 12J, substituting EXAMPLE 13B for EXAMPLE 12I. MS (ESI) m/e 533 (M+H)+.

Example 13D

4-{2-[4-(benzyloxy)phenyl]imidazo[1,2-a]pyridin-3-yl}-N-{2-methoxy-4-[4-(4-methylpiperazin-1-yl)piperidin-1-yl]phenyl}pyrimidin-2-amine The title compound was prepared as described in EXAMPLE 12K, substituting EXAMPLE 13C for EXAMPLE 12J and 4-(benzyloxy)phenylboronic acid for 4-(benzyloxy)-3-methoxyphenylboronic acid. MS (ESI) m/e 681 (M+H)+; $^1$H NMR (300 MHz, dimethylsulfoxide-$d_6$) δ 9.41 (d, 1H), 8.41 (s, 1H), 8.19 (d, 1H), 7.67 (m, 1H), 7.54 (d, 2H), 7.49 (m, 2H), 7.32-7.45 (m, 5H), 7.10 (d, 2H), 6.93 (m, 1H), 6.68 (d, 1H), 6.50 (dd, 1H), 6.47 (d, 1H), 5.16 (s, 2H), 3.80 (s, 3H), 3.74 (d, 2H), 2.68 (t, 2H), 2.31 (m, 5H), 2.14 (s, 3H), 1.86 (m, 2H), 1.52 (m, 2H).

Example 14

4-{2-[4-(benzyloxy)phenyl]imidazo[1,2-a]pyridin-3-yl}-N-(5-methyl-1H-pyrazol-3-yl)pyrimidin-2-amine

Example 14A 4-(2-chloroimidazo[1,2-a]pyridin-3-yl)-N-(5-methyl-1H-pyrazol-3-yl)pyrimidin-2-amine The title compound was prepared as described in EXAMPLE 12J, substituting 5-methyl-1H-pyrazol-3-amine for EXAMPLE 12I. MS (ESI(+)) m/e 325.9 (M+H)+.

Example 14B

4-{2-[4-(benzyloxy)phenyl]imidazo[1,2-a]pyridin-3-yl}-N-(5-methyl-1H-pyrazol-3-yl)pyrimidin-2-amine The trifluoroacetic acid salt of the title compound was prepared as described in EXAMPLE 12K, substituting EXAMPLE 14A for EXAMPLE 12J and 4-(benzyloxy)-phenylboronic acid for 4-(benzyloxy)-3-methoxyphenylboronic acid. MS (ESI(+)) m/e 474.1 (M+H)+; $^1$H NMR (300 MHz, dimethylsulfoxide-$d_6$) δ ppm 10.20 (bds, 1H), 9.98 (d, 1H), 8.31 (d, 1H), 7.80 (d, 1H), 7.67 (m, 1H), 7.60 (d, 2H), 7.53-7.32 (m, 5H), 7.24 (m, 1H), 7.16 (d, 2H), 6.60 (d, 1H), 6.20 (s, 1H), 5.19 (s, 2H), 2.24 (s, 3H).

Example 15

4-{2-[4-(benzyloxy)phenyl]imidazo[1,2-a]pyridin-3-yl}-N-(3-cyclopropyl-1H-pyrazol-5-yl)pyrimidin-2-amine

Example 15A 4-(2-chloroimidazo[1,2-a]pyridin-3-yl)-N-(3-cyclopropyl-1H-pyrazol-5-yl)pyrimidin-2-amine The title compound was prepared as described in EXAMPLE 12J, substituting 3-cyclopropyl-1H-pyrazol-5-amine for EXAMPLE 12I. MS (ESI(+)) m/e 351.9 (M+H)+.

Example 15B

4-{2-[4-(benzyloxy)phenyl]imidazo[1,2-a]pyridin-3-yl}-N-(3-cyclopropyl-1H-pyrazol-5-yl)pyrimidin-2-amine The trifluoroacetic acid salt of the title compound was prepared as described in EXAMPLE 12K, substituting EXAMPLE 15A for EXAMPLE 12J and 4-(benzyloxy)-phenylboronic acid for 4-(benzyloxy)-3-methoxyphenylboronic acid. MS (ESI(+)) m/e 500.2 (M+H)+; $^1$H NMR (300 MHz, dimethylsulfoxide-$d_6$) δ ppm 10.04 (bds, 1H), 9.90 (d, 1H), 8.30 (d, 1H), 7.79 (d, 1H), 7.62 (m, 1H), 7.59 (d, 2H), 7.51-7.35 (m, 5H), 7.20-7.13 (m, 3H), 6.58 (d, 1H), 6.11 (s, 1H), 5.18 (s, 2H), 1.89 (m, 1H), 0.92 (m, 2H), 0.68 (m, 2H).

Example 16

N-{3-[2-(dimethylamino)ethyl]phenyl}-4-(2-{4-[(2-methoxybenzyl)oxy]phenyl}imidazo[1,2-a]pyridin-3-yl)pyrimidin-2-amine The title compound was prepared as described in EXAMPLE 12K substituting 4-(2-methoxybenzyloxy)phenylboronic acid for 4-(benzyloxy)-3-methoxyphenylboronic acid. MS (ESI(+)) m/e 571.2 (M+H)+; $^1$H NMR (500 MHz, dimethylsulfoxide-$d_6$) δ ppm 9.69 (s, 1 H) 9.57 (d, 1 H) 8.35 (d, 1 H) 7.73 (d, 1 H) 7.64 (s, 1 H) 7.59 (d, 3 H) 7.46 (m, 2 H) 7.36 (t, 1 H) 7.20 (t, 1 H) 7.07 (m, 4 H) 6.99 (t, 1 H) 6.85 (d, 1 H) 6.64 (d, 1 H) 5.11 (s, 2 H) 3.84 (s, 3 H) 2.66 (m, 2 H) 2.44 (m, 2 H) 2.15 (s, 6 H).

Example 17

N-{3-[2-(dimethylamino)ethyl]phenyl}-4-(2-{4-[(4-methoxybenzyl)oxy]phenyl}imidazo[1,2-a]pyridin-3-yl)pyrimidin-2-amine The title compound was prepared as described in EXAMPLE 12K substituting 4-(4-methoxybenzyloxy)phenylboronic acid for 4-(benzyloxy)-3-methoxyphenylboronic acid. MS (ESI(+)) m/e 571.2 (M+H)+; $^1$H NMR (500 MHz, dimethylsulfoxide-$d_6$) δ ppm 9.68 (s, 1 H) 9.57 (d, 1 H) 8.34 (d, 1 H) 7.73 (d, 1 H) 7.64 (s, 1 H) 7.58 (d, 3 H) 7.47 (m, 1 H) 7.42 (d, 2 H) 7.20 (t, 1 H) 7.09 (m, 2 H) 7.05 (t, 1 H) 6.97 (d, 2 H) 6.85 (d, 1 H) 6.62 (d, 1 H) 5.07 (s, 2 H) 3.77 (s, 3 H) 2.67 (m, 2 H) 2.47 (m, 2 H) 2.18 (s, 6 H).

Example 18

N-{3-[2-(dimethylamino)ethyl]phenyl}-4-(2-{4-[(2-fluorobenzyl)oxy]phenyl}imidazo[1,2-a]pyridin-3-yl)pyrimidin-2-amine The title compound was prepared as described in EXAMPLE 12K substituting 4-(2-fluorobenzyloxy)phenylboronic acid for 4-(benzyloxy)-3-methoxyphenylboronic acid. MS (ESI(+)) m/e 559.2 (M+H)$^+$; $^1$H NMR (500 MHz, dimethylsulfoxide-d$_6$) δ ppm 9.68 (s, 1 H) 9.56 (d, 1 H) 8.35 (d, 1 H) 7.73 (d, 1 H) 7.60 (m, 5 H) 7.46 (m, 2 H) 7.27 (m, 2 H) 7.20 (t, 1 H) 7.13 (d, 2 H) 7.05 (t, 1 H) 6.85 (d, 1 H) 6.63 (d, 1 H) 5.20 (s, 2 H) 2.66 (m, 2 H) 2.43 (m, 2 H) 2.14 (s, 6 H).

Example 19

N-{3-[2-(dimethylamino)ethyl]phenyl}-4-(2-{4-[(3-fluorobenzyl)oxy]phenyl}imidazo[1,2-a]pyridin-3-yl)pyrimidin-2-amine The title compound was prepared as described in EXAMPLE 12K substituting 4-(3-fluorobenzyloxy)phenylboronic acid for 4-(benzyloxy)-3-methoxyphenylboronic acid. MS (ESI(+)) m/e 559.2 (M+H)$^+$; $^1$H NMR (500 MHz, dimethylsulfoxide-d$_6$) δ ppm 9.68 (s, 1 H) 9.56 (d, 1 H) 8.34 (d, 1 H) 7.73 (d, 1 H) 7.63 (s, 1 H) 7.59 (t, 3 H) 7.47 (m, 2 H) 7.33 (m, 2 H) 7.19 (m, 2 H) 7.11 (d, 2 H) 7.05 (t, 1 H) 6.85 (d, 1 H) 6.62 (d, 1 H) 5.19 (s, 2 H) 2.66 (m, 2 H) 2.42 (m, 2 H) 2.14 (s, 6 H).

Example 20

N-{3-[2-(dimethylamino)ethyl]phenyl}-4-(2-{4-[(4-fluorobenzyl)oxy]phenyl}imidazo[1,2-a]pyridin-3-yl)pyrimidin-2-amine The title compound was prepared as described in EXAMPLE 12K substituting 4-(4-fluorobenzyloxy)phenylboronic acid for 4-(benzyloxy)-3-methoxyphenylboronic acid. MS (ESI(+)) m/e 559.3 (M+H)$^+$; $^1$H NMR (500 MHz, dimethylsulfoxide-d$_6$) δ ppm 9.68 (s, 1 H) 9.56 (d, 1 H) 8.34 (d, 1 H) 7.73 (d, 1 H) 7.63 (s, 1 H) 7.59 (m, 3 H) 7.54 (dd, 2H) 7.47 (m, 1 H) 7.24 (t, 2 H) 7.20 (t, 1 H) 7.11 (d, 2 H) 7.05 (t, 1 H) 6.85 (d, 1 H) 6.62 (d, 1 H) 5.14 (s, 2 H) 2.65 (m, 2 H) 2.42 (m, 2 H) 2.14 (s, 6 H).

Example 21

N-{3-[2-(dimethylamino)ethyl]phenyl}-4-{2-[4-(1-phenylethoxy)phenyl]imidazo[1,2-a]pyridin-3-yl}pyrimidin-2-amine

Example 21A 4-(3-(2-(3-(2-(dimethylamino)ethyl)phenylamino)pyrimidin-4-yl)imidazo[1,2-a]pyridin-2-yl)phenol The title compound was prepared as described in EXAMPLE 12K substituting 4-hydroxyphenylboronic acid for 4-(benzyloxy)-3-methoxyphenylboronic acid. MS (ESI (+)) m/e 451.2 (M+H)$^+$.

Example 21B

N-{3-[2-(dimethylamino)ethyl]phenyl}-4-{2-[4-(1-phenylethoxy)phenyl]imidazo[1,2-a]pyridin-3-yl}pyrimidin-2-amine A 10 ml reaction vessel was charged with EXAMPLE 21A (31 mg, 0.069 mmol), DL-sec-phenethylalcohol (10.93 mg, 0.089 mmol), triphenylphosphine (57.3 mg, 0.103 mmol) (polymer bound), and anhydrous tetrahydrofuran (1 ml). The reaction mixture was treated with diisopropyl azodicarboxylate (0.017 ml, 0.089 mmol), and vessel sealed. The mixture stirred for 12 hours at ambient temperature. Additional triphenylphosphine (31 mg, 0.069 mmol), DL-sec-phenethylalcohol (10.93 mg, 0.089 mmol), and diisopropyl azodicarboxylate (0.017 ml, 0.089 mmol) were added to the reaction, and reaction was warmed at 70° C. for a further 24 hours. The reaction was filtered through a fritted funnel and washed with chloroform, and the filtrate was concentrated. The residue was purified on a Shimadzu SIL-10 HPLC system using a Phenominex Gemini 10 micron C18 column (150×30 mm, 110 Angstrom pore size), eluting with a gradient of 40% to 90% CH$_3$CN/water with 0.1% NH$_4$OH. MS (ESI(+)) m/e 555.2 (M+H)$^+$; $^1$H NMR (500 MHz, dimethylsulfoxide-d$_6$) δ ppm 9.66 (s, 1 H) 9.53 (d, 1 H) 8.31 (d, 1 H) 7.69 (d, 1 H) 7.61 (s, 1 H) 7.57 (d, 1 H) 7.49 (d, 2 H) 7.45 (m, 3 H) 7.36 (t, 2 H) 7.27 (t, 1 H) 7.19 (t, 1 H) 7.03 (t, 1 H) 6.99 (d, 2 H) 6.84 (d, 1 H) 6.56 (d, 1 H) 5.58 (q, 1 H) 2.65 (m, 2 H) 2.42 (m, 2 H) 2.14 (s, 6 H) 1.58 (d, 3 H).

Example 22

4-{2-[4-(benzyloxy)phenyl]imidazo[1,2-a]pyridin-3-yl}-N-(4-chloro-2-methoxyphenyl)pyrimidin-2-amine

Example 22A

N-(4-chloro-2-methoxyphenyl)-4-(2-chloroimidazo[1,2-a]pyridin-3-yl)pyrimidin-2-amine The title compound was prepared as described in EXAMPLE 12J, substituting 4-chloro-2-methoxyaniline for EXAMPLE 12I. MS (ESI) m/e 386 (M+H)$^+$.

Example 22B

4-{2-[4-(benzyloxy)phenyl]imidazo[1,2-a]pyridin-3-yl}-N-(4-chloro-2-methoxyphenyl)pyrimidin-2-amine The trifluoroacetic acid salt of the title compound was prepared as described in EXAMPLE 12K, substituting EXAMPLE 22A for EXAMPLE 12J and 4-(benzyloxy)phenylboronic acid for 4-(benzyloxy)-3-methoxyphenylboronic acid. MS (ESI) m/e 534 (M+H)$^+$; $^1$H NMR (300 MHz, dimethylsulfoxide-d$_6$) δ 9.54 (d, 1H), 8.84 (s, 1H), 8.36 (d, 1H), 7.84 (m, 2H), 7.74 (m, 1H), 7.58 (d, 2H), 7.49 (m, 2H), 7.33-7.41 (m, 3H), 7.26 (m, 1H), 7.21 (d, 1H), 7.18 (m, 1H), 7.01 (dd, 1H), 6.82 (m, 1H), 6.49 (dd, 1H), 6.66 (m, 1H), 6.63 (d, 1H), 5.19 (s, 2H), 3.89 (s, 3H).

Example 23

4-{2-[4-(benzyloxy)-3-methoxyphenyl]imidazo[1,2-a]pyridin-3-yl}-N-[4-(2-pyrrolidin-1-ylethyl)phenyl]pyrimidin-2-amine

Example 23A 4-(2-chloroimidazo[1,2-a]pyridin-3-yl)-N-(4-(2-(pyrrolidin-1-yl)ethyl)phenyl)pyrimidin-2-amine The title compound was prepared as described in EXAMPLE 12J, substituting 4-(2-(pyrrolidin-1-yl)ethyl)aniline for EXAMPLE 12I. MS (ESI) m/e 419.6 (M+H)$^+$.

Example 23B

4-{2-[4-(benzyloxy)-3-methoxyphenyl]imidazo[1,2-a]pyridin-3-yl}-N-[4-(2-pyrrolidin-1-ylethyl)phenyl]pyrimidin-2-amine The title compound was prepared as described in EXAMPLE 12K, substituting EXAMPLE 23A for EXAMPLE 12J. MS (ESI(+)) m/e 597.2 (M+H)$^+$; $^1$H NMR (300 MHz, dimethylsulfoxide-d$_6$) δ ppm 9.65 (s, 1 H), 9.56 (d, 1 H), 8.34 (d, 1 H), 7.83-6.95 (m, 15 H), 6.67 (d 1 H), 5.14 (s, 2 H), 3.75 (s, 3 H), 2.70 (s, 4 H), 2.45-2.64 (m, 4 H), 1.70 (s, 4 H).

Example 24

4-{2-[4-(benzyloxy)-3-methoxyphenyl]imidazo[1,2-a]pyridin-3-yl}-N-[3-(2-pyrrolidin-1-ylethyl)phenyl]pyrimidin-2-amine

Example 24A 4-(2-chloroimidazo[1,2-a]pyridin-3-yl)-N-(3-(2-(pyrrolidin-1-yl)ethyl)phenyl)pyrimidin-2-amine The title compound was prepared as described in EXAMPLE 12J, substituting 3-(2-(pyrrolidin-1-yl)ethyl)aniline for EXAMPLE 12I. MS (ESI) m/e 419.6 (M+H)$^+$.

Example 24B

4-{2-[4-(benzyloxy)-3-methoxyphenyl]imidazo[1,2-a]pyridin-3-yl}-N-[3-(2-pyrrolidin-1-ylethyl)phenyl]pyrimidin-2-amine The title compound was prepared as described in EXAMPLE 12K, substituting EXAMPLE 24A for EXAMPLE 12J. MS (ESI(+)) m/e 597.2 (M+H)$^+$; $^1$H NMR (300 MHz, dimethylsulfoxide-d$_6$) δ ppm 9.71 (s, 1 H), 9.56 (d, 1 H), 8.37 (d, 1 H), 7.86-6.99 (m, 14 H), 6.85 (d, 1 H), 6.69 (d, 1 H), 5.13 (s, 2 H), 3.74 (s, 3 H), 2.89-2.57 (m, 4 H), 2.50 (s, 4 H), 1.67 (s, 4 H).

Example 25

4-{2-[4-(benzyloxy)-3-methoxyphenyl]imidazo[1,2-a]pyridin-3-yl}-N-(3-morpholin-4-ylphenyl)pyrimidin-2-amine

Example 25A 4-(2-chloroimidazo[1,2-a]pyridin-3-yl)-N-(3-morpholinophenyl)pyrimidin-2-amine The title compound was prepared as described in EXAMPLE 12J, substituting 3-morpholinoaniline for EXAMPLE 12I. MS (ESI(+)) m/e 407.0 (M+H)$^+$.

Example 25B

4-{2-[4-(benzyloxy)-3-methoxyphenyl]imidazo[1,2-a]pyridin-3-yl}-N-(3-morpholin-4-ylphenyl)pyrimidin-2-amine The title compound was prepared as described in EXAMPLE 12K, substituting EXAMPLE 25A for EXAMPLE 12J. MS (ESI(+)) m/e 585.2 (M+H)$^+$; $^1$H NMR (300 MHz, dimethylsulfoxide-d$_6$) δ ppm 9.60 (s, 1 H) 9.53 (d, 1 H) 8.37 (d, 1 H) 7.74 (d, 1 H) 7.31-7.54 (m, 7 H) 7.27 (d, 1 H) 7.24 (d, 1 H) 7.09-7.21 (m, 3 H) 7.05 (td, 1 H) 6.68 (d, 1 H) 6.59 (dd, 1 H) 5.13 (s, 2 H) 3.74 (s, 3 H) 3.66-3.72 (m, 4 H) 3.01-3.07 (m, 4 H).

Example 26

4-{2-[4-(benzyloxy)phenyl]imidazo[1,2-a]pyridin-3-yl}-N-(1-methyl-1H-pyrazol-4-yl)pyrimidin-2-amine

Example 26A 4-(2-chloroimidazo[1,2-a]pyridin-3-yl)-N-(1-methyl-1H-pyrazol-4-yl)pyrimidin-2-amine A 5 mL reaction vial equipped with a stir bar was charged with EXAMPLE 12G (0.1 g, 0.377 mmol), 1-methyl-1H-pyrazol-4-amine (0.039 g, 0.404 mmol), 2-propanol (2 ml) and 4 M HCl in dioxane (0.094 mL, 0.377 mmol). The vessel was sealed and the mixture was heated on a thermal block at 120° C. for 5 hours. The reaction was cooled to ambient temperature. The suspension was filtered and collected solid was washed with 2-propanol (1.5 mL) and dried. The solid was suspended in 80 mL 20% methanol/CHCl$_3$, washed with saturated aqueous sodium bicarbonate and brine, dried over Na$_2$SO$_4$, filtered, and concentrated. The concentrate was purified by flash chromatography on a 5 g silica gel column eluting with a gradient of methanol in CH$_2$Cl$_2$ to provide the title compound. MS (ESI(+)) m/e 325.9 (M+H)$^+$.

Example 26B

4-{2-[4-(benzyloxy)phenyl]imidazo[1,2-a]pyridin-3-yl}-N-(1-methyl-1H-pyrazol-4-yl)pyrimidin-2-amine The trifluoroacetic acid salt of the title compound was prepared as described in EXAMPLE 12K, substituting EXAMPLE 26A for EXAMPLE 12J and 4-(benzyloxy)phenylboronic acid for 4-(benzyloxy)-3-methoxyphenylboronic acid. MS (ESI(+)) m/e 474.1 (M+H)$^+$, $^1$H NMR (300 MHz, methanol-d$_4$) δ ppm 3.85 (s, 3 H) 5.20 (s, 2 H) 6.64 (m, 1 H)

7.21 (m, 2 H) 7.32-7.42 (m, 3 H) 7.44-7.52 (m, 3 H) 7.61 (m, 3 H) 7.86 (brs, 1 H) 7.93 (m, 1 H) 8.03 (m, 1 H) 8.36 (d, 1 H) 9.77 (brs, 1 H).

Example 27

2-{4-[(4-{2-[4-(benzyloxy)phenyl]imidazo[1,2-a]pyridin-3-yl}pyrimidin-2-yl)amino]-1H-pyrazol-1-yl}ethanol

Example 27A 2-(4-(4-(2-chloroimidazo[1,2-a]pyridin-3-yl)pyrimidin-2-ylamino)-1H-pyrazol-1-yl)ethanol The title compound was prepared as described in EXAMPLE 26A, substituting 2-(4-amino-1H-pyrazol-1-yl)ethanol hydrochloride (WO2007/099326) for 1-methyl-1H-pyrazol-4-amine. MS (ESI(+)) m/e 355.9 (M+H)$^+$.

Example 27B

2-{4-[(4-{2-[4-(benzyloxy)phenyl]imidazo[1,2-a]pyridin-3-yl}pyrimidin-2-yl)amino]-1H-pyrazol-1-yl}ethanol The trifluoroacetic acid salt of the title compound was prepared as described in EXAMPLE 12K, substituting EXAMPLE 27A for EXAMPLE 12J and 4-(benzyloxy)phenylboronic acid for 4-(benzyloxy)-3-methoxyphenylboronic acid. MS (ESI(+)) m/e 504.1 (M+H)$^+$, $^1$H NMR (300 MHz, methanol-d$_4$) δ ppm 3.88 (t, 2 H) 4.18 (t, 2 H) 5.20 (s, 2 H) 6.64 (m, 1 H) 7.23 (m, 2 H) 7.32-7.49 (m, 5 H) 7.53 (m, 1 H) 7.62 (m, 3 H) 7.95 (m, 2 H) 8.05 (m, 1 H) 8.36 (d, 1 H) 9.75 (brs, 1 H).

Example 28

4-{2-[4-(benzyloxy)phenyl]imidazo[1,2-a]pyridin-3-yl}-N-(4-fluorophenyl)pyrimidin-2-amine

Example 28A 4-(2-chloroimidazo[1,2-a]pyridin-3-yl)-N-(4-fluorophenyl)pyrimidin-2-amine The title compound was prepared as described in EXAMPLE 12J substituting 4-fluoroaniline for EXAMPLE 12I. MS (ESI(+)) m/e 340.0 (M+H)$^+$.

Example 28B

4-{2-[4-(benzyloxy)phenyl]imidazo[1,2-a]pyridin-3-yl}-N-(4-fluorophenyl)pyrimidin-2-amine The title compound was prepared as described in EXAMPLE 12K substituting EXAMPLE 28A for EXAMPLE 12J and 4-(benzyloxy)phenylboronic acid for 4-(benzyloxy)-3-methoxyphenylboronic acid. MS (ESI(+)) m/e 488.1 (M+H)$^+$; $^1$H NMR (500 MHz, dimethylsulfoxide-d$_6$) δ ppm 9.77 (s, 1 H) 9.52 (d, 1 H) 8.34 (d, 1 H) 7.74 (m, 3 H) 7.58 (d, 2 H) 7.48 (m, 3 H) 7.42 (t, 2 H) 7.35 (m, 1 H) 7.13 (m, 4 H) 7.06 (t, 1 H) 6.64 (d, 1 H) 5.16 (s, 2 H).

Example 29

4-{2-[4-(benzyloxy)phenyl]imidazo[1,2-a]pyridin-3-yl}-N-(2,4-difluorophenyl)pyrimidin-2-amine

Example 29A 4-(2-chloroimidazo[1,2-a]pyridin-3-yl)-N-(2,4-difluorophenyl)pyrimidin-2-amine The title compound was prepared as described in EXAMPLE 12J substituting 2,4-difluoroaniline for EXAMPLE 12I. MS (ESI(+)) m/e 357.9 (M+H)$^+$.

Example 29B

4-{2-[4-(benzyloxy)phenyl]imidazo[1,2-a]pyridin-3-yl}-N-(2,4-difluorophenyl)pyrimidin-2-amine The title compound was prepared as described in EXAMPLE 12K substituting EXAMPLE 29A for EXAMPLE 12J and 4-(benzyloxy)phenylboronic acid for 4-(benzyloxy)-3-methoxyphenylboronic acid. MS (ESI(+)) m/e 506 (M+H)$^+$; $^1$H NMR (500 MHz, dimethylsulfoxide-d$_6$) δ ppm 9.46 (bs, 1 H) 9.32 (s, 1 H) 8.25 (d, 1 H) 7.69 (m, 2 H) 7.55 (d, 2 H) 7.48 (d, 2 H) 7.46 (m, 1 H) 7.42 (m, 2 H) 7.36 (m, 2 H) 7.11 (m, 3 H) 6.99 (t, 1 H) 6.59 (d, 1 H) 5.17 (s, 2 H).

Example 30

4-{2-[4-(benzyloxy)-3-methoxyphenyl]imidazo[1,2-a]pyridin-3-yl}-N-[3-(2-pyrrolidin-1-ylethoxy)phenyl]pyrimidin-2-amine

Example 30A 4-(2-chloroimidazo[1,2-a]pyridin-3-yl)-N-(3-(2-(pyrrolidin-1-yl)ethoxy)phenyl)pyrimidin-2-amine The title compound was prepared as described in EXAMPLE 12J, substituting 3-(2-(pyrrolidin-1-yl)ethoxy)aniline for EXAMPLE 12I. MS (ESI(+)) m/e 435.4 (M+H)$^+$.

Example 30B

4-{2-[4-(benzyloxy)-3-methoxyphenyl]imidazo[1,2-a]pyridin-3-yl}-N-[3-(2-pyrrolidin-1-ylethoxy)phenyl]pyrimidin-2-amine The title compound was prepared as described in EXAMPLE 12K, substituting EXAMPLE 30A for EXAMPLE 12J. MS (ESI(+)) m/e 613.3 (M+H)$^+$; $^1$H NMR (300 MHz, dimethylsulfoxide-d$_6$) δ ppm 9.73 (s, 1 H), 9.56 (d, 1 H), 8.38 (d, 1 H), 7.74 (d, 1H), 7.60-6.99 (m, 13 H), 6.70 (d, 1 H), 6.57 (dd, 1 H), 5.14 (s, 2 H), 4.01 (t, 2 H), 3.75 (s, 3 H), 2.76 (t, 2 H), 2.50 (s, 4 H). 1.84-1.50 (m, 4 H).

Example 31

2-[{3-[(4-{2-[4-(benzyloxy)-3-methoxyphenyl]imidazo[1,2-a]pyridin-3-yl}pyrimidin-2-yl)amino]phenyl}(ethyl)amino]ethanol

Example 31A

2-((3-(4-(2-chloroimidazo[1,2-a]pyridin-3-yl)pyrimidin-2-ylamino)phenyl)(ethyl)amino)ethanol The title compound was prepared as described in EXAMPLE 12J, substituting 2-((3-aminophenyl)(ethyl)amino)ethanol for EXAMPLE 12I. MS (ESI(+)) m/e 409.6 (M+H)$^+$.

Example 31B

2-[{3-[(4-{2-[4-(benzyloxy)-3-methoxyphenyl]imidazo[1,2-a]pyridin-3-yl}pyrimidin-2-yl)amino]phenyl}(ethyl)amino]ethanol The title compound was prepared as described in EXAMPLE 12K, substituting EXAMPLE 31A for EXAMPLE 12J. MS (ESI(+)) m/e 587.2 (M+H)$^+$; $^1$H NMR (300 MHz, dimethylsulfoxide-d$_6$) δ ppm 9.54 (s, 1 H), 9.26 (s, 1 H), 8.25 (d, 1 H), 7.71 (d, 1 H), 7.57-7.31 (m, 8 H), 7.26 (d, 1 H), 7.21-7.07 (m, 2 H), 6.99 (t, 1 H), 6.66 (d, 2 H), 6.55 (d, 1 H), 5.14 (s, 2 H), 4.64 (t, 1 H), 3.75 (s, 3 H), 3.54 (q, 2 H), 3.44-3.29 (m, 4 H), 1.07 (t, 3 H).

Example 32

4-{2-[4-(benzyloxy)-3-methoxyphenyl]imidazo[1,2-a]pyridin-3-yl}-N-[4-(1,1-dioxidothiomorpholin-4-yl)phenyl]pyrimidin-2-amine

Example 32A

4-(2-chloroimidazo[1,2-a]pyridin-3-yl)-N-(4-dioxidothiomorpholinophenyl)pyrimidin-2-amine The title compound was prepared as described in EXAMPLE 12J, substituting 4-dioxidothiomorpholinoaniline for EXAMPLE 12I. MS (ESI(+)) m/e 454.9 (M+H)$^+$.

Example 32B

4-{2-[4-(benzyloxy)-3-methoxyphenyl]imidazo[1,2-a]pyridin-3-yl}-N-[4-(1,1-dioxidothiomorpholin-4-yl)phenyl]pyrimidin-2-amine The title compound was prepared as described in EXAMPLE 12K, substituting EXAMPLE 32A for EXAMPLE 12J. MS (ESI(+)) m/e 633.2 (M+H)$^+$; $^1$H NMR (300 MHz, dimethylsulfoxide-d$_6$) δ ppm 9.54 (s, 2 H) 8.31 (d, 1 H) 7.73 (d, 1 H) 7.60 (d, 2 H) 7.32-7.51 (m, 6 H) 7.26 (d, 1 H) 7.10-7.20 (m, 2 H) 6.97-7.08 (m, 3 H) 6.63 (d, 1 H) 5.13 (s, 2 H) 3.75 (s, 3 H) 3.66-3.73 (m, 4 H) 3.10-3.18 (m, 4 H).

Example 33

4-{2-[4-(benzyloxy)-3-methoxyphenyl]imidazo[1,2-a]pyridin-3-yl}-N-{4-[4-(dimethylamino)piperidin-1-yl]-2-methoxyphenyl}pyrimidin-2-amine

Example 33A

1-(3-methoxy-4-nitrophenyl)-N,N-dimethylpiperidin-4-amine

A 100 ml flask was charged with 4-fluoro-2-methoxy-1-nitrobenzene (5.13 g, 30 mmol), N,N-dimethylpiperidin-4-amine (4.23 g, 33.0 mmol) and N,N-dimethylformamide (60 ml). To the mixture was added N-ethyl-N-isopropylpropan-2-amine (10.45 ml, 60.0 mmol) and the mixture was heated at 70° C. overnight under nitrogen. The reaction mixture was concentrated under high vacuum and the residue was partitioned between brine (100 ml) and methylene chloride (100 ml) and the pH adjusted to ca. 12-14 with sodium hydroxide. The layers were separated and the aqueous layer was extracted with methylene chloride (3×100 ml). The combined organics were dried over sodium sulfate, filtered and adsorbed directly on to silica gel (ca. 25 g). This was split in two portions each of which was purified on a silica gel cartridge (150 g) eluted with a 2.5, 4.5, 6% 7N methanolic ammonia in methylene chloride step gradient. The combined product fractions were concentrated to provide the title compound. MS (DCI(+)) m/e 280.2 (M+H)$^+$.

Example 33B

1-(4-amino-3-methoxyphenyl)-N,N-dimethylpiperidin-4-amine

A 500 ml flask containing EXAMPLE 33A (8.38 g, 30.00 mmol) was charged with ethanol (160 ml). To the resulting solution was added iron (8.80 g, 158 mmol) followed by a solution of ammonium chloride (1.605 g, 30.0 mmol) in water (40.0 ml). The reaction mixture was heated to 100° C. After 1.5 hours the reaction was filtered hot through a membrane filter and washed with hot methanol/ethyl acetate (200 ml). The combined filtrate and washes were concentrated and the residue partitioned between saturated sodium bicarbonate solution (150 ml) and 5% methanol in methylene chloride (100 ml). The mixture was basified to pH 12-14, diluted with brine (about 100 ml) and after separating the layers the aqueous layer was extracted with 5% methanol in methylene chloride until the product was removed from the aqueous layer. The combined organics were dried over sodium sulfate, filtered and concentrated to give the title compound. MS (DCI (+)) m/e 250.1 (M+H)$^+$.

Example 33C

4-(2-chloroimidazo[1,2-a]pyridin-3-yl)-N-(4-(4-(dimethylamino)piperidin-1-yl)-2-methoxyphenyl)pyrimidin-2-amine The title compound was prepared as described in EXAMPLE 12J, substituting EXAMPLE 33B for EXAMPLE 12I. MS (ESI(+)) m/e 478.1 (M+H)$^+$.

Example 33D

4-{2-[4-(benzyloxy)-3-methoxyphenyl]imidazo[1,2-a]pyridin-3-yl}-N-{4-[4-(dimethylamino)piperidin-1-yl]-2-methoxyphenyl}pyrimidin-2-amine The title compound was prepared as described in EXAMPLE 12K, substituting EXAMPLE 33C for EXAMPLE 12J. MS (ESI(+)) m/e 656.3 (M+H)$^+$; $^1$H NMR (300 MHz, dimethylsulfoxide-$d_6$) δ ppm 9.41 (d, 1 H) 8.39 (s, 1 H) 8.21 (d, 1 H) 7.69 (d, 1 H) 7.31-7.52 (m, 7 H) 7.23 (s, 1 H) 7.13 (s, 2 H) 6.93 (t, 1 H) 6.68 (d, 1 H) 6.48-6.55 (m, 2 H) 5.13 (s, 2 H) 3.80 (s, 3 H) 3.69-3.76 (m, 5 H) 2.72-2.64 (m, 2 H) 2.16-2.22 (m, 7 H) 1.85 (d, 2 H) 1.58-1.42 (m, 2 H).

Example 34

4-{2-[4-(benzyloxy)-3-methoxyphenyl]imidazo[1,2-a]pyridin-3-yl}-N-[2-methoxy-5-(methylsulfonyl)phenyl]pyrimidin-2-amine

Example 34A 4-(2-chloroimidazo[1,2-a]pyridin-3-yl)-N-(2-methoxy-5-(methylsulfonyl)phenyl)pyrimidin-2-amine The title compound was prepared as described in EXAMPLE 12J, substituting 2-methoxy-5-(methylsulfonyl)aniline for EXAMPLE 12I. MS (ESI(+)) m/e 429.9 (M+H)$^+$.

Example 34B

4-{2-[4-(benzyloxy)-3-methoxyphenyl]imidazo[1,2-a]pyridin-3-yl}-N-[2-methoxy-5-(methylsulfonyl)phenyl]pyrimidin-2-amine The title compound was prepared as described in EXAMPLE 12K, substituting EXAMPLE 34A for EXAMPLE 12J. MS (ESI(+)) m/e 608.2 (M+H)$^+$; $^1$H NMR (300 MHz, dimethylsulfoxide-$d_6$) δ ppm 9.50 (d, 1H), 8.78 (s, 1H), 8.57 (d, 1H), 8.37 (d, 1H), 7.72 (d, 1H), 7.66 (dd, 1H), 7.50-7.33 (m, 6H), 7.25 (m, 1H), 7.18-7.12 (m, 2H), 7.04 (m, 1H), 6.72 (d, 1H), 5.14 (s, 2H), 3.99 (s, 3H), 3.75 (s, 3H), 3.14 (s, 3H).

Example 35

4-{2-[4-(benzyloxy)phenyl]imidazo[1,2-a]pyridin-3-yl}-N-[2-methoxy-5-(methylsulfonyl)phenyl]pyrimidin-2-amine The title compound was prepared as described in EXAMPLE 12K, substituting EXAMPLE 34A for EXAMPLE 12J and 4-(benzyloxy)-phenylboronic acid for 4-(benzyloxy)-3-methoxyphenylboronic acid. MS (ESI(+)) m/e 578.1 (M+H)$^+$; $^1$H NMR (300 MHz, dimethylsulfoxide-$d_6$) δ ppm 9.49 (d, 1H), 8.79 (s, 1H), 8.57 (d, 1H), 8.35 (d, 1H), 7.71 (d, 1H), 7.67 (dd, 1H), 7.57 (d, 2H), 7.51-7.33 (m, 6H), 7.11 (d, 2H), 7.04 (m, 1H), 6.66 (d, 1H), 5.14 (s, 2H), 3.99 (s, 3H), 3.14 (s, 3H).

Example 36

4-{2-[4-(benzyloxy)-3-methoxyphenyl]imidazo[1,2-a]pyridin-3-yl}-N-{4-[4-(dimethylamino)piperidin-1-yl]phenyl}pyrimidin-2-amine

Example 36A

N,N-dimethyl-1-(4-nitrophenyl)piperidin-4-amine

A 100 ml flask was charged with 1-fluoro-4-nitrobenzene (2.122 ml, 20 mmol), dimethylsulfoxide (30 ml), N,N-dimethylpiperidin-4-amine (2.82 g, 22.00 mmol) and triethylamine (5.58 ml, 40.0 mmol). The resulting solution was stirred at 100° C. under nitrogen for 24 hours. The reaction mixture was allowed to cool, and was poured in stirring cold water (1000 ml) and the solid collected by filtration and washed with water. The precipitate was vacuum dried to provide the title compound. MS (ESI(+)) m/e 249.9 (M+H)$^+$.

Example 36B

N,N-dimethyl-1-(4-aminophenyl)piperidin-4-amine

The title compound was prepared as described in EXAMPLE 33B, substituting EXAMPLE 36A for EXAMPLE 33A. MS (DCI(+)) m/e 220.0 (M+H)$^+$.

Example 36C 4-(2-chloroimidazo[1,2-a]pyridin-3-yl)-N-(4-(4-(dimethylamino)piperidin-1-yl)phenyl)pyrimidin-2-amine The title compound was prepared as described in EXAMPLE 12J, substituting EXAMPLE 36B for EXAMPLE 12I. MS (ESI(+)) m/e 448.0 (M+H)$^+$.

Example 36D

4-{2-[4-(benzyloxy)-3-methoxyphenyl]imidazo[1,2-a]pyridin-3-yl}-N-{4-[4-(dimethylamino)piperidin-1-yl]phenyl}pyrimidin-2-amine The title compound was prepared as described in EXAMPLE 12K, substituting EXAMPLE 36C for EXAMPLE 12J. MS (ESI(+)) m/e 626.3 (M+H)$^+$; $^1$H NMR (300 MHz, dimethylsulfoxide-$d_6$) δ ppm 9.53 (d, 1 H) 9.44 (s, 1 H) 8.29 (d, 1 H) 7.72 (d, 1 H) 7.32-7.56 (m, 8 H) 7.26 (d, 1 H) 7.10-7.19 (m, 2 H) 7.02 (t, 1 H) 6.90 (d, 2 H) 6.61 (d, 1 H) 5.13 (s, 2 H) 3.75 (s, 3 H) 3.62 (d, 2 H) 2.66-2.56 (m, 2 H) 2.11-2.22 (m, 7 H) 1.83 (d, 2 H) 1.57-1.41 (m, 2 H).

Example 37

4-{2-[4-(benzyloxy)-3-methoxyphenyl]imidazo[1,2-a]pyridin-3-yl}-N-[1-(2-pyrrolidin-1-ylethyl)-1H-pyrazol-4-yl]pyrimidin-2-amine

Example 37A 4-nitro-1-(2-(pyrrolidin-1-yl)ethyl)-1H-pyrazole

N-(2-chloroethyl)pyrrolidine hydrochloride (752 mg, 4.42 mmol), potassium carbonate (0.534 ml, 8.84 mmol) and 4-nitro-1H-pyrazole (500 mg, 4.42 mmol) were combined in acetone (20 ml) and the reaction was stirred at reflux for 16 hours. The reaction mixture was diluted with 75 mL water and extracted with ethyl acetate (3×20 mL). The combined organics were dried (Na$_2$SO$_4$), filtered, and concentrated to give the title compound. MS (ESI(+)) m/e 210.9 (M+H)$^+$.

Example 37B 1-(2-(pyrrolidin-1-yl)ethyl)-1H-pyrazol-4-amine, bis hydrochloric acid salt EXAMPLE 37A (1.6 g, 7.61 mmol) was dissolved in methanol (76 ml) and the flask was equipped with a hydrogenation stopcock apparatus. The flask was purged with N$_2$ and 10% Pd/C (100 mg, 7.61 mmol) was added. The flask was again purged with N$_2$, then flushed with H$_2$ and left overnight stirring under H$_2$ atmosphere (balloon). Following N$_2$ purge, the reaction mixture was filtered through Celite® (diatomaceous earth), rinsing with methanol. The filtrate was concentrated in vacuo to give a viscous oil. This material was dissolved in dioxane and treated with 4N HCl in dioxane. The mixture was concentrated to dryness and dried in a vaccuum oven, to provide the title compound. MS (ESI(+)) m/e 181.0 (M+H)$^+$.

Example 37C 4-(2-chloroimidazo[1,2-a]pyridin-3-yl)-N-(1-(2-(pyrrolidin-1-yl)ethyl)-1H-pyrazol-4-yl)pyrimidin-2-amine The title compound was prepared as described in EXAMPLE 12J, substituting EXAMPLE 37B for EXAMPLE 12I. MS (ESI(+)) m/e 409.0 (M+H)$^+$.

Example 37D

4-{2-[4-(benzyloxy)-3-methoxyphenyl]imidazo[1,2-a]pyridin-3-yl}-N-[1-(2-pyrrolidin-1-ylethyl)-1H-pyrazol-4-yl]pyrimidin-2-amine The title compound was prepared as described in EXAMPLE 12K, substituting EXAMPLE 37C for EXAMPLE 12J. MS (ESI(+)) m/e 587.2 (M+H)$^+$; $^1$H NMR (300 MHz, dimethylsulfoxide-d$_6$) δ ppm 9.77-9.09 (br, 1 H) 9.58 (s, 1 H) 8.33 (d, 1 H) 7.91 (s, 1 H) 7.73 (d, 1 H) 7.31-7.54 (m, 7 H) 7.26 (d, 1 H) 7.10-7.20 (m, 2 H) 6.99-7.10 (m, 1 H) 6.59 (d, 1 H) 5.13 (s, 2 H) 4.14 (t, 2 H) 3.74 (s, 3 H) 2.78 (t, 2 H) 2.38-2.47 (m, 4 H) 1.62 (s, 4 H).

Example 38

2-[(2-{3-[(4-{2-[4-(benzyloxy)-3-methoxyphenyl] imidazo[1,2-a]pyridin-3-yl}pyrimidin-2-yl)amino] phenyl}ethyl)(methyl)amino]ethanol

Example 38A 3-nitrophenethyl 4-methylbenzenesulfonate

A 500 mL round-bottomed flask was charged with 2-(3-nitrophenyl)ethanol (1.0235 g, 6.12 mmol), 4-dimethylaminopyridine (0.075 g, 0.612 mmol) and p-toluenesulfonyl chloride (1.401 g, 7.35 mmol) in CH$_2$Cl$_2$ (61.2 ml). Triethylamine (1.707 ml, 12.25 mmol) was added, and the mixture stirred at ambient temperature for 3 hours. The reaction mixture was washed with water and brine, dried (MgSO$_4$), filtered and concentrated onto silica gel. The crude product was purified by flash chromatography using an Argonaut Flashmaster Solo 25 g column (100% hexanes to 30% ethyl acetate:hexanes over 25 minutes, then to 100% ethyl acetate over 10 minutes) to provide the title compound. MS (ESI(+)) m/e 338.9 (M+NH$_4$)$^+$.

Example 38B 2-(methyl(3-nitrophenethyl)amino)ethanol

A 5 mL microwave vial was charged with EXAMPLE 38A (0.500 g, 1.556 mmol), triethylamine (0.651 ml, 4.67 mmol) and 2-(methylamino)ethanol (0.351 g, 4.67 mmol) in acetonitrile (1.6 ml). The vial was sealed and heated to 150° C. for 20 minutes in a Biotage Initiator microwave reactor. The reaction mixture was partitioned between ethyl acetate and aqueous sodium bicarbonate, dried (MgSO$_4$), filtered and concentrated, and the residue was purified by flash chromatography using an Argonaut Flashmaster Solo 10 g column (100% CH$_2$Cl$_2$ for 5 minutes, then to 10% methanol:CH$_2$Cl$_2$ over 20 minutes, then held at 10% methanol:CH$_2$Cl$_2$ for 5 minutes) to provide the title compound. MS (ESI(+)) m/e 224.9 (M+H)$^+$.

Example 38C 2-((4-aminophenethyl)(methyl)amino)ethanol

The title compound was prepared as described in EXAMPLE 33B, substituting EXAMPLE 38B for EXAMPLE 33A. MS (DCI(+)) m/e 195.0 (M+H)$^+$.

Example 38D 2-((4-(4-(2-chloroimidazo[1,2-a]pyridin-3-yl)pyrimidin-2-ylamino)phenethyl)(methyl)amino)ethanol The title compound was prepared as described in EXAMPLE 12J, substituting EXAMPLE 38D for EXAMPLE 12I. MS (ESI(+)) m/e 423.6 (M+H)$^+$.

Example 38E

2-[(2-{3-[(4-{2-[4-(benzyloxy)-3-methoxyphenyl] imidazo[1,2-a]pyridin-3-yl}pyrimidin-2-yl)amino] phenyl}ethyl)(methyl)amino]ethanol The title compound was prepared as described in EXAMPLE 12K, substituting EXAMPLE 38D for EXAMPLE 12J. MS (ESI(+)) m/e 601.3 (M+H)$^+$; $^1$H NMR (300 MHz, dimethylsulfoxide-d$_6$) δ ppm 9.67 (s, 1 H), 9.57 (d, 1 H), 8.36 (d, 1 H), 7.74 (d, 1H), 7.68-7.54 (m, 2 H), 7.53-6.97 (m, 11 H), 6.85 (d, 1 H), 6.68 (d, 1 H), 5.14 (s, 2 H), 4.30 (s, 1 H), 3.75 (s, 3 H), 3.46 (q, 2 H), 2.75-2.53 (m, 4 H), 2.45 (t, 2 H), 2.22 (s, 3 H).

Example 39

4-{2-[4-(benzyloxy)-3-methoxyphenyl]imidazo[1,2-a]pyridin-3-yl}-N-(2-methoxy-4-morpholin-4-ylphenyl)pyrimidin-2-amine The title compound was prepared as described in EXAMPLE 12K, substituting EXAMPLE 2A for EXAMPLE 12J. MS (ESI(+)) m/e 615.2 (M+H)$^+$; $^1$H NMR (300 MHz, dimethylsulfoxide-d$_6$) δ ppm 9.42 (bdd, 1 H) 8.42 (s, 1 H), 8.22 (d, 1 H), 7.67 (m, 2 H), 7.51-7.34 (m, 7 H), 7.23

(s, 1 H), 7.13 (s, 1 H), 6.94 (m, 1 H), 6.71 (d, 1 H), 6.54 (d, 1 H), 6.52 (dd, 1 H), 5.14 (s, 2 H), 3.81 (s, 3 H), 3.77 (m, 4 H), 3.75 (s, 3 H), 3.14 (m, 4 H).

Example 40

4-{2-[4-(benzyloxy)-3-methoxyphenyl]imidazo[1,2-a]pyridin-3-yl}-N-[2-methoxy-5-(trifluoromethyl)phenyl]pyrimidin-2-amine

Example 40A 4-(2-chloroimidazo[1,2-a]pyridin-3-yl)-N-(2-methoxy-5-(trifluoromethyl)phenyl)pyrimidin-2-amine The title compound was prepared as described in EXAMPLE 12J, substituting 2-methoxy-5-(trifluoromethyl)aniline for EXAMPLE 12I. MS (ESI(+)) m/e 419.9 (M+H)$^+$.

Example 40B

4-{2-[4-(benzyloxy)-3-methoxyphenyl]imidazo[1,2-a]pyridin-3-yl}-N-[2-methoxy-5-(trifluoromethyl)phenyl]pyrimidin-2-amine The title compound was prepared as described in EXAMPLE 12K, substituting EXAMPLE 40A for EXAMPLE 12J. MS (ESI(+)) m/e 598.2 (M+H)$^+$; $^1$H NMR (300 MHz, dimethylsulfoxide-d$_6$) δ ppm 9.48 (m, 1H), 8.68 (s, 1H), 8.45 (d, 1H), 8.38 (m, 1H), 7.73 (m, 1H), 7.50-7.25 (m, 8H), 7.14 (m, 2H), 6.99 (m, 1H), 6.72 (m, 1H), 5.14 (s, 2H), 3.97 (s, 3H), 3.74 (s, 3H).

Example 41

4-{2-[4-(benzyloxy)phenyl]imidazo[1,2-a]pyridin-3-yl}-N-[2-methoxy-5-(trifluoromethyl)phenyl]pyrimidin-2-amine The title compound was prepared as described in EXAMPLE 12K, substituting EXAMPLE 40A for EXAMPLE 12J and 4-(benzyloxy)-phenylboronic acid for 4-(benzyloxy)-3-methoxyphenylboronic acid. MS (ESI(+)) m/e 568.2 (M+H)$^+$; $^1$H NMR (300 MHz, dimethylsulfoxide-d$_6$) δ ppm 9.47 (m, 1H), 8.68 (s, 1H), 8.44 (m, 1H), 8.36 (d, 1H), 7.71 (d, 1H), 7.57 (d, 2H), 7.52-7.35 (m, 6H), 7.29 (d, 1H), 7.10 (d, 2H), 6.99 (m, 1H), 6.67 (d, 1H), 5.16 (s, 2H), 3.97 (s, 3H).

Example 42

N$^1$-(4-{2-[4-(benzyloxy)-3-methoxyphenyl]imidazo[1,2-a]pyridin-3-yl}pyrimidin-2-yl)-2-methoxy-N$^4$,N$^4$-dimethylbenzene-1,4-diamine

Example 42A

N$^1$-(4-(2-chloroimidazo[1,2-a]pyridin-3-yl)pyrimidin-2-yl)-2-methoxy-N$^4$,N$^4$-dimethylbenzene-1,4-diamine The title compound was prepared as described in EXAMPLE 12J, substituting 2-methoxy-4-(dimethylamino)aniline for EXAMPLE 12I. MS (ESI(+)) m/e 395.0 (M+H)$^+$.

Example 42B

N$^1$-(4-{2-[4-(benzyloxy)-3-methoxyphenyl]imidazo[1,2-a]pyridin-3-yl}pyrimidin-2-yl)-2-methoxy-N$^4$,N$^4$-dimethylbenzene-1,4-diamine The title compound was prepared as described in EXAMPLE 12K, substituting EXAMPLE 42A for EXAMPLE 12J. MS (ESI(+)) m/e 573.2 (M+H)$^+$; $^1$H NMR (300 MHz, dimethylsulfoxide-d$_6$) δ ppm 9.41 (d, 1 H) 8.38 (s, 1 H) 8.19 (d, 1 H) 7.68 (d, 1 H) 7.30-7.52 (m, 7 H) 7.23 (s, 1 H) 7.13 (s, 2 H) 6.90 (t, 1 H) 6.50 (d, 1 H) 6.46 (d, 1 H) 6.32 (dd, 1 H) 5.14 (s, 2 H) 3.80 (s, 3 H) 3.75 (s, 3 H) 2.93 (s, 6 H).

Example 43

4-{2-[4-(benzyloxy)-3-methoxyphenyl]imidazo[1,2-a]pyridin-3-yl}-N-{1-[2-(dimethylamino)ethyl]-1H-pyrazol-4-yl}pyrimidin-2-amine

Example 43A

N,N-dimethyl-2-(4-nitro-1H-pyrazol-1-yl)ethanamine

The title compound was prepared as described in EXAMPLE 37A, substituting 2-chloroethyldimethylamine hydrochloride for N-(2-chloroethyl)pyrrolidine hydrochloride. MS (ESI(+)) m/e 184.9 (M+H)$^+$.

Example 43B 1-(2-(dimethylamino)ethyl)-1H-pyrazol-4-amine

The title compound was prepared as the dihydrochloride salt as described in EXAMPLE 37B, substituting EXAMPLE 43A for EXAMPLE 37A. MS (ESI(+)) m/e 155.1 (M+H)$^+$.

Example 43C 4-(2-chloroimidazo[1,2-a]pyridin-3-yl)-N-(1-(2-(dimethylamino)ethyl)-1H-pyrazol-4-yl)pyrimidin-2-amine The title compound was prepared as described in EXAMPLE 12J, substituting EXAMPLE 43B for EXAMPLE 12I. MS (ESI(+)) m/e 383.0 (M+H)$^+$.

Example 43D

4-{2-[4-(benzyloxy)-3-methoxyphenyl]imidazo[1,2-a]pyridin-3-yl}-N-{1-[2-(dimethylamino)ethyl]-1H-pyrazol-4-yl}pyrimidin-2-amine The title compound was prepared as described in EXAMPLE 12K, substituting EXAMPLE 43C for EXAMPLE 12J. MS ESI(+)) m/e 561.2 (M+H)$^+$; $^1$H NMR (300 MHz, dimethylsulfoxide-d$_6$) δ ppm 9.78-9.09 (br, 1 H) 9.57 (s, 1 H) 8.33 (d, 1 H) 7.90 (s, 1 H) 7.73 (d, 1 H) 7.31-7.54 (m, 7 H) 7.27 (d, 1 H) 7.09-7.20 (m, 2 H) 7.06 (t, 1 H) 6.59 (d, 1 H) 5.13 (s, 2 H) 4.12 (t, 2 H) 3.74 (s, 3 H) 2.61 (t, 2 H) 2.14 (s, 6 H).

Example 44

2-(4-{4-[(4-{2-[4-(benzyloxy)-3-methoxyphenyl]
imidazo[1,2-a]pyridin-3-yl}pyrimidin-2-yl)amino]
phenyl}piperazin-1-yl)ethanol

Example 44A 2-(4-(4-(4-(2-chloroimidazo[1,2-a]pyridin-3-yl)pyrimidin-2-ylamino)phenyl)piperazin-1-yl)ethanol The title compound was prepared as described in EXAMPLE 12J, substituting 2-(4-(4-aminophenyl)piperazin-1-yl)ethanol for EXAMPLE 12I. MS (ESI(+)) m/e 450.1 (M+H)$^+$.

Example 44B 2-(4-{4-[(4-{2-[4-(benzyloxy)-3-methoxyphenyl]
imidazo[1,2-a]pyridin-3-yl}pyrimidin-2-yl)amino]
phenyl}piperazin-1-yl)ethanol The title compound was prepared as described in EXAMPLE 12K, substituting EXAMPLE 44A for EXAMPLE 12J. MS (ESI(+)) m/e 628.3 (M+H)$^+$; $^1$H NMR (300 MHz, dimethylsulfoxide-d$_6$) δ ppm 9.53 (d, 1 H) 9.45 (s, 1 H) 8.29 (d, 1 H) 7.72 (d, 1 H) 7.31-7.57 (m, 8 H) 7.26 (d, 1 H) 7.10-7.19 (m, 2 H) 7.03 (t, 1 H) 6.90 (d, 2 H) 6.61 (d, 1 H) 5.13 (s, 2 H) 4.41 (t, 1 H) 3.75 (s, 3 H) 3.54 (q, 2 H) 3.04-3.11 (m, 4 H) 2.53-2.59 (m, 4 H) 2.44 (t, 2 H).

Example 45

1-({4-[(4-{2-[4-(benzyloxy)-3-methoxyphenyl]imidazo[1,2-a]pyridin-3-yl}pyrimidin-2-yl)amino]-3-methoxyphenyl}amino)-2-methylpropan-2-ol

Example 45A 1-(3-methoxy-4-nitrophenylamino)-2-methylpropan-2-ol

A 20 mL reaction vial equipped with a stir bar was charged with 4-fluoro-2-methoxy-1-nitrobenzene (0.5 g, 2.92 mmol), 1-amino-2-methylpropan-2-ol (0.313 g, 3.51 mmol), N-methyl-2-pyrrolidinone (7.3 mL) and Hunig's base (N,N-diisopropylethylamine) (0.76 g, 5.84 mmol). The vessel was sealed and the reaction was heated on a thermal block at 80° C. for 24 hours. The reaction was cooled to ambient temperature, treated with water (40 mL) and extracted with ethyl acetate (3×60 mL). The combined organic layers were washed with brine (2×25 mL), dried over Na$_2$SO$_4$, filtered, and concentrated. The concentrate was purified by flash chromatography on a 10 g silica gel column eluting with 1% methanol/CH$_2$Cl$_2$ to provide the title compound. $^1$H NMR (500 MHz, dimethylsulfoxide-d$_6$) δ ppm 1.16 (s, 6H) 3.10 (d, 2H) 3.84 (s, 3H) 4.58 (s, 1H) 6.35 (m, 2H) 6.96 (m, 1H) 7.83 (d, 1H).

Example 45B 1-(4-amino-3-methoxyphenylamino)-2-methylpropan-2-ol

EXAMPLE 45A (0.9 g, 2.81 mmol) in methanol (28 mL) was added to 5% Pd/C (wet, 0.180 g) in a 250 mL stainless steel pressure bottle, and the mixture was shaken under 30 psi of hydrogen at 50° C. for 10 minutes. The mixture was filtered through a nylon membrane and the filtrate was concentrated. The concentrate was purified by flash chromatography on a 10 g silica gel column eluting with a gradient of from 0% to 2% methanol/CH$_2$Cl$_2$ to provide the title compound. MS (ESI (+)) m/e 210.9 (M+H)$^+$.

Example 45C 1-(4-(4-(2-chloroimidazo[1,2-a]pyridin-3-yl)pyrimidin-2-ylamino)-3-methoxyphenylamino)-2-methylpropan-2-ol A 20 mL reaction vial equipped with a stir bar was charged with EXAMPLE 12G (0.36 g, 1.358 mmol), EXAMPLE 45B (80%, 0.375 g, 1.426 mmol) and Hunig's base (0.474 mL, 2.72 mmol) in N-methyl-2-pyrrolidinone (5 ml) and was sealed. The reaction was heated on a thermal block at 98° C. for 44 hours. The reaction was cooled to ambient temperature, diluted with water (25 mL) and extracted with 1:1 ether/ethyl acetate (2×80 mL). The combined organic layers were washed with water (50 mL) and brine (2×50 mL), dried over Na$_2$SO$_4$, and concentrated. The concentrate was triturated with diethyl ether (6 mL) and purified by flash chromatography on an 8 g silica gel column eluting with a gradient of from 0% to 1% methanol/CH$_2$Cl$_2$ to provide the title compound. MS (ESI(+)) m/e 439.0 (M+H)$^+$.

Example 45D 1-({4-[(4-{2-[4-(benzyloxy)-3-methoxyphenyl]imidazo[1,2-a]pyridin-3-yl}pyrimidin-2-yl)amino]-3-methoxyphenyl}amino)-2-methylpropan-2-ol The trifluoroacetic acid salt of the title compound was prepared as described in EXAMPLE 12K, substituting EXAMPLE 45C for EXAMPLE 12J. MS (ESI(+)) m/e 617.2 (M+H)$^+$, $^1$H NMR (300 MHz, methanol-d$_4$) δ ppm 1.32 (s, 6 H) 3.19 (s, 2 H) 3.87 (s, 6 H) 5.21 (s, 2 H) 6.50 (m, 1 H) 6.68 (m, 2 H) 7.19 (m, 2 H) 7.28-7.41 (m, 5 H) 7.48 (m, 3 H) 7.86 (m, 2 H) 8.06 (d, 1 H) 9.83 (m, 1 H).

Example 46

N$^1$-(4-{2-[4-(benzyloxy)-3-methoxyphenyl]imidazo[1,2-a]pyridin-3-yl}pyrimidin-2-yl)-2-methoxybenzene-1,4-diamine The title compound was prepared as described in EXAMPLE 53D. Purification of the crude reaction mixture was performed using reverse-phase HPLC on a Phenomenex C18 column (3×15 cm) using a gradient of acetonitrile in 0.1% aqueous ammonium hydroxide MS (ESI(+)) m/e 545.2 (M+H)$^+$, $^1$H NMR (300 MHz, dimethylsulfoxide-d$_6$) δ ppm 3.70 (s, 3 H) 3.75 (s, 3 H) 5.04 (s, 2 H) 5.14 (s, 2 H) 6.18 (dd, 1 H) 6.38 (d, 1 H) 6.47 (d, 1 H) 6.89 (m, 1 H) 7.12 (m, 3 H) 7.23 (s, 1 H) 7.35-7.50 (m, 6 H) 7.68 (d, 1 H) 8.16 (d, 1 H) 8.28 (s, 1 H) 9.40 (m, 1 H).

Example 47

2-{4-[(4-{2-[4-(benzyloxy)-3-methoxyphenyl]imidazo[1,2-a]pyridin-3-yl}pyrimidin-2-yl)amino]-1H-pyrazol-1-yl}ethanol The trifluoroacetic acid salt of the title compound was prepared as described in EXAMPLE 12K, substituting EXAMPLE 27A for EXAMPLE 12J. MS (ESI(+)) m/e 534.2

(M+H)+, 1H NMR (300 MHz, methanol-d4) δ ppm 3.86 (m, 5 H) 4.17 (m, 2 H) 5.21 (s, 2 H) 6.67 (m, 1 H) 7.20 (m, 2 H) 7.27 (s, 1 H) 7.32-7.41 (m, 3 H) 7.48 (m, 3 H) 7.63 (s, 1 H) 7.92-8.05 (m, 3 H) 8.36 (d, 1 H) 9.78 (brs, 1 H).

Example 48

2-[{4-[(4-{2-[4-(benzyloxy)-3-methoxyphenyl]imidazo[1,2-a]pyridin-3-yl}pyrimidin-2-yl)amino]-3-methoxyphenyl}(methyl)amino]ethanol Example 48A 2-((3-methoxy-4-nitrophenyl)(methyl)amino)ethanol The title compound was prepared as described in EXAMPLE 45A, substituting 2-(methylamino)ethanol for 1-amino-2-methylpropan-2-ol. MS (ESI(+)) m/e 226.9 (M+H)+

Example 48B 2-((4-amino-3-methoxyphenyl)(methyl)amino)ethanol

The title compound was prepared as described in EXAMPLE 12I, substituting EXAMPLE 48A for EXAMPLE 12H. MS (DCI(+)) m/e 197.1 (M+H)+.

Example 48C 2-((4-(4-(2-chloroimidazo[1,2-a]pyridin-3-yl)pyrimidin-2-ylamino)-3-methoxyphenyl)(methyl)amino)ethanol The title compound was prepared as described in EXAMPLE 12J, substituting EXAMPLE 48B for EXAMPLE 12I. MS (ESI(+)) m/e 425.0 (M+H)+.

Example 48D

2-[{4-[(4-{2-[4-(benzyloxy)-3-methoxyphenyl]imidazo[1,2-a]pyridin-3-yl}pyrimidin-2-yl)amino]-3-methoxyphenyl}(methyl)amino]ethanol The trifluoroacetic acid salt of the title compound was prepared as described in EXAMPLE 12K, substituting EXAMPLE 48C for EXAMPLE 12J. MS (ESI(+)) m/e 603.3 (M+H)+, 1H NMR (300 MHz, methanol-d4) δ ppm 3.25 (s, 3H) 3.64 (m, 4H) 3.86 (s, 3 H) 3.99 (s, 3 H) 5.20 (s, 2 H) 6.80 (d, 1 H) 6.93 (m, 1 H) 7.06 (brs, 1 H) 7.19 (m, 2 H) 7.32-7.49 (m, 7 H) 7.94 (m, 2 H) 8.09 (m, 1 H) 8.32 (d, 1 H) 9.76 (d, 1 H).

Example 49

4-{2-[4-(benzyloxy)-3-(trifluoromethyl)phenyl]imidazo[1,2-a]pyridin-3-yl}-N-{3-[2-(dimethylamino)ethyl]phenyl}pyrimidin-2-amine Example 49A 4-bromo-2-(trifluoromethyl)phenol A round-bottom flask with stirbar was charged with 2-(trifluoromethyl)phenol (1.7 g, 10.49 mmol) in 10 mL CH2Cl2 was cooled to 0° C. Bromine (0.540 ml, 10.49 mmol) in 2 mL CH2Cl2 was added dropwise. The reaction mixture was stirred at 0° C. for 1 hour, then allowed to warm to ambient temperature over 1 hour. Aqueous NaHSO3 solution was added, and the mixture extracted with CH2Cl2. The organic phase was washed with aqueous NaHCO3 and brine, dried (MgSO4), filtered, and concentrated. The residues were purified by flash chromatography eluting with 100% CH2Cl2, to afford the title compound. 1H NMR (300 MHz, dimethylsulfoxide-d6) δ ppm 10.90 (s, 1H), 7.63 (m, 1H), 6.98 (d, 1H).

Example 49B 1-(benzyloxy)-4-bromo-2-(trifluoromethyl)benzene

A round-bottom flask with stirbar was charged with EXAMPLE 49A (1.5 g, 6.22 mmol), Cs2CO3 (6.08 g, 18.67 mmol) and benzyl bromide (0.813 ml, 6.85 mmol) in 15 mL N,N-dimethylformamide. The mixture was stirred at ambient temperature for 16 hours, diluted with water and extracted with ethyl acetate. The organic phase was washed with brine, dried (MgSO4), filtered and concentrated. The residues were purified by silica gel chromatography eluting with 0-10% ethyl acetate/hexane, to afford the title compound. MS (ESI (+)) m/e 331.0 (M+H)+.

Example 49C 2-(4-(benzyloxy)-3-(trifluoromethyl)phenyl)-4,4,5,5-tetramethyl-1,3,2-dioxaborolane A 100 mL round bottom flask was charged with EXAMPLE 49B (1.90 g, 5.74 mmol), 4,4,4',4',5,5,5',5'-octamethyl-2,2'-bi(1,3,2-dioxaborolane) (1.75 g, 6.89 mmol), [1,1'-bis(diphenylphosphino)ferrocene]dichloropalladium (II) dichloromethane (0.234 g, 0.287 mmol), diphenylphosphinoferrocine (0.159 g, 0.287 mmol) and potassium acetate (1.689 g, 17.21 mmol) in 50 mL dioxane. The mixture was degassed with N2 and heated at 80° C. overnight, diluted with water, and extracted into ethyl acetate. The organics were washed with brine and dried (MgSO4), filtered, and concentrated. The crude product was purified on silica gel eluting with 0-10% ethyl acetate/hexane to provide the title compound. MS (DCI(+)) m/e 396 (M+NH4)+; 1H NMR (300 MHz, dimethylsulfoxide-d6) δ ppm 7.64 (dd, 1 H), 7.56-7.16 (m, 7 H), 5.26 (s, 2 H), 1.29 (s, 12 H).

Example 49D

4-{2-[4-(benzyloxy)-3-(trifluoromethyl)phenyl]imidazo[1,2-a]pyridin-3-yl}-N-{3-[2-(dimethylamino)ethyl]phenyl}pyrimidin-2-amine The title compound was prepared as described in EXAMPLE 12K, substituting EXAMPLE 49C for 4-(benzyloxy)-3-methoxyphenylboronic acid. MS (ESI(+)) m/e 609.3 (M+H)+; 1H NMR (500 MHz, dimethylsulfoxide-d6) δ ppm 9.73 (s, 1 H), 9.43 (s, 1 H), 8.40 (s, 1 H), 8.03-6.58 (m, 16 H), 5.33 (s, 2 H), 2.66 (s, 2 H), 2.51 (s, 2 H), 2.18 (s, 6 H).

Example 50

4-{2-[4-(benzyloxy)-3-ethylphenyl]imidazo[1,2-a]pyridin-3-yl}-N-{3-[2-(dimethylamino)ethyl]phenyl}pyrimidin-2-amine

Example 50A 1-(benzyloxy)-4-bromo-2-ethylbenzene

The title compound was prepared as described in EXAMPLE 49B, substituting 4-bromo-2-ethylphenol for EXAMPLE 49A. MS (ESI(+)) m/e 291.0 (M+H)$^+$.

Example 50B 2-(4-(benzyloxy)-3-ethylphenyl)-4,4,5,5-tetramethyl-1,3,2-dioxaborolane The title compound was prepared as described in EXAMPLE 49C, substituting EXAMPLE 50A for EXAMPLE 49B. MS (DCI(+)) m/e 356 (M+NH$_4$)$^+$; $^1$H NMR (300 MHz, dimethylsulfoxide-d$_6$) δ ppm 7.87-7.19 (m, 7 H), 7.03 (d, 1 H), 5.16 (s, 2 H), 2.61 (q, 2 H), 1.27 (s, 12 H), 1.14 (t, 3 H).

Example 50C

4-{2-[4-(benzyloxy)-3-ethylphenyl]imidazo[1,2-a]pyridin-3-yl}-N-{3-[2-(dimethylamino)ethyl]phenyl}pyrimidin-2-amine The title compound was prepared as described in EXAMPLE 12K, substituting EXAMPLE 50B for 4-(benzyloxy)-3-methoxyphenylboronic acid. MS (ESI(+)) m/e 569.3 (M+H)$^+$; $^1$H NMR (500 MHz, dimethylsulfoxide-d$_6$) δ ppm 9.57 (s, 1 H) 9.63-9.71 (m, 1 H), 8.34 (d, 1 H), 7.73 (d, 1 H), 7.64 (s, 1 H), 7.58 (d, 1 H), 7.54-7.32 (m, 8 H), 7.20 (t, 1 H), 7.13 (d, 1 H), 7.05 (t, 1 H), 6.85 (d, 1 H), 6.65 (d, 1 H), 5.18 (s, 2 H), 2.58-2.71 (m, 4 H), 2.47-2.39 (m, 2 H), 2.15 (s, 6 H), 1.14 (t, 3 H).

Example 51

4-{2-[4-(benzyloxy)-3-methoxyphenyl]imidazo[1,2-a]pyridin-3-yl}-N-(2-methoxy-4-thiomorpholin-4-ylphenyl)pyrimidin-2-amine

Example 51A 4-(3-methoxy-4-nitrophenyl)thiomorpholine

In a 50 mL round-bottomed flask was charged 4-fluoro-2-methoxy-1-nitrobenzene (1.05 g, 6.14 mmol), thiomorpholine (1.164 ml, 12.27 mmol), and Hunig's Base (1.072 ml, 6.14 mmol) in acetonitrile (20.45 ml). The reaction was heated at 85° C. for three days. The mixture was concentrated and the residue was placed on a silica gel column. The product was eluted from the column with dichloromethane to give the title compound. MS (DCI(+)) m/e 255.1 (M+H)$^+$.

Example 51B 2-methoxy-4-thiomorpholinoaniline

Into a 50 ml round-bottomed flask was charged EXAMPLE 51A (0.945 g, 3.72 mmol), iron (1.038 g, 18.58 mmol), and ammonium chloride (0.109 g, 2.044 mmol) in ethanol (16.99 ml) and water (4.25 ml). The suspension was heated for three hours and then diluted with methanol. The mixture was filtered saving the filtrate and discarding the excess iron. After solvent removal, the solid was redissolved in dichloromethane and washed with water. The organic phase was dried over magnesium sulfate, filtered and the solvent was removed and the solids were dried under vacuum to provide the title compound. MS (DCI(+)) m/e 225.0 (M+H)$^+$.

Example 51C 4-(2-chloroimidazo[1,2-a]pyridin-3-yl)-N-(2-methoxy-4-thiomorpholinophenyl)pyrimidin-2-amine Into a 4 ml vial was charged EXAMPLE 12G (0.1 g, 0.377 mmol), EXAMPLE 51B (0.085 g, 0.377 mmol), and 4 M hydrochloric acid in dioxane (0.085 ml, 0.339 mmol) in 2-propanol (1.886 ml). The mixture was heated at 100° C. for 20 hours stirring on a hot plate. The reaction mixture was allowed to cool, filtered, and solid was dried under vacuum. MS (ESI(+)) m/e 453 (M+H)$^+$; (ESI(−)) m/e 451 (M−H)$^-$.

Example 51D

4-{2-[4-(benzyloxy)-3-methoxyphenyl]imidazo[1,2-a]pyridin-3-yl}-N-(2-methoxy-4-thiomorpholin-4-ylphenyl)pyrimidin-2-amine The title compound was prepared as a trifluoroacetic acid salt, as described in EXAMPLE 12K, substituting EXAMPLE 51C for EXAMPLE 12J. (ESI(+)) m/e 631 (M+H)$^+$; (ESI(−)) m/e 629 (M−H)$^-$; $^1$H-NMR (300 MHz, dimethylsulfoxide-d$_6$) δ 9.56 (s, 1 H), 8.87 (s, 1 H), 8.24 (d, 1 H), 7.82 (d, 1 H), 7.62-7.74 (m, 1 H), 7.31-7.54 (m, 6 H), 7.26 (s, 1 H), 7.11-7.22 (m, 3 H), 6.72 (d, 1 H), 6.47-6.61 (m, 2 H), 5.16 (s, 2 H), 3.82 (s, 3 H), 3.76 (s, 3 H), 3.52-3.60 (m, 4 H), 2.68-2.76 (m, 4 H).

Example 52

4-{2-[4-(benzyloxy)-3-methoxyphenyl]imidazo[1,2-a]pyridin-3-yl}-N-(2-methoxy-5-morpholin-4-ylphenyl)pyrimidin-2-amine

Example 52A 4-(4-methoxy-3-nitrophenyl)morpholine

Into a 20 ml vial was charged 4-bromo-1-methoxy-2-nitrobenzene (0.3 g, 1.293 mmol), morpholine (0.338 ml, 3.88 mmol), tris(dibenzylideneacetone)dipalladium(0) (0.059 g, 0.065 mmol), xantphos (0.037 g, 0.065 mmol) and sodium tert-butoxide (0.311 g, 3.23 mmol) in 1,4-dioxane (12.93 ml). The reaction mixture was heated at 100° C. on a hot plate for 2 hours. The solution was allowed to cool and stir overnight at room temperature. The mixture was concentrated and the residue was loaded onto a silica gel column. The compound was eluted using a gradient starting with 100% dichloromethane to 1:1 dichloromethane/methanol over 50 minutes to provide the title compound. MS (DCI(+)) m/e 239.0 (M+H)$^+$.

Example 52B 2-methoxy-5-morpholinoaniline

Into a 50 ml pressure bottle was charged EXAMPLE 52A (0.2476 g, 1.039 mmol), tetrahydrofuran (2 ml), ethanol (2 ml), hydrogen (30 psi), and 5% Pd—C, wet (0.050 g, 0.465 mmol). The mixture was stirred for 3 hours at room temperature, filtered through a nylon membrane and concentrated to provide the title compound. MS (DCI(+)) m/e 209.0 (M+H)+.

Example 52C 4-(2-chloroimidazo[1,2-a]pyridin-3-yl)-N-(2-methoxy-5-morpholinophenyl)pyrimidin-2-amine The title compound was prepared as described in EXAMPLE 51C, substituting EXAMPLE 52B for EXAMPLE 51B. MS (ESI(+)) m/e 437.0 (M+H)+; (ESI(−)) m/e 435.0 (M−H)−.

Example 52D

4-{2-[4-(benzyloxy)-3-methoxyphenyl]imidazo[1,2-a]pyridin-3-yl}-N-(2-methoxy-5-morpholin-4-ylphenyl)pyrimidin-2-amine The title compound was prepared as a trifluoroacetic acid salt, as described in EXAMPLE 12K, substituting EXAMPLE 52C for EXAMPLE 12J. (ESI(+)) m/e 615 (M+H)+; (ESI(−)) m/e 613 (M−H)−; $^1$H-NMR (300 MHz, dimethylsulfoxide-$d_6$) δ 9.52 (d, 1 H), 8.72 (s, 1 H), 8.38 (d, 1 H), 7.81-7.87 (m, 1 H), 7.66-7.75 (m, 1 H), 7.63 (s, 1 H), 7.46-7.54 (m, 2 H), 7.32-7.45 (m, 3 H), 7.26 (s, 1 H), 7.16-7.23 (m, 3 H), 7.04 (d, 1 H), 6.76 (dd, 1 H), 6.69 (d, 1 H), 5.16 (s, 2 H), 3.81 (s, 3 H), 3.75 (s, 3 H), 3.65-3.72 (m, 4 H), 2.94-3.03 (m, 4 H).

Example 53

N-{4-[(4-{2-[4-(benzyloxy)-3-methoxyphenyl]imidazo[1,2-a]pyridin-3-yl}pyrimidin-2-yl)amino]-3-methoxyphenyl}glycine Example 53A tert-butyl 2-(3-methoxy-4-nitrophenylamino)acetate The title compound was prepared as described in EXAMPLE 45A, substituting tert-butyl 2-aminoacetate for 1-amino-2-methylpropan-2-ol. MS (ESI(+)) m/e 282.9 (M+H)+.

Example 53B tert-butyl 2-(4-amino-3-methoxyphenylamino)acetate

EXAMPLE 53A (0.466 g, 1.651 mmol) in methanol (5 mL) was added to 5% Pd/C (wet, 0.093 g) in a 20 mL pressure bottle and stirred under 60 psi of hydrogen at 50° C. for 1 hour. The mixture was filtered through a polypropylene membrane filter, and the filtrate was concentrated to provide the title compound. MS (DCI(+)) m/e 253.1 (M+H)+.

Example 53C tert-butyl 2-(4-(4-(2-chloroimidazo[1,2-a]pyridin-3-yl)pyrimidin-2-ylamino)-3-methoxyphenylamino)acetate A 5 mL reaction vial equipped with a stir bar was charged with EXAMPLE 12G (0.225 g, 0.849 mmol), EXAMPLE 53B (0.236 g, 0.934 mmol) and Hunig's base (0.296 mL, 1.697 mmol) in N-methyl-2-pyrrolidinone (3.6 ml) and sealed. The reaction was heated on a thermal block at 95° C. for 60 hours. The reaction was cooled to ambient temperature and diluted with 60 mL water. The resulting suspension was filtered. The solid collected was washed with water and dried under vacuum. The residue was purified by flash chromatography on a 10 g silica gel column eluting with a gradient of from 0% to 30% ethyl acetate/hexanes to provide the title compound. MS (ESI(+)) m/e 481.0 (M+H)+.

Example 53D

N-{4-[(4-{2-[4-(benzyloxy)-3-methoxyphenyl]imidazo[1,2-a]pyridin-3-yl}pyrimidin-2-yl)amino]-3-methoxyphenyl}glycine A 2 mL Biotage microwave reaction vial was charged with EXAMPLE 53C (0.045 g, 0.094 mmol), 4-(benzyloxy)-3-methoxyphenylboronic acid (0.027 g, 0.103 mmol), cesium fluoride (0.043 g, 0.281 mmol), 1,2-dimethoxyethane (0.8 mL) and methanol (0.4 mL). The mixture was treated with tetrakis(triphenylphosphine)palladium(0) (5.4 mg, 0.005 mmol) and the vessel was sealed under nitrogen. The reaction was heated at 155° C. for 35 minutes on a Biotage Initiator microwave reactor. The reaction mixture was cooled to ambient temperature, treated with 0.14 mL 2M NaOH, and stirred for 4 hours. The reaction was concentrated and purified by reverse-phase HPLC on a Phenomenex C18 column (3×15 cm) using a gradient of acetonitrile in 0.15% aqueous trifluoroacetic acid to provide the title compound as a trifluoroacetic acid salt. MS (ESI(+)) m/e 603.2 (M+H)+, $^1$H NMR (300 MHz, methanol-$d_4$) δ ppm 3.82 (s, 3 H) 3.87 (s, 3 H) 3.97 (s, 2 H) 5.21 (s, 2 H) 6.30 (m, 1 H) 6.48 (m, 1 H) 6.64 (d, 1 H) 7.19 (m, 2 H) 7.26-7.41 (m, 6 H) 7.47 (m, 2 H) 7.82 (m, 2 H) 8.00 (m, 1 H) 9.82 (brs, 1 H).

Example 54

4-{2-[4-(benzyloxy)-3-methoxyphenyl]imidazo[1,2-a]pyridin-3-yl}-N-[1-(2-piperidin-1-ylethyl)-1H-pyrazol-4-yl]pyrimidin-2-amine Example 54A N,N-dimethyl-2-(4-nitro-1H-pyrazol-1-yl)ethanamine The title compound was prepared as described in EXAMPLE 37A, substituting N-(2-chloroethyl)piperidine hydrochloride for N-(2-chloroethyl)pyrrolidine hydrochloride. MS (ESI(+)) m/e 224.9 (M+H)+.

Example 54B 1-(2-(piperidin-1-yl)ethyl)-1H-pyrazol-4-amine

The title compound was prepared as the hydrochloride salt as described in EXAMPLE 37B, substituting EXAMPLE 54A for EXAMPLE 37A. MS (ESI(+)) m/e 195.0 (M+H)+.

Example 54C 4-(2-chloroimidazo[1,2-a]pyridin-3-yl)-N-(1-(2-(piperidin-1-yl)ethyl)-1H-pyrazol-4-yl)pyrimidin-2-amine The title compound was prepared as described in EXAMPLE 12J, substituting EXAMPLE 54B for EXAMPLE 12I. MS (ESI(+)) m/e 423.0 (M+H)+.

Example 54D

4-{2-[4-(benzyloxy)-3-methoxyphenyl]imidazo[1,2-a]pyridin-3-yl}-N-[1-(2-piperidin-1-ylethyl)-1H-pyrazol-4-yl]pyrimidin-2-amine The title compound was prepared as described in EXAMPLE 12K, substituting EXAMPLE 54C for EXAMPLE 12J. MS (ESI(+)) m/e 601.3 (M+H)$^+$; $^1$H NMR (300 MHz, dimethylsulfoxide-$d_6$) δ ppm 9.80-9.20 (br, 1 H) 9.58 (s, 1 H) 8.33 (d, 1 H) 7.93 (s, 1 H) 7.73 (d, 1 H) 7.30-7.54 (m, 7 H) 7.27 (d, 1 H) 7.09-7.20 (m, 2 H) 7.06 (t, 1 H) 6.60 (d, 1 H) 5.13 (s, 2 H) 4.03-4.20 (m, 2 H) 3.74 (s, 3 H) 2.61 (t, 2 H) 2.38-2.29 (m, 4 H) 1.27-1.51 (m, 6 H).

Example 55

4-{2-[4-(benzyloxy)-3-methoxyphenyl]imidazo[1,2-a]pyridin-3-yl}-N-[1-(2-morpholin-4-ylethyl)-1H-pyrazol-4-yl]pyrimidin-2-amine

Example 55A 4-(2-(4-nitro-1H-pyrazol-1-yl)ethyl)morpholine

The title compound was prepared as described in EXAMPLE 37A, substituting 4-(2-chloroethyl)morpholine hydrochloride for N-(2-chloroethyl)pyrrolidine hydrochloride. MS (ESI(+)) m/e 226.9 (M+H)$^+$.

Example 55B 1-(2-morpholinoethyl)-1H-pyrazol-4-amine

The title compound was prepared as the hydrochloride salt as described in EXAMPLE 37B, substituting EXAMPLE 55A for EXAMPLE 37A. MS (ESI(+)) m/e 196.9 (M+H)$^+$.

Example 55C 4-(2-chloroimidazo[1,2-a]pyridin-3-yl)-N-(1-(2-morpholinoethyl)-1H-pyrazol-4-yl)pyrimidin-2-amine The title compound was prepared as described in EXAMPLE 12J, substituting EXAMPLE 55B for EXAMPLE 12I. MS (ESI(+)) m/e 425.0 (M+H)$^+$.

Example 55D

4-{2-[4-(benzyloxy)-3-methoxyphenyl]imidazo[1,2-a]pyridin-3-yl}-N-[1-(2-morpholin-4-ylethyl)-1H-pyrazol-4-yl]pyrimidin-2-amine The title compound was prepared as described in EXAMPLE 12K, substituting EXAMPLE 55C for EXAMPLE 12J. MS ESI(+)) m/e 603.3 (M+H)$^+$; $^1$H NMR (300 MHz, dimethylsulfoxide-$d_6$) δ ppm 9.80-9.10 (br, 1 H) 9.58 (s, 1 H) 8.33 (d, 1 H) 7.93 (s, 1 H) 7.74 (d, 1 H) 7.31-7.54 (m, 7 H) 7.26 (s, 1 H) 7.10-7.21 (m, 2 H) 7.06 (t, 1 H) 6.60 (d, 1 H) 5.13 (s, 2 H) 4.06-4.27 (m, 2 H) 3.74 (s, 3 H) 3.55-3.46 (s, 4 H) 2.67 (t, 2 H) 2.42-2.34 (s, 4 H).

Example 56

4-{2-[4-(benzyloxy)-3-methoxyphenyl]imidazo[1,2-a]pyridin-3-yl}-N-[2-methoxy-4-(4-thiomorpholin-4-ylpiperidin-1-yl)phenyl]pyrimidin-2-amine

Example 56A 4-(1-(3-methoxy-4-nitrophenyl)piperidin-4-yl)thiomorpholine

Into a 2 mL microwave tube was placed 4-(piperidin-4-yl)thiomorpholine (0.030 g, 0.159 mmol), 4-(piperidin-4-yl)thiomorpholine (0.030 g, 0.159 mmol), and Hunig's Base (0.097 ml, 0.556 mmol) in acetonitrile (0.353 ml) and N-methylmorpholine (0.177 ml). The reaction was heated at 130° C. in Biotage microwave reactor for 1 hour. The reaction was checked by HPLC, and starting material still remained. To the suspension was added 2 more equivalents of Hunig's base (0.056 ml, 0.318 mmol) and the reaction was heated for another hour at 130° C. The mixture was diluted with acetonitrile containing 0.15% trifluoroacetic acid and passed through a syringe filter. The crude material was purified by reverse phase HPLC using 0.15% trifluoroacetic acid. MS (DCI(+)) m/e 338.3 (M+H)$^+$.

Example 56B 2-methoxy-4-(4-thiomorpholinopiperidin-1-yl)aniline

The title compound was prepared as described in EXAMPLE 51B, substituting EXAMPLE 56A for EXAMPLE 51A. MS (DCI(+)) m/e 308.2 (M+H)$^+$.

Example 56C 2-methoxy-4-(4-thiomorpholinopiperidin-1-yl)aniline

The title compound was prepared as described in EXAMPLE 51C, substituting EXAMPLE 56B for EXAMPLE 51B. MS (ESI(+)) m/e 536.1 (M+H)$^+$; (ESI(−)) m/e 534.1 (M−H)$^-$.

Example 56D

4-{2-[4-(benzyloxy)-3-methoxyphenyl]imidazo[1,2-a]pyridin-3-yl}-N-[2-methoxy-4-(4-thiomorpholin-4-ylpiperidin-1-yl)phenyl]pyrimidin-2-amine The title compound was prepared as a trifluoroacetic acid salt, as described in EXAMPLE 12K, substituting EXAMPLE 56C for EXAMPLE 12J. (ESI(+)) m/e 714 (M+H)$^+$; (ESI(−)) m/e 712 (M−H)$^-$; $^1$H NMR (300 MHz, dimethylsulfoxide-$d_6$) δ 9.44 (d, 2 H), 8.59 (s, 1 H), 8.24 (d, 1 H), 7.75 (d, 1 H), 7.31-7.60 (m, 7H), 7.24 (s, 1 H), 7.15 (s, 1 H), 6.99-7.10 (m, 1 H), 6.73 (d, 1 H), 6.51-6.60 (m, 2 H), 5.14 (s, 2 H), 3.90 (d, 2 H), 3.82 (s, 3 H), 3.73-3.78 (m, 4 H), 3.16-3.33 (m, 4 H), 2.97-3.11 (m, 2 H), 2.85-2.97 (m, 2 H), 2.73 (t, 2 H), 2.09 (d, 2 H), 1.70-1.89 (m, 2 H).

Example 57

4-{2-[4-(benzyloxy)-3-methoxyphenyl]imidazo[1,2-a]pyridin-3-yl}-N-(2-methoxy-4-piperidin-4-ylphenyl)pyrimidin-2-amine

Example 57A tert-butyl 4-(3-methoxy-4-nitrophenyl)-5,6-dihydropyridine-1(2H)-carboxylate Into a 5 mL microwave tube was charged tert-butyl 4-(4,4,5,5-tetramethyl-1,3,2-dioxaborolan-2-yl)-5,6-dihydropyridine-1(2H)-carboxylate (0.247 g, 0.800 mmol), 4-chloro-2-methoxy-1-nitrobenzene (0.100 g, 0.533 mmol), dichlorobis(triphenylphosphine)palladium (II) (0.019 g, 0.027 mmol), sodium carbonate (0.113 g, 1.066 mmol) in water (0.889 ml) and dimethoxyethane (2.3 ml). The reaction mixture was heated at 130° C. for 20 minutes in a Biotage microwave reactor. The solids were filtered off and the filtrate was purified by reverse phase HPLC using 0.1% ammonium hydroxide. MS (DCI(+)) m/e 335.2 (M+H)$^+$.

Example 57B tert-butyl 4-(4-amino-3-methoxyphenyl)piperidine-1-carboxylate

Into a 4 ml pressure bottle was charged EXAMPLE 57A (0.2476 g, 1.039 mmol), tetrahydrofuran (2 ml), ethanol (2 ml), hydrogen (60 psi), and 5% Pd—C, wet (0.050 g, 0.465 mmol). The mixture was stirred for 2 hours at 50° C. and then 2.5 days at room temperature. The mixture was filtered through a nylon membrane and concentrated. MS DCI(+)) m/e 307.3 (M+H)$^+$.

Example 57C 4-(2-chloroimidazo[1,2-a]pyridin-3-yl)-N-(2-methoxy-4-(piperidin-4-yl)phenyl)pyrimidin-2-amine The title compound was prepared as described in EXAMPLE 51C, substituting EXAMPLE 57B for EXAMPLE 51B. MS (DCI(+)) m/e 435.3 (M+H)$^+$.

Example 57D

4-{2-[4-(benzyloxy)-3-methoxyphenyl]imidazo[1,2-a]pyridin-3-yl}-N-(2-methoxy-4-piperidin-4-ylphenyl)pyrimidin-2-amine The title compound was prepared as a trifluoroacetic acid salt, as described in EXAMPLE 12K, substituting EXAMPLE 57C for EXAMPLE 12J. (ESI(+)) m/e 613 (M+H)$^+$; (ESI(−)) m/e 611 (M−H)$^-$; $^1$H NMR (300 MHz, dimethylsulfoxide-d$_6$) δ 9.47 (d, 1 H), 8.61 (s, 1 H), 8.48-8.59 (m, 1 H), 8.18-8.35 (m, 2 H), 7.76 (d, 2 H), 7.31-7.58 (m, 6H), 7.24 (s, 1 H), 7.15 (s, 2 H), 7.03 (t, 1 H), 6.95 (d, 1 H), 6.81 (dd, 1 H), 6.64 (d, 1 H), 5.14 (s, 2 H), 3.86 (s, 3 H), 3.75 (s, 3 H), 2.77-3.12 (m, 4 H), 1.93-2.05 (m, 2 H), 1.70-1.92 (m, 2 H).

Example 58

4-{2-[4-(benzyloxy)-3-(trifluoromethoxy)phenyl]imidazo[1,2-a]pyridin-3-yl}-N-[3-(2-pyrrolidin-1-ylethyl)phenyl]pyrimidin-2-amine

Example 58A 4-bromo-2-(trifluoromethoxy)phenol

The title compound was prepared as described in EXAMPLE 49B, substituting 2-(trifluoromethoxy)phenol for 2-(trifluoromethyl)phenol. MS (ESI(−)) m/e 254.8 (M−H)$^-$.

Example 58B 1-(benzyloxy)-4-bromo-2-(trifluoromethoxy)benzene

The title compound was prepared as described in EXAMPLE 49B, substituting EXAMPLE 58A for EXAMPLE 49A. MS (ESI(+)) m/e 347.0 (M+H)$^+$.

Example 58C 2-(4-(benzyloxy)-3-(trifluoromethoxy)phenyl)-4,4,5,5-tetramethyl-1,3,2-dioxaborolane The title compound was prepared as described in EXAMPLE 49C, substituting EXAMPLE 58B for EXAMPLE 49B. MS (DCI(+)) m/e 412 (M+NH$_4$)$^+$; $^1$H NMR (300 MHz, dimethylsulfoxide-d$_6$) δ ppm 7.64 (dd, 1 H), 7.56-7.16 (m, 7H), 5.26 (s, 2 H), 1.29 (s, 12 H).

Example 58D

4-{2-[4-(benzyloxy)-3-(trifluoromethoxy)phenyl]imidazo[1,2-a]pyridin-3-yl}-N-[3-(2-pyrrolidin-1-ylethyl)phenyl]pyrimidin-2-amine The title compound was prepared as described in EXAMPLE 12K, substituting EXAMPLE 58C for 4-(benzyloxy)-3-methoxyphenylboronic acid, and substituting EXAMPLE 24A for EXAMPLE 12J. MS (ESI(+)) m/e 651.3 (M+H)$^+$; $^1$H NMR (500 MHz, dimethylsulfoxide-d$_6$) δ ppm 9.73 (s, 1 H), 9.43 (d, 1 H) 8.39 (s, 1 H), 7.94-6.55 (m, 16 H), 5.28 (s, 2 H), 2.70 (s, 4 H), 2.50 (s, 4 H), 1.68 (s, 4 H).

Example 59

4-{2-[4-(benzyloxy)-3-methoxyphenyl]imidazo[1,2-a]pyridin-3-yl}-N-{5-[2-(dimethylamino)ethyl]-2-methoxyphenyl}pyrimidin-2-amine

Example 59A 4-(2-bromoethyl)-1-methoxy-2-nitrobenzene

Into a 500 mL pear flask was charged 4-methoxyphenethyl bromide (0.727 ml, 4.65 mmol) in trifluoroacetic acid (9.30 ml). The solution was cooled to 0° C. In a 50 mL Erlenmeyer flask was added nitric acid (0.231 ml, 4.65 mmol) and trifluoroacetic acid (2.0 mL). The nitric acid solution was added to the reaction dropwise via syringe. The reaction was stirred at room temperature for 2 hours. The solvent was removed on a rotovap and the residue taken up into ethyl acetate. The reaction was washed with 1N HCl, saturated aqueous sodium bicarbonate, and brine, dried over $MgSO_4$, filtered and concentrated onto silica gel. The reaction was purified by flash chromatography (10% ethyl acetate:hexanes for 20 minutes, then to 50% ethyl acetate:hexanes over 20 minutes) to provide the title compound. MS (DCI) m/e 277 $(M+NH_4)$.

Example 59B 2-(4-methoxy-3-nitrophenyl)-N,N-dimethylethanamine

Into a 100 mL round-bottomed flask was charged EXAMPLE 59A (1.0318 g, 3.97 mmol). Triethylamine (1.659 ml, 11.90 mmol) and dimethylamine (5.95 ml, 11.90 mmol, 2.0M in tetrahydrofuran) were added. The reaction was stirred overnight at room temperature. The reaction was partitioned between ethyl acetate and saturated aqueous sodium bicarbonate, dried over $MgSO_4$, filtered and concentrated. The residue was purified by flash chromatography (100% $CH_2Cl_2$ to 90:9:1 $CH_2Cl_2$:methanol:$NH_4OH$ over 20 minutes) to provide the title compound. MS (DCI) m/e 225 $(M+H)^+$.

Example 59C 5-(2-(dimethylamino)ethyl)-2-methoxyaniline

Into a 250 mL round-bottomed flask was charged EXAMPLE 59B (0.582 g, 2.60 mmol), iron (1.594 g, 28.5 mmol), ammonium chloride (0.167 g, 3.11 mmol), ethanol (10.38 ml) and water (2.60 ml). The reaction was heated to 90° C. for 1 hour, then filtered hot and rinsed with ethyl acetate. The filtrate was washed with saturated aqueous sodium bicarbonate and brine, dried over $MgSO_4$, filtered, and concentrated to provide the title compound. MS (DCI) m/e 195 $(M+H)^+$.

Example 59D 4-(2-chloroimidazo[1,2-a]pyridin-3-yl)-N-(5-(2-(dimethylamino)ethyl)-2-methoxyphenyl)pyrimidin-2-amine The title compound was prepared as described in EXAMPLE 12J, substituting EXAMPLE 59C for EXAMPLE 12I. MS (ESI) m/e 423 $(M+H)^+$.

Example 59E

4-{2-[4-(benzyloxy)-3-methoxyphenyl]imidazo[1,2-a]pyridin-3-yl}-N-{5-[2-(dimethylamino)ethyl]-2-methoxyphenyl}pyrimidin-2-amine The title compound was prepared as described in EXAMPLE 12K, substituting EXAMPLE 59D for EXAMPLE 12J. MS (ESI) m/e 601 $(M+H)^+$; $^1H$ NMR (300 MHz, dimethylsulfoxide-$d_6$) δ 9.40 (d, 1H), 8.43 (s, 1H), 8.32 (d, 1H), 7.78 (d, 1H), 7.72 (m, 1H), 7.47 (m, 4H), 7.39 (m, 3H), 7.31 (m, 1H), 7.25 (m, 1H), 7.13 (m, 1H), 6.99 (m, 3H), 6.64 (d, 1H), 5.13 (s, 2H), 3.83 (s, 3H), 3.74 (s, 3H), 2.62 (m, 2H), 2.37 (m, 2H), 2.11 (s, 6H).

Example 60

N-(4-{2-[4-(benzyloxy)-3-methoxyphenyl]imidazo[1,2-a]pyridin-3-yl}pyrimidin-2-yl)-2-methyl-1,2,3,4-tetrahydroisoquinolin-7-amine

Example 60A 2-methyl-7-nitro-1,2,3,4-tetrahydroisoquinoline

Into a 125 mL Erlenmeyer flask was charged 7-nitro-1,2,3,4-tetrahydroisoquinoline, hydrochloric acid (3.17 g, 14.77 mmol) in dichloroethane (148 ml). The solution was stirred 10 minutes with 1 N NaOH, and the layers were separated. Paraformaldehyde (2.217 g, 73.8 mmol), acetic acid (4.23 ml, 73.8 mmol) and sodium cyanoborohydride (4.64 g, 73.8 mmol) were added. The reaction was heated at 90° C. overnight. The reaction was cooled to room temperature, and quenched with saturated aqueous sodium bicarbonate. The layers were separated, and the organic layer was dried over $MgSO_4$, filtered, and concentrated onto silica gel. The reaction was purified by flash chromatography (50% ethyl acetate:hexanes for 20 minutes, then to 100% ethyl acetate:hexanes over 30 minutes) to provide the title compound. MS (DCI) m/e 193 $(M+H)^+$.

Example 60B 2-methyl-1,2,3,4-tetrahydroisoquinolin-7-amine

EXAMPLE 60A (2.35 g, 12.23 mmol) and ethyl acetate (40 ml) were added to 10% Pd—C, dry (0.235 g, 2.208 mmol) in a 250 mL stainless steel pressure bottle and stirred under $H_2$ for 16 hours at 30 psi and room temperature. The mixture was filtered through a nylon membrane and concentrated to provide the title compound. MS (DCI) m/e 163 $(M+H)^+$.

Example 60C

N-(4-(2-chloroimidazo[1,2-a]pyridin-3-yl)pyrimidin-2-yl)-2-methyl-1,2,3,4-tetrahydroisoquinolin-7-amine The title compound was prepared as described in EXAMPLE 12J, substituting EXAMPLE 60B for EXAMPLE 12I. MS (ESI) m/e 391 $(M+H)^+$.

Example 60D

N-(4-{2-[4-(benzyloxy)-3-methoxyphenyl]imidazo[1,2-a]pyridin-3-yl}pyrimidin-2-yl)-2-methyl-1,2,3,4-tetrahydroisoquinolin-7-amine The title compound was prepared as described in EXAMPLE 12K, substituting EXAMPLE 60C for EXAMPLE 12J. MS (ESI) m/e 569 $(M+H)^+$; $^1H$ NMR (300 MHz, dimethylsulfoxide-$d_6$) δ 9.60 (s, 1H), 9.55 (d, 1H), 8.34 (d, 1H), 7.72 (d, 1H), 7.47 (m, 5H), 7.38 (m, 3H), 7.26 (d, 1H), 7.15 (m, 2H), 7.04 (m, 2H), 6.66 (d, 1H), 5.13 (s, 2H), 3.75 (s, 3H), 3.41 (m, 2H), 2.76 (m, 2H), 2.58 (t, 2H), 2.32 (s, 3H).

Example 61

N-(4-{2-[4-(benzyloxy)-3-methoxyphenyl]imidazo[1,2-a]pyridin-3-yl}pyrimidin-2-yl)-1,2,3,4-tetrahydroisoquinolin-6-amine

Example 61A

N-(4-(2-chloroimidazo[1,2-a]pyridin-3-yl)pyrimidin-2-yl)-1,2,3,4-tetrahydroisoquinolin-6-amine The title compound was prepared as described in EXAMPLE 12J, substituting tert-butyl 6-amino-3,4-dihydroisoquinoline-2(1H)-carboxylate for EXAMPLE 12I. MS (ESI) m/e 377 (M+H)$^+$.

Example 61B

N-(4-{2-[4-(benzyloxy)-3-methoxyphenyl]imidazo[1,2-a]pyridin-3-yl}pyrimidin-2-yl)-1,2,3,4-tetrahydroisoquinolin-6-amine The title compound was prepared as described in EXAMPLE 12K, substituting EXAMPLE 61A for EXAMPLE 12J. MS (ESI) m/e 555 (M+H)$^+$; $^1$H NMR (300 MHz, dimethylsulfoxide-d$_6$) δ 9.57 (m, 2H), 8.34 (d, 1H), 7.73 (d, 1H), 7.50 (m, 4H), 7.42 (m, 5H), 7.26 (m, 1H), 7.15 (m, 2H), 7.04 (m, 1H), 6.93 (m, 1H), 6.65 (d, 1H), 5.14 (s, 2H), 3.79 (m, 2H), 3.74 (s, 3H), 2.92 (m, 2H), 2.62 (m, 2H).

Example 62

N-(4-{2-[4-(benzyloxy)-3-methoxyphenyl]imidazo[1,2-a]pyridin-3-yl}pyrimidin-2-yl)-1,2,3,4-tetrahydroisoquinolin-7-amine

Example 62A

N-(4-(2-chloroimidazo[1,2-a]pyridin-3-yl)pyrimidin-2-yl)-1,2,3,4-tetrahydroisoquinolin-7-amine The title compound was prepared as described in EXAMPLE 12J, substituting tert-butyl 7-amino-3,4-dihydroisoquinoline-2(1H)-carboxylate for EXAMPLE 12I. MS (ESI) m/e 377 (M+H)$^+$.

Example 62B

N-(4-{2-[4-(benzyloxy)-3-methoxyphenyl]imidazo[1,2-a]pyridin-3-yl}pyrimidin-2-yl)-1,2,3,4-tetrahydroisoquinolin-7-amine The title compound was prepared as described in EXAMPLE 12K, substituting EXAMPLE 62A for EXAMPLE 12J. MS (ESI) m/e 555 (M+H)$^+$; $^1$H NMR (300 MHz, dimethylsulfoxide-d$_6$) δ 9.57 (m, 2H), 8.33 (d, 1H), 7.73 (d, 1H), 7.47 (m, 5H), 7.39 (m, 4H), 7.26 (m, 1H), 7.16 (m, 2H), 7.05 (m, 1H), 6.98 (m, 1H), 6.65 (d, 1H), 5.14 (s, 2H), 3.78 (m, 2H), 3.75 (s, 3H), 2.93 (m, 2H), 2.63 (m, 2H).

Example 63

4-{2-[4-(benzyloxy)-3-methoxyphenyl]imidazo[1,2-a]pyridin-3-yl}-N-[4-(1,1-dioxidothiomorpholin-4-yl)-2-methoxyphenyl]pyrimidin-2-amine In a 4 ml vial were charged EXAMPLE 51D (0.0406 g, 0.064 mmol) and 3-chloroperbenzoic acid (0.037 g, 0.161 mmol) in dichloromethane (0.644 ml). The reaction mixture was stirred at room temperature overnight. The reaction mixture was diluted with methanol and passed through syringe filter. The filtrate was purified by reverse phase HPLC using 0.15% TFA to give the title compound as a trifluoroacetic acid salt. (ESI(+)) m/e 663 (M+H)$^+$; (ESI(−)) m/e 661 (M−H)$^-$; $^1$H NMR (500 MHz, dimethylsulfoxide-d$_6$) δ 9.60 (d, 1 H), 8.89 (s, 1 H), 8.43 (d, 1 H), 8.32 (d, 1 H), 7.81 (d, 1 H), 7.71 (d, 1 H), 7.65 (dd, 1 H), 7.58-7.63 (m, 1 H), 7.46-7.51 (m, 2 H), 7.42 (t, 2 H), 7.33-7.39 (m, 1 H), 7.26 (s, 1 H), 7.17-7.22 (m, 1 H), 7.17 (s, 2 H), 6.79 (d, 1 H), 5.15 (s, 2 H), 4.73 (t, 2 H), 4.13 (d, 2 H), 4.04 (s, 3 H), 3.75 (s, 3 H), 3.62-3.68 (m, 2 H), 3.33 (d, 2 H).

Example 64

2-[{3-[(4-{2-[4-(benzyloxy)-3-methoxyphenyl]imidazo[1,2-a]pyridin-3-yl}pyrimidin-2-yl)amino]-4-methoxybenzyl}(methyl)amino]ethanol

Example 64A 2-((4-methoxy-3-nitrobenzyl)(methyl)amino)ethanol

A 5 mL round bottom flask was charged with 4-(bromomethyl)-1-methoxy-2-nitrobenzene (0.6 g, 2.44 mmol) and acetonitrile (2 mL). The solution was treated with triethylamine (1 mL, 7.32 mmol) and 2-(methylamino)ethanol (0.585 mL, 7.32 mmol) and the reaction was stirred at ambient temperature for 16 hours. The reaction was partitioned between ethyl acetate and saturated aqueous sodium bicarbonate. The organic layer was washed with brine, dried over Na$_2$SO$_4$, filtered, and concentrated to provide the title compound. MS (DCI(+)) m/e 241.1 (M+H)$^+$

Example 64B 2-((3-amino-4-methoxybenzyl)(methyl)amino)ethanol

To a 25 mL round bottom flask was charged EXAMPLE 64A (380 mg, 1.58 mmol) and ethanol (8 mL). The suspension was treated with iron (0.707 g, 12.65 mmol) followed by a solution of ammonium chloride (169 mg, 3.16 mmol) in water (1.3 mL). The mixture was heated at 90° C. with vigorous stirring for 2 hours. The reaction was cooled to ambient temperature and filtered. The filter pad was washed with methanol and then CH$_2$Cl$_2$. The combined filtrates were washed with saturated aqueous sodium bicarbonate (30 mL). The aqueous layer was back-extracted with 2×60 mL 10% methanol/CH$_2$Cl$_2$. The combined organic layers were dried over Na$_2$SO$_4$, filtered, and concentrated to provide the title compound. MS (DCI(+)) m/e 211.1 (M+H)$^+$.

Example 64C 2-((3-(4-(2-chloroimidazo[1,2-a]pyridin-3-yl)pyrimidin-2-ylamino)-4-methoxybenzyl)(methyl)amino)ethanol A 5 mL reaction vial equipped with a stir bar was charged with EXAMPLE 12G (0.13 g, 0.49 mmol), EXAMPLE 64B (0.113 g, 0.539 mmol), 4 M HCl in 1,4-dioxane (0.150 mL, 0.6 mmol) and 2-propanol (2.6 ml). The vessel was sealed and the reaction was heated on a thermal block at 120° C. for 20 hours. The reaction was cooled to ambient temperature, diluted with 90 mL 10% methanol/$CH_2Cl_2$, washed with saturated aqueous sodium bicarbonate and brine, dried over $Na_2SO_4$, filtered, and concentrated. The concentrate was purified by flash chromatography on a 2 g silica gel column eluting with a gradient of from 0% to 4% methanol/$CH_2Cl_2$ to provide the title compound. (ESI(+)) m/e 439.0 $(M+H)^+$.

Example 64D

2-[{3-[(4-{2-[4-(benzyloxy)-3-methoxyphenyl]imidazo[1,2-a]pyridin-3-yl}pyrimidin-2-yl)amino]-4-methoxybenzyl}(methyl)amino]ethanol The trifluoroacetic acid salt of the title compound was prepared as described in EXAMPLE 12K, substituting EXAMPLE 64C for EXAMPLE 12J. MS (APCI(+)) m/e 617.5 $(M+H)^+$, $^1$H NMR (300 MHz, methanol-$d_4$) δ ppm 2.83 (s, 3 H) 3.05-3.18 (m, 2 H) 3.83 (m, 5 H) 4.00 (s, 3 H) 4.20-4.41 (m, 2 H) 5.20 (s, 2 H) 6.78 (d, 1 H) 7.17-7.27 (m, 5 H) 7.33-7.50 (m, 6 H) 7.91 (m, 2 H) 8.35 (m, 1 H) 8.40 (d, 1 H) 9.71 (d, 1 H).

Example 65

$N^1$-{4-[(4-{2-[4-(benzyloxy)-3-methoxyphenyl]imidazo[1,2-a]pyridin-3-yl}pyrimidin-2-yl)amino]phenyl}-$N^2,N^2$-dimethylglycinamide

Example 65A tert-butyl 4-(2-(dimethylamino)acetamido)phenylcarbamate

A 100 mL round bottom flask with stirbar was charged with tert-butyl 4-aminophenylcarbamate (2.38 g, 11.43 mmol), 2-(dimethylamino)acetic acid (1.25 g, 12.12 mmol), 1-ethyl-3-[3-(dimethylamino)propyl]-carbodiimide hydrochloride (2.59 g, 13.51 mmol) and 4-dimethylaminopyridine (0.05 g, 0.409 mmol) in dichloromethane (50 ml). The solution was stirred at ambient temperature for 2 hours. The mixture was shaken in a separatory funnel with 50 mL aqueous sodium bicarbonate, and the organics were separated and dried over magnesium sulfate and filtered. Solvent removal gave the title compound. MS (ESI(+)) m/e 294.0 $(M+H)^+$.

Example 65B

N-(4-aminophenyl)-2-(dimethylamino)acetamide

A 250 mL round bottom flask with stir bar containing EXAMPLE 65A (2.80 g, 9.54 mmol) dissolved in dichloromethane (80 ml) was cooled in an ice bath. Trifluoroacetic acid (20 ml, 260 mmol) was added. After 5 minutes, the ice bath was removed and the solution allowed to warm to ambient temperature. After 1 hour, the mixture was concentrated by rotovap to minimize excess TFA, then shaken in a separatory funnel with 200 mL each dichloromethane and aqueous sodium bicarbonate. The organic layer was dried over sodium sulfate and filtered. Solvent removal gave the title compound. MS (DCI(+)) m/e 194.1 $(M+H)^+$.

Example 65C

N-(4-(4-(2-chloroimidazo[1,2-a]pyridin-3-yl)pyrimidin-2-ylamino)phenyl)-2-(dimethylamino)acetamide The title compound was prepared as described in EXAMPLE 12J, substituting EXAMPLE 65B for EXAMPLE 12I. MS (ESI(+)) m/e 422.0 $(M+H)^+$.

Example 65D $N^1$-{4-[(4-{2-[4-(benzyloxy)-3-methoxyphenyl]imidazo[1,2-a]pyridin-3-yl}pyrimidin-2-yl)amino]phenyl}-$N^2,N^2$-dimethylglycinamide The title compound was prepared as described in EXAMPLE 12K, substituting EXAMPLE 65C for EXAMPLE 12J. MS (ESI(+)) m/e 600.3 $(M+H)^+$; $^1$H NMR (300 MHz, dimethylsulfoxide-$d_6$) δ ppm 9.63 (d, 2H), 9.56 (d, 1H), 8.34 (d, 1H), 7.73 (d, 1H), 7.67 (d, 2H), 7.57 (d, 2H), 7.50-7.35 (m, 4H), 7.26 (m, 1H), 7.19-7.12 (m, 2H), 7.05 (m, 1H), 6.66 (d, 1H), 5.15 (s, 2H), 3.75 (s, 3H), 3.05 (s, 2H), 2.28 (s, 6H).

Example 66

$N^1$-{3-[(4-{2-[4-(benzyloxy)-3-methoxyphenyl]imidazo[1,2-a]pyridin-3-yl}pyrimidin-2-yl)amino]phenyl}-$N^2,N^2$-dimethylglycinamide

Example 66A tert-butyl 3-(2-(dimethylamino)acetamido)phenylcarbamate

The title compound was prepared as described in EXAMPLE 65A, substituting tert-butyl 3-aminophenylcarbamate for tert-butyl 4-aminophenylcarbamate. MS (ESI(+)) m/e 294.0 $(M+H)^+$.

Example 66B

N-(3-aminophenyl)-2-(dimethylamino)acetamide

The title compound was prepared as described in EXAMPLE 65B, substituting EXAMPLE 66A for EXAMPLE 65A. MS (DCI(+)) m/e 194.1 $(M+H)^+$.

Example 66C

N-(3-(4-(2-chloroimidazo[1,2-a]pyridin-3-yl)pyrimidin-2-ylamino)phenyl)-2-(dimethylamino)acetamide The title compound was prepared as described in EXAMPLE 12J, substituting EXAMPLE 66B for EXAMPLE 12I. MS (ESI(+)) m/e 422.0 $(M+H)^+$.

Example 66D

N$^1$-{3-[(4-{2-[4-(benzyloxy)-3-methoxyphenyl]imidazo[1,2-a]pyridin-3-yl}pyrimidin-2-yl)amino]phenyl}-N$^2$,N$^2$-dimethylglycinamide The title compound was prepared as described in EXAMPLE 12K, substituting EXAMPLE 66C for EXAMPLE 12J. MS (ESI(+)) m/e 600.3 (M+H)$^+$; $^1$H NMR (300 MHz, dimethylsulfoxide-d$_6$) δ ppm 9.74 (s, 1H), 9.66 (d, 1H), 9.60 (s, 1H), 8.34 (d, 1H), 8.06 (s, 1H), 7.73 (d, 1H), 7.51-7.35 (m, 7H), 7.26 (m, 2H), 7.15 (m, 1H), 7.04 (m, 1H), 6.67 (d, 1H), 5.14 (s, 2H), 3.75 (s, 3H), 3.05 (s, 2H), 2.27 (s, 6H).

Example 67

N$^1$-{3-[(4-{2-[4-(benzyloxy)phenyl]imidazo[1,2-a]pyridin-3-yl}pyrimidin-2-yl)amino]phenyl}-N$^2$,N$^2$-dimethylglycinamide The title compound was prepared as described in EXAMPLE 12K, substituting EXAMPLE 66C for EXAMPLE 12J and 4-(benzyloxy)-phenylboronic acid for 4-(benzyloxy)-3-methoxyphenylboronic acid. MS (ESI(+)) m/e 570.2 (M+H)$^+$; $^1$H NMR (300 MHz, dimethylsulfoxide-d$_6$) δ ppm 9.73 (s, 1H), 9.65 (d, 1H), 9.60 (s, 1H), 8.32 (d, 1H), 8.05 (s, 1H), 7.72 (d, 1H), 7.58 (d, 2H), 7.51-7.39 (m, 5H), 7.30-7.19 (m, 2H), 7.12 (m, 1H), 7.04 (m, 1H), 6.62 (d, 1H), 5.17 (s, 2H), 3.05 (s, 2H), 2.27 (s, 6H).

Example 68

4-{2-[4-(benzyloxy)-3-methylphenyl]imidazo[1,2-a]pyridin-3-yl}-N-{3-[2-(dimethylamino)ethyl]phenyl}pyrimidin-2-amine

Example 68A 1-(benzyloxy)-4-bromo-2-methylbenzene

The title compound was prepared as described in EXAMPLE 49B, substituting 4-bromo-2-methylphenol for EXAMPLE 49A. MS DCI(+) m/e 278.0 (M+H)$^+$.

Example 68B 2-(4-(benzyloxy)-3-methylphenyl)-4,4,5,5-tetramethyl-1,3,2-dioxaborolane The title compound was prepared as described in EXAMPLE 49C, substituting EXAMPLE 68A for EXAMPLE 49B. MS (DCI(+)) m/e 342 (M+NH$_4$)$^+$; $^1$H NMR (300 MHz, dimethylsulfoxide-d$_6$) δ ppm 7.58-7.25 (m, 7 H), 7.02 (d, 1 H), 5.16 (s, 2 H), 2.19 (s, 3 H), 1.39-1.20 (m, 12 H).

Example 68C

4-{2-[4-(benzyloxy)-3-methylphenyl]imidazo[1,2-a]pyridin-3-yl}-N-{3-[2-(dimethylamino)ethyl]phenyl}pyrimidin-2-amine The title compound was prepared as described in EXAMPLE 12K, substituting EXAMPLE 68B for 4-(benzyloxy)-3-methoxyphenylboronic acid. MS (ESI(+)) m/e 555.3 (M+H)$^+$; $^1$H NMR (500 MHz, dimethylsulfoxide-d$_6$) δ ppm 9.67 (s, 1 H), 9.59 (d, 1 H), 8.33 (d, 1 H), 7.72 (d, 1 H), 7.64 (s, 1 H), 7.58 (d, 2 H), 7.53-7.31 (m, 7H), 7.23-7.17 (m, 1 H), 7.11 (d, 1 H), 7.05 (t, 1 H), 6.86 (t, 1 H), 6.64 (d, 1 H), 5.18 (s, 2 H), 2.69-2.62 (m, 2 H), 2.48-2.40 (m, 2 H), 2.24 (s, 3 H), 2.16 (s, 6 H).

Example 69

4-{2-[4-(benzyloxy)-3-methoxyphenyl]imidazo[1,2-a]pyridin-3-yl}-N-{4-[2-(dimethylamino)ethyl]phenyl}pyrimidin-2-amine

Example 69A

N,N-dimethyl-2-(4-nitrophenyl)ethanamine

A pressure tube was charged with 1-(2-bromoethyl)-4-nitrobenzene (1 g, 4.35 mmol) in acetonitrile (5 mL). Triethylamine (2.4 mL) and dimethylamine, 2M in tetrahydrofuran (0.784 g, 17.39 mmol) were added, and the sealed tube was stirred at ambient temperature for 2 days. The reaction mixture was partitioned between dilute NaHCO$_3$ solution and ethyl acetate, then extracted another two times with ethyl acetate. The product was then extracted into 2N HCl (2×25 mL). Following neutralization with 2N NaOH, the aqueous mixture was extracted with ethyl acetate (3×). The extracts were dried (Na$_2$SO$_4$), filtered and concentrated to give the title compound. MS (ESI(+)) m/e 194.9 (M+H)$^+$.

Example 69B 4-(2-(dimethylamino)ethyl)aniline

The title compound was prepared as described in EXAMPLE 71B, substituting EXAMPLE 69A for EXAMPLE 71A. MS (ESI(+)) m/e 165.1 (M+H)$^+$.

Example 69C 4-(2-chloroimidazo[1,2-a]pyridin-3-yl)-N-(4-(2-(dimethylamino)ethyl)phenyl)pyrimidin-2-amine The title compound was prepared as described in EXAMPLE 12J, substituting EXAMPLE 69B for EXAMPLE 12I. MS (ESI(+)) m/e 393.0 (M+H)$^+$.

Example 69D

4-{2-[4-(benzyloxy)-3-methoxyphenyl]imidazo[1,2-a]pyridin-3-yl}-N-{4-[2-(dimethylamino)ethyl]phenyl}pyrimidin-2-amine The title compound was prepared as described in EXAMPLE 12K, substituting EXAMPLE 69C for EXAMPLE 12J. MS (ESI(+)) m/e 571.3 (M+H)$^+$; $^1$H NMR (300 MHz, dimethylsulfoxide-d$_6$) δ ppm 9.63 (s, 1 H) 9.56 (d, 1 H) 8.34 (d, 1 H) 7.73 (d, 1 H) 7.62 (d, 2 H) 7.30-7.52 (m, 6 H) 7.26 (d, 1 H) 7.10-7.18 (m, 4 H) 7.05 (t, 1 H) 6.66 (d, 1 H) 5.13 (s, 2 H) 3.75 (s, 3 H) 2.61-2.70 (m, 2 H) 2.38-2.47 (m, 2 H) 2.14-2.21 (m, 6 H).

Example 70

1-{3-[(4-{2-[4-(benzyloxy)-3-methoxyphenyl]imidazo[1,2-a]pyridin-3-yl}pyrimidin-2-yl)amino]benzyl}pyrrolidin-3-ol

Example 70A 1-(3-nitrobenzyl)pyrrolidin-3-ol

A 25 mL round bottom was charged with 1-(bromomethyl)-3-nitrobenzene (542 mg, 2.509 mmol) pyrrolidin-3-ol (0.813 mL, 10.04 mmol), and triethylamine (1.399 mL, 10.04 mmol) in acetonitrile (5 mL). The resulting solution was stirred overnight at ambient temperature then poured into water (150 mL) and extracted with $CH_2Cl_2$ (4×30 mL). The extracts were washed with sat. $NaHCO_3$ solution, $H_2O$ and brine. The organic layer was then dried ($Na_2SO_4$) and concentrated in vacuo, yielding the title compound. MS (ESI(+)) m/e 222.9 $(M+H)^+$.

Example 70B 1-(3-aminobenzyl)pyrrolidin-3-ol

The title compound was prepared as described in EXAMPLE 71B, substituting EXAMPLE 70A for EXAMPLE 71A. MS (ESI(+)) m/e 192.9 $(M+H)^+$.

Example 70C 1-(3-(4-(2-chloroimidazo[1,2-a]pyridin-3-yl)pyrimidin-2-ylamino)benzyl)pyrrolidin-3-ol The title compound was prepared as described in EXAMPLE 12J, substituting EXAMPLE 70B for EXAMPLE 12I. MS (ESI(+)) m/e 421.0 $(M+H)^+$.

Example 70D

1-{3-[(4-{2-[4-(benzyloxy)-3-methoxyphenyl]imidazo[1,2-a]pyridin-3-yl}pyrimidin-2-yl)amino]benzyl}pyrrolidin-3-ol The title compound was prepared as described in EXAMPLE 12K, substituting EXAMPLE 70C for EXAMPLE 12J. MS (ESI(+)) m/e 599.3 $(M+H)^+$; $^1H$ NMR (300 MHz, dimethylsulfoxide-$d_6$) δ ppm 9.70 (s, 1 H) 9.60 (d, 1 H) 8.36 (d, 1 H) 7.72 (t, 1 H) 7.67 (s, 2 H) 7.31-7.52 (m, 6 H) 7.11-7.28 (m, 4 H) 7.06 (td, 1 H) 6.92 (m, 1 H) 6.68 (d, 1 H) 5.14 (s, 2 H) 4.64 (d, 1 H) 4.12-4.24 (m, 1 H) 3.75 (s, 3 H) 3.51 (d, 2 H) 2.70-2.65 (m, 2 H) 2.36-2.45 (m, 1 H) 2.25-2.32 (m, 1 H) 1.89-2.03 (m, 1 H) 1.45-1.57 (m, 1 H).

Example 71

$N^1$-{3-[(4-{2-[4-(benzyloxy)-3-methoxyphenyl]imidazo[1,2-a]pyridin-3-yl}pyrimidin-2-yl)amino]-4-methoxyphenyl}-$N^2$,$N^2$-dimethylglycinamide

Example 71A 2-(dimethylamino)-N-(4-methoxy-3-nitrophenyl)acetamide

The title compound was prepared as described in EXAMPLE 65A, substituting 4-methoxy-3-nitroaniline for tert-butyl 4-aminophenylcarbamate. MS (DCI(+)) m/e 254.1 $(M+H)^+$.

Example 71B

N-(3-amino-4-methoxyphenyl)-2-(dimethylamino)acetamide

EXAMPLE 71A (7.23 g, 28.5 mmol) and 5% Pd on charcoal (1.446 g, 13.59 mmol) in methanol (200 mL) were stirred at ambient temperature for 2 hours under 30 psi of hydrogen gas, then filtered, concentrated and vacuum dried to give the title compound. MS (DCI(+)) m/e 224.1 $(M+H)^+$.

Example 71C

N-(3-(4-(2-chloroimidazo[1,2-a]pyridin-3-yl)pyrimidin-2-ylamino)-4-methoxyphenyl)-2-(dimethylamino)acetamide The title compound was prepared as described in EXAMPLE 12J, substituting EXAMPLE 71B for EXAMPLE 12I. MS (ESI(+)) m/e 452.1 $(M+H)^+$.

Example 71D $N^1$-{3-[(4-{2-[4-(benzyloxy)-3-methoxyphenyl]imidazo[1,2-a]pyridin-3-yl}pyrimidin-2-yl)amino]-4-methoxyphenyl}-$N^2$,$N^2$-dimethylglycinamide The title compound was prepared as described in EXAMPLE 12K, substituting EXAMPLE 71C for EXAMPLE 12J. MS (ESI(+)) m/e 630.3 $(M+H)^+$; $^1H$ NMR (300 MHz, dimethylsulfoxide-$d_6$) δ ppm 9.53 (s, 1H), 9.47 (d, 1H), 8.55 (s, 1H), 8.29 (d, 1H), 8.11 (m, 1H), 7.70 (d, 1H), 7.50-7.33 (m, 6H), 7.23 (s, 1H), 7.14 (m, 1H), 7.03 (m, 1H), 6.95 (m, 1H), 6.62 (d, 1H), 5.14 (s, 2H), 3.83 (s, 3H), 3.75 (s, 3H), 3.01 (s, 2H), 2.24 (s, 6H).

Example 72

$N^1$-{3-[(4-{2-[4-(benzyloxy)phenyl]imidazo[1,2-a]pyridin-3-yl}pyrimidin-2-yl)amino]-4-methoxyphenyl}-$N^2$,$N^2$-dimethylglycinamide The title compound was prepared as described in EXAMPLE 12K, substituting EXAMPLE 71C for EXAMPLE 12J and 4-(benzyloxy)-phenylboronic acid for 4-(benzyloxy)-3-methoxyphenylboronic acid. MS (ESI(+)) m/e 600.2 $(M+H)^+$; $^1H$ NMR (300 MHz, dimethylsulfoxide-$d_6$) δ ppm 9.54 (s, 1H), 9.46 (d, 1H), 8.56 (s, 1H), 8.27 (d, 1H), 8.10 (m, 1H), 7.69 (d, 1H), 7.56 (d, 2H), 7.51-7.37 (m, 5H), 7.12 (d, 2H), 7.05 (d, 1H), 6.96 (m, 1H), 6.56 (d, 1H), 5.17 (s, 2H), 3.83 (s, 3H), 3.01 (s, 2H), 2.24 (s, 6H).

Example 73

4-{2-[4-(benzyloxy)-3-methoxyphenyl]imidazo[1,2-a]pyridin-3-yl}-N-(2-methoxy-5-thiomorpholin-4-ylphenyl)pyrimidin-2-amine

Example 73A 4-(4-methoxy-3-nitrophenyl)thiomorpholine

The title compound was prepared as described in EXAMPLE 52A, substituting thiomorpholine for morpholine. MS (DCI(+)) m/e 255.1 $(M+H)^+$.

Example 73B 2-methoxy-5-thiomorpholinoaniline

The title compound was prepared as described in EXAMPLE 51B, substituting EXAMPLE 73A for EXAMPLE 51A. MS (DCI(+)) m/e 225.1 $(M+H)^+$.

Example 73C 4-(2-chloroimidazo[1,2-a]pyridin-3-yl)-N-(2-methoxy-5-thiomorpholinophenyl)pyrimidin-2-amine The title compound was prepared as described in EXAMPLE 51C, substituting EXAMPLE 73B for EXAMPLE 51B. MS (ESI(+)) m/e 453.0 (M+H)$^+$; (ESI(−)) m/e 451.1 (M−H)$^−$.

Example 73D

4-{2-[4-(benzyloxy)-3-methoxyphenyl]imidazo[1,2-a]pyridin-3-yl}-N-(2-methoxy-5-thiomorpholin-4-ylphenyl)pyrimidin-2-amine The trifluoroacetic acid salt of the title compound was prepared as a trifluoroacetic acid salt, as described in EXAMPLE 12K, substituting EXAMPLE 73C for EXAMPLE 12J. MS (ESI(+)) m/e 631 (M+H)$^+$; (ESI(−)) m/e 629 (M−H)$^−$; $^1$H NMR (300 MHz, dimethylsulfoxide-d$_6$) δ 9.51 (d, 1 H), 8.70 (s, 1 H), 8.38 (d, 1 H), 7.83 (d, 1 H), 7.64-7.73 (m, 2 H), 7.35-7.52 (m, 5 H), 7.27 (s, 1 H), 7.15-7.22 (m, 3 H), 7.05 (d, 1 H), 6.81 (d, 1 H), 6.69 (d, 1 H), 5.16 (s, 2 H), 3.82 (s, 3 H), 3.75 (s, 3 H), 3.30-3.40 (m, 4 H), 2.64-2.71 (m, 4 H).

Example 74

4-{2-[4-(benzyloxy)-3-methoxyphenyl]imidazo[1,2-a]pyridin-3-yl}-N-[5-(1,1-dioxidothiomorpholin-4-yl)-2-methoxyphenyl]pyrimidin-2-amine The title compound was prepared as described in EXAMPLE 63, substituting EXAMPLE 73D for EXAMPLE 51D. MS (APCI(+)) m/e 663 (M+H)$^+$; $^1$H NMR (500 MHz, chloroform-d) δ 9.43 (d, 1H), 8.33 (s, 1 H), 8.29 (d, 1 H), 7.92 (s, 1 H), 7.82 (s, 1 H), 7.46 (d, 2 H), 7.40-7.45 (m, 1 H), 7.38 (t, 2 H), 7.29-7.34 (m, 2 H), 7.17 (dd, 1 H), 6.91-6.98 (m, 2 H), 6.87 (d, 1 H), 6.75 (t, 1 H), 6.57 (dd, 1 H), 5.21 (s, 2 H), 3.93 (s, 3H), 3.89 (s, 3 H), 3.63-3.69 (m, 4 H), 3.01-3.08 (m, 4 H).

Example 75

Steven Fidanze

4-{2-[4-(benzyloxy)phenyl]pyrazolo[1,5-a]pyridin-3-yl}-N-{3-[2-(dimethylamino)ethyl]phenyl}pyrimidin-2-amine

Example 75A 4-((4-(benzyloxy)phenyl)ethynyl)-2-chloropyrimidine

Into a 250 mL round-bottomed flask was charged 1-(benzyloxy)-4-ethynylbenzene (2.0540 g, 9.86 mmol) and tetrahydrofuran (49.3 ml). 2,4-Dichloropyrimidine (1.469 g, 9.86 mmol), bis(triphenylphosphine)palladium(II) dichloride (0.346 g, 0.493 mmol), copper(I) iodide (0.033 ml, 0.986 mmol), and triethylamine (4.12 ml, 29.6 mmol) were added. The reaction was heated to 45° C. overnight. Silica gel (approx. 15 g) was added, and the reaction concentrated. The reaction was purified by flash chromatography (10% ethyl acetate:hexanes for 10 minutes, then to 30% ethyl acetate:hexanes over 30 minutes, then to 50% ethyl acetate in hexanes over 5 minutes, then to 100% ethyl acetate over 5 minutes.) to provide the title compound. MS (ESI) m/e 321 (M+H)$^+$.

Example 75B 2-(4-(benzyloxy)phenyl)-3-(2-chloropyrimidin-4-yl)pyrazolo[1,5-a]pyridine Into a 4 mL vial was charged EXAMPLE 75A (0.1104 g, 0.344 mmol) and 1-aminopyridinium iodide (0.076 g, 0.344 mmol) in dimethylsulfoxide (1.721 ml). The reaction was frozen in an ice bath. Potassium carbonate (0.190 g, 1.377 mmol) and potassium hydroxide (0.039 g, 0.688 mmol) were added. The reaction was allowed to warm to room temperature and stirred for 1.5 h. Water was added, and the resulting suspension was filtered, and the solids rinsed with water to provide a light green solid. MS (ESI) m/e 413 (M+H)$^+$.

Example 75C

4-{2-[4-(benzyloxy)phenyl]pyrazolo[1,5-a]pyridin-3-yl}-N-{3-[2-(dimethylamino)ethyl]phenyl}pyrimidin-2-amine The title compound was prepared as described in EXAMPLE 12J, substituting EXAMPLE 75B for EXAMPLE 12G. MS (ESI) m/e 377 (M+H)$^+$. MS (ESI) m/e 541 (M+H)$^+$; $^1$H NMR (300 MHz, dimethylsulfoxide-d$_6$) δ 9.47 (m, 1H), 8.81 (d, 1H), 8.49 (d, 1H), 8.25 (d, 1H), 7.64 (m, 1H), 7.55 (m, 3H), 7.35-7.51 (m, 7H), 7.16 (m, 3H), 7.10 (m, 1H), 6.82 (d, 1H), 6.49 (d, 1H), 5.17 (s, 2H), 2.65 (m, 2H), 2.43 (m, 2H), 2.15 (s, 6H).

Example 76

4-{2-[4-(benzyloxy)phenyl]pyrazolo[1,5-b]pyridazin-3-yl}-N-{3-phenyl}pyrimidin-2-amine

Example 76A 1-aminopyridazin-1-ium iodide

Into a 125 mL Erlenmeyer flask was charged hydroxylamine-O-sulfonic acid (14.12 g, 125 mmol) in water (30 mL) to give a colorless solution. Into a separate 125 mL Erlenmeyer flask was charged potassium bicarbonate (5.76 ml, 125 mmol) in water (100 mL) to give a colorless solution. Both solutions were cooled to 0° C., and the bicarbonate solution added to the sulfonic acid over 10 minutes. The mixture was stirred for 10 minutes. Into a 500 mL round-bottomed flask was charged pyridazine (9.05 ml, 125 mmol) in water (70 mL). The hydroxylamine sulfonate solution was added to the pyridizine solution, and the mixture heated to 70° C. for 4.5 hours. The reaction was cooled to room temperature. Potassium iodide (20.73 g, 125 mmol) was added. The reaction was concentrated on a rotovap. The residue was triturated with ethanol (300 mL). The solids were collected and recrystallized from 35 mL ethanol to provide the title compound. MS (DCI) m/e 96 (M$^+$).

Example 76B 2-(4-(benzyloxy)phenyl)-3-(2-chloropyrimidin-4-yl)pyrazolo[1,5-b]pyridazine The title compound was prepared as described in EXAMPLE 75B, substituting EXAMPLE 76A for aminopyridinium iodide. MS (ESI) m/e 414 (M+H)$^+$.

Example 76C

4-{2-[4-(benzyloxy)phenyl]pyrazolo[1,5-b]pyridazin-3-yl}-N-{3-[2-(dimethylamino)ethyl]phenyl}pyrimidin-2-amine The title compound was prepared as described in EXAMPLE 12J, substituting EXAMPLE 76B for EXAMPLE 12G. MS (ESI) m/e 542 (M+H)$^+$; $^1$H NMR (300 MHz, dimethylsulfoxide-d$_6$) δ 9.55 (s, 1H), 8.90 (d, 1H), 8.60 (dd, 1H), 8.32 (d, 1H), 7.60 (m, 3H), 7.55 (m, 1H), 7.50 (m, 2H), 7.40 (m, 4H), 7.16 (m, 3H), 6.82 (d, 1H), 6.57 (d, 1H), 5.18 (s, 2H), 2.65 (m, 2H), 2.43 (m, 2H), 2.15 (s, 6H).

Example 77

4-{2-[4-(benzyloxy)phenyl]-6-fluoropyrazolo[1,5-a]pyridin-3-yl}-N-{3-[2-(dimethylamino)ethyl]phenyl}pyrimidin-2-amine

Example 77A

O-(mesitylsulfonyl)hydroxylamine

Into a 250 mL round-bottomed flask was added ethyl o-mesitylsulfonylacetohydroxamate (10.00 g, 35.0 mmol) in dioxane (10.01 ml). The solution was cooled to 0° C. Perchloric acid (5.23 ml, 47.6 mmol) was added dropwise via an addition funnel over 5 minutes. The reaction was stirred at 0° C. an additional 10 minutes. The resulting suspension was poured onto ice/water (100 mL). The suspension was filtered and rinsed with water. The solid was taken up into a minimal amount of ether, then precipitated out with hexanes. The suspension was filtered, and the solid was rinsed with hexanes and collected.

Example 77B 1-amino-3-fluoropyridinium 2,4,6-trimethylbenzenesulfonate

Into a 250 mL round-bottomed flask was charged 3-fluoropyridine (0.442 ml, 5.15 mmol) and CH$_2$Cl$_2$ (1.25 mL). The solution was cooled to 0° C. EXAMPLE 77A (1.109 g, 5.15 mmol) was added dropwise as a solution in 1.25 mL CH$_2$Cl$_2$. The ice-water bath was immediately removed, and the reaction stirred 2 hours at room temperature. Ether (50 mL) was added, the resulting suspension filtered and the solids were rinsed with ether. MS (DCI) m/e 113 (M$^+$).

Example 77C 2-(4-(benzyloxy)phenyl)-3-(2-chloropyrimidin-4-yl)-6-fluoropyrazolo[1,5-a]pyridine The title compound was prepared as described in EXAMPLE 75B, substituting EXAMPLE 77B for aminopyridinium iodide. MS (ESI) m/e 431 (M+H)$^+$.

Example 77D

4-{2-[4-(benzyloxy)phenyl]-6-fluoropyrazolo[1,5-a]pyridin-3-yl}-N-{3-[2-(dimethylamino)ethyl]phenyl}pyrimidin-2-amine The title compound was prepared as described in EXAMPLE 12J, substituting EXAMPLE 77C for EXAMPLE 12G. MS (ESI) m/e 559 (M+H)$^+$; $^1$H NMR (300 MHz, dimethylsulfoxide-d$_6$) δ 9.50 (s, 1H), 8.71 (d, 1H), 8.47 (d, 1H), 7.50 (m, 3H), 7.41 (m, 3H), 7.35 (m, 3H), 7.26 (m, 1H), 7.02 (m, 4H), 6.86 (dd, 1H), 6.73 (d, 1H), 5.10 (s, 2H), 2.56 (m, 2H), 2.35 (m, 2H), 2.11 (s, 6H).

Example 78

4-{6-[4-(benzyloxy)phenyl]imidazo[2,1-b][1,3]thiazol-5-yl}-N-phenylpyrimidin-2-amine

Example 78A 1-(6-chloroimidazo[2,1-b]thiazol-5-yl)ethanone

To a solution of 6-chloroimidazo[2,1-b]thiazole (7.93 g, 50 mmol) in acetic anhydride (150 mL) was added 0.2 ml of concentrated sulfuric acid. The mixture was stirred at 140° C. for 4 hours. The mixture was evaporated to dryness and the residue was taken up in water (300 mL), and the pH adjusted to pH ~10 with aqueous NaOH. The resulting precipitate was filtered, washed with water and vacuum dried, providing the title compound. MS: (ESI(+)) m/e 200.8 (M+H)$^+$.

Example 78B (E)-1-(6-chloroimidazo[2,1-b]thiazol-5-yl)-3-(dimethylamino)prop-2-en-1-one In a round bottom flask was mixed EXAMPLE 78A (9.23 g, 46.0 mmol), 1-methyl-2-pyrrolidinone (80 mL) and 1,1-dimethoxy-N,N-dimethylmethanamine (18.39 ml, 138 mmol). The mixture was stirred at 60° C. overnight and concentrated under vacuum, providing the title compound. MS: (ESI(+)) m/e 255.8 (M+H)$^+$.

Example 78C 4-(6-chloroimidazo[2,1-b]thiazol-5-yl)-N-phenylpyrimidin-2-amine A round bottom flask was charged with EXAMPLE 78B (0.56 g, 2.19 mmol), 1-phenylguanidine carbonate (0.433 g, 3.2 mmol) and potassium carbonate (1.816 g, 13.14 mmol) in 1-methyl-2-pyrrolidinone (10 mL) and stirred at 100° C. for 5 days. The mixture was concentrated under vacuum and the residue was mixed with water (30 mL) and extracted with dichloromethane (5×30 mL). The solution was dried (MgSO$_4$), filtered, and concentrated. The residue was chromatographed on a silica gel column, eluting with 50% ethyl acetate in hexane to provide the title compound. MS: (ESI(+)) m/e 325.9 (M+H)$^+$.

Example 78D

4-{6-[4-(benzyloxy)phenyl]imidazo[2,1-b][1,3]thiazol-5-yl}-N-phenylpyrimidin-2-amine A vessel was charged with EXAMPLE 78C (150 mg, 0.458 mmol), 4-(benzyloxy)phenylboronic acid (157 mg, 0.686 mmol), sodium carbonate (146 mg, 1.373 mmol) and 1,2-dimethoxyethane (3.5 mL) and water (1.5 mL). The mixture was purged with argon and palladium-bis-(triphenylphosphine) dichloride (32.1 mg, 0.046 mmol) was added. The sealed vessel was heated at 160° C. for 90 minutes. Another portion of the catalyst was added and the mixture was stirred at 160° C. for 2 hours. The reaction mixture was mixed with water (10 ml) and extracted with dichloromethane. The crude product was absorbed on silica and purified on a silica gel column, eluting with 50% ethyl acetate in hexane to provide the title compound. MS: (ESI(+)) m/e 476.0 (M+H)$^+$; $^1$H NMR (500 MHz, DMSO-d$_6$) δ ppm 9.66 (s, 1H), 8.85 (s, 1H), 8.27 (d, 1H), 7.74 (d, 2H), 7.55 (d, 2H), 7.50-7.46 (m, 3H), 7.42 (t, 2H), 7.38-7.30 (m, 3H), 7.13 (d, 2H), 6.99 (t, 1H), 6.58 (d, 1H), 5.18 (s, 2H).

Example 79

4-{6-[4-(benzyloxy)phenyl]imidazo[2,1-b][1,3]thiazol-5-yl}-N-(2-methoxyphenyl)pyrimidin-2-amine Example 79A 4-(6-chloroimidazo[2,1-b]thiazol-5-yl)-N-(2-methoxyphenyl)pyrimidin-2-amine The title compound was prepared according to the procedure of EXAMPLE 78C, substituting 1-(2-methoxyphenyl)guanidine hydrochloride for 1-phenylguanidine carbonate. MS: (ESI(+)) m/e 357.9 (M+H)$^+$.

Example 79B

4-{6-[4-(benzyloxy)phenyl]imidazo[2,1-b][1,3]thiazol-5-yl}-N-(2-methoxyphenyl)pyrimidin-2-amine The title compound was prepared according to the procedure of EXAMPLE 78D, substituting EXAMPLE 79A for EXAMPLE 78C. MS: (ESI(+)) m/e 506.1 (M+H)$^+$; $^1$H NMR (500 MHz, DMSO-d$_6$) δ ppm 8.61 (s, 1H), 8.60 (bs, 1H), 8.20 (d, 1H), 7.83 (d, 1H), 7.53 (d, 2H), 7.50 (d, 2H), 7.42 (t, 2H), 7.38-7.33 (m, 2H), 7.14-7.09 (m, 4H), 6.97-6.94 (dt, 1H), 6.55 (d, 1H), 5.17 (s, 2H), 3.84 (s, 3H).

Example 80

4-{6-[4-(benzyloxy)phenyl]imidazo[2,1-b][1,3]thiazol-5-yl}-N-{4-[4-(dimethylamino)piperidin-1-yl]-2-methoxyphenyl}pyrimidin-2-amine Example 80A 1-(3-methoxy-4-nitrophenyl)-N,N-dimethylpiperidin-4-amine A solution of 4-fluoro-2-methoxy-1-nitrobenzene (1.711 g, 10 mmol), N,N-dimethylpiperidin-4-amine (1.410 g, 11.00 mmol) and N-ethyl-N-isopropylpropan-2-amine (3.48 ml, 20.00 mmol) in anhydrous N,N-dimethylformamide (25 mL) was stirred at 70° C. overnight. The mixture was concentrated and the residue was mixed with water (60 mL), adjusted to pH 12, then extracted with CH$_2$Cl$_2$. The crude product was purified on a silica gel column eluting with 7.5% methanol in CH$_2$Cl$_2$ saturated with NH$_3$ to give the title compound. (ESI(+)) m/e 280.1 (M+H)$^+$.

Example 80B 1-(4-amino-3-methoxyphenyl)-N,N-dimethylpiperidin-4-amine

EXAMPLE 80A (2.7 g, 9.67 mmol), iron powder (2.70 g, 48.3 mmol) and ammonium chloride (0.517 g, 9.67 mmol) were mixed with absolute ethanol (100 mL) and water (25 mL). The mixture was refluxed for 2 hours and filtered through a nylon membrane. The filtrate was concentrated to remove most of the ethanol. The aqueous solution was adjusted to pH 13-14 and extracted with CH$_2$Cl$_2$. The organic solution was dried (MgSO$_4$), filtered and concentrated to give the title compound. (ESI(+)) m/e 250.2 (M+H)$^+$.

Example 80C 4-(6-chloroimidazo[2,1-b]thiazol-5-yl)pyrimidin-2-amine

A round bottom flask was charged with EXAMPLE 78B (11.76 g, 46 mmol), guanidine hydrochloride (13.18 g, 138 mmol) and potassium carbonate (31.8 g, 230 mmol) in anhydrous 1-methyl-2-pyrrolidinone (150 mL) and the mixture was stirred at 95° C. for 22 hours. An additional 3.9 g of guanidine HCl and 8 g of potassium carbonate was added and the mixture was stirred at 95° C. for another 16 hours. The mixture was concentrated, and the residue was treated with water (300 mL), and the solid was collected and washed with water, then vacuum dried to provide the title compound. MS (ESI(+)) m/e 251.8 (M+H)$^+$.

Example 80D 4-(6-chloroimidazo[2,1-b]thiazol-5-yl)pyrimidin-2-ol

In a 250-mL round bottom flask was mixed EXAMPLE 80C (11.00 g, 43.7 mmol) and acetic acid (150 mL). The thick slurry was stirred at 60° C. for about 10 minutes. A solution of sodium nitrite (9.05 g, 131 mmol) in water (18 mL) was then added dropwise over 20 minutes. The mixture was stirred at 60° C. for 45 minutes, then allowed to cool to room temperature. The mixture was concentrated by rotary evaporation, and the residue was mixed with water (200 mL), cooled with an ice-bath, and adjusted to ~pH7.0 with concentrated aqueous NaOH solution. The resulting solid was collected by filtration, washed with water (3×50 mL), then dried in a vacuum oven to provide the title compound. MS (ESI(–)) m/e 250.8 (M–H)$^-$.

Example 80E 6-chloro-5-(2-chloropyrimidin-4-yl)imidazo[2,1-b]thiazole

A mixture of EXAMPLE 80D (9.97 g, 39.5 mmol) and phosphoryl trichloride (110 ml, 1184 mmol) was stirred at 80° C. for 5 hours. The mixture was cooled to room temperature, then concentrated to dryness. Water (150 mL) was added cautiously. The mixture was cooled with an ice bath and adjusted to pH~11 with concentrated aqueous NaOH, then stirred for 30 minutes. The solid was collected by filtration, washed with water (3×50 mL), and dried in a vacuum oven overnight at ~50° C. to provide the title compound. (ESI(+)) m/e 271.1 (M+H)$^+$.

Example 80F 4-(6-chloroimidazo[2,1-b]thiazol-5-yl)-N-(4-(4-(dimethylamino)piperidin-1-yl)-2-methoxyphenyl)pyrimidin-2-amine A mixture of EXAMPLE 80E (271 mg, 1.0 mmol), EXAMPLE 80B (262 mg, 1.05 mmol) and 4 M HCl in dioxane (0.250 ml, 1.000 mmol) in iso-propanol (10 mL) was stirred at 75° C. for 3 days. The reaction mixture was mixed with water (15 mL), adjusted to pH~13 with concentrated aqueous NaOH, then extracted with $CH_2Cl_2$. The crude product was purified on a silica gel column eluting with 5% methanol in $CH_2Cl_2$ saturated with $NH_3$. The resulting solid was triturated with water 3 times and vacuum dried to give the title compound. (ESI(+)) m/e 484.1 $(M+H)^+$.

Example 80G

4-{6-[4-(benzyloxy)phenyl]imidazo[2,1-b][1,3]thiazol-5-yl}-N-{4-[4-(dimethylamino)piperidin-1-yl]-2-methoxyphenyl}pyrimidin-2-amine The title compound was prepared according to the procedure of EXAMPLE 78D, substituting EXAMPLE 80F for EXAMPLE 78C. MS: (ESI(+)) m/e 632.2 $(M+H)^+$; $^1H$ NMR (500 MHz, DMSO-$d_6$) δ ppm 8.45 (s, 1H), 8.12 (d, 1H), 7.52-7.49 (m, 4H), 7.43-7.30 (m, 6H), 7.11 (d, 2H), 6.67 (s, 1H), 6.52 (d, 1H), 6.45 (d, 1H), 5.17 (s, 2H), 3.78 (s, 3H), 3.75-3.71 (m, 2H), 2.71-2.66 (m, 2H), 2.21 (s, 6H), 2.19-2.15 (m, 1H), 1.87-1.84 (d, 2H), 1.55-1.47 (m, 2H).

Example 81

$N^1$-(4-{6-[4-(benzyloxy)-3-methoxyphenyl]imidazo[2,1-b][1,3]thiazol-5-yl}pyrimidin-2-yl)-2-methoxy-$N^4,N^4$-dimethylbenzene-1,4-diamine Example 81A 3-methoxy-N,N-dimethyl-4-nitroaniline The title compound was prepared according to the procedure of EXAMPLE 80A, substituting dimethylamine for N,N-dimethylpiperidin-4-amine. MS: (ESI(+)) m/e 197.2 $(M+H)^+$.

Example 81B 3-methoxy-$N^1,N^1$-dimethylbenzene-1,4-diamine

The title compound was prepared according to the procedure of EXAMPLE 80B, substituting EXAMPLE 81A for EXAMPLE 80A. MS: (ESI(+)) m/e 167.1 $(M+H)^+$.

Example 81C $N^1$-(4-(6-chloroimidazo[2,1-b]thiazol-5-yl)pyrimidin-2-yl)-2-methoxy-$N^4,N^4$-dimethylbenzene-1,4-diamine The title compound was prepared according to the procedure of EXAMPLE 80F, substituting EXAMPLE 81B for EXAMPLE 80B. (ESI(+)) m/e 400.9 $(M+H)^+$.

Example 81D $N^1$-(4-{6-[4-(benzyloxy)-3-methoxyphenyl]imidazo[2,1-b][1,3]thiazol-5-yl}pyrimidin-2-yl)-2-methoxy-$N^4,N^4$-dimethylbenzene-1,4-diamine The title compound was prepared according to the procedure of EXAMPLE 78D, substituting EXAMPLE 81C for EXAMPLE 78C and 4-(benzyloxy)-3-methoxyphenylboronic acid for 4-benzyloxyphenylboronic acid. MS: (ESI(+)) m/e 579.2 $(M+H)^+$; $^1H$ NMR (500 MHz, DMSO-$d_6$) δ ppm 8.41 (s, 1H), 8.12 (d, 1H), 7.48 (d, 2H), 7.43-7.40 (m, 3H), 7.36 (d, 1H), 7.32-7.20 (m, 2H), 7.18 (s, 1H), 7.15-7.10 (m, 2H), 6.49 (d, 1H), 6.45 (d, 1H), 6.33 (d, 1H), 5.14 (s, 2H), 3.78 (s, 3H), 3.76 (s, 3H), 2.93 (s, 6H).

Example 82

4-{6-[4-(benzyloxy)-3-methoxyphenyl]imidazo[2,1-b][1,3]thiazol-5-yl}-N-[2-(pyrrolidin-1-ylmethyl)phenyl]pyrimidin-2-amine Example 82A 4-(6-chloroimidazo[2,1-b]thiazol-5-yl)-N-(2-(pyrrolidin-1-ylmethyl)phenyl)pyrimidin-2-amine The title compound was prepared according to the procedure of EXAMPLE 80F, substituting 2-(pyrrolidin-1-y)methyl aniline for EXAMPLE 80B. (ESI(+)) m/e 411.0 $(M+H)^+$.

Example 82B

4-{6-[4-(benzyloxy)-3-methoxyphenyl]imidazo[2,1-b][1,3]thiazol-5-yl}-N-[2-(pyrrolidin-1-ylmethyl)phenyl]pyrimidin-2-amine The title compound was prepared according to the procedure of EXAMPLE 78D, substituting EXAMPLE 82A for EXAMPLE 78C and 4-(benzyloxy)-3-methoxyphenylboronic acid for 4-benzyloxyphenylboronic acid. MS: (ESI(+)) m/e 589.2 $(M+H)^+$; $^1H$ NMR (500 MHz, DMSO-$d_6$) δ ppm 10.51 (s, 1H), 8.51 (d, 1H), 8.29 (d, 1H), 8.20 (d, 1H), 7.49 (d, 2H), 7.45 (d, 1H), 7.42 (t, 2H), 7.37-7.35 (t, 1H), 7.29-7.25 (m, 2H), 7.21 (s, 1H), 7.15 (s, 2H), 6.98 (t, 1H), 6.66 (d, 1H), 5.15 (s, 2 H), 3.77 (s, 2H), 3.76 (s, 3H), 2.54 (bs, 4H), 1.80 (s, 4H).

Example 83

4-{6-[4-(benzyloxy)-3-methoxyphenyl]imidazo[2,1-b][1,3]thiazol-5-yl}-N-{4-[dimethylamino)methyl]phenyl}pyrimidin-2-amine Example 83A 4-(6-chloroimidazo[2,1-b]thiazol-5-yl)-N-(4-((dimethylamino)methyl)phenyl)pyrimidin-2-amine The title compound was prepared according to the procedure of EXAMPLE 80F, substituting 4-(dimethylamino)methyl aniline for EXAMPLE 80B. (ESI(+)) m/e 384.9 $(M+H)^+$.

Example 83B

4-{6-[4-(benzyloxy)-3-methoxyphenyl]imidazo[2,1-b][1,3]thiazol-5-yl}-N-{4-[dimethylamino)methyl]phenyl}pyrimidin-2-amine The title compound was prepared according to the procedure of EXAMPLE 78D, substituting EXAMPLE 83A for EXAMPLE 78C and 4-(benzyloxy)-3-methoxyphenylboronic acid for 4-benzyloxyphenylboronic acid. MS: (ESI(+)) m/e 563.2 $(M+H)^+$; $^1H$ NMR (500 MHz, DMSO-$d_6$) δ ppm 9.65 (s, 1H), 8.85 (bs, 1H), 8.27 (d, 1H), 7.68 (d, 2H), 7.50-

7.46 (m, 3H), 7.42 (t, 2H), 7.36 (t, 1H), 7.26-7.21 (m, 3H), 7.15 (m, 2H), 6.64 (d, 1H), 5.15 (s, 2 H), 3.76 (s, 3H), 3.37 (s, 2H), 2.17 (s, 6H).

Example 84

4-{6-[4-(benzyloxy)-3-methoxyphenyl]imidazo[2,1-b][1,3]thiazol-5-yl}-N-{4-[4-(dimethylamino)piperidin-1-yl]-2-methoxyphenyl}pyrimidin-2-amine The title compound was prepared according to the procedure of EXAMPLE 78D, substituting EXAMPLE 80F for EXAMPLE 78C and 4-(benzyloxy)-3-methoxyphenylboronic acid for 4-benzyloxyphenylboronic acid. (ESI(+)) m/e 662.3 (M+H)$^+$; $^1$H NMR (500 MHz, DMSO-d$_6$) δ ppm 8.44 (s, 1H), 8.14 (d, 1H), 7.49 (d, 2H), 7.42 (t, 2H), 7.35-7.30 (m, 4H), 7.18 (s, 1H), 7.15-7.10 (m, 2H), 6.66 (s, 1H), 6.52-6.50 (m, 2H), 5.14 (s, 2 H), 3.78 (s, 3H), 3.75 (s, 3H), 3.75-3.71 (m, 2H), 2.71-2.66 (m, 2H), 2.20 (s, 6H), 2.19-2.15 (m, 1H), 1.87-1.84 (d, 2H), 1.55-1.47 (m, 2H).

Example 85

4-{6-[4-(benzyloxy)-3-methoxyphenyl]imidazo[2,1-b][1,3]thiazol-5-yl}-N-{3-[2-(dimethylamino)ethyl]phenyl}pyrimidin-2-amine Example 85A N,N-dimethyl-2-(3-nitrophenyl)ethanamine A 250 mL round bottom flask was charged with 1-(2-bromoethyl)-3-nitrobenzene (10 g, 43.5 mmol) and acetonitrile (36 mL). The suspension was treated with triethylamine (18.1 mL, 130 mmol) and dimethylamine (2 M in tetrahydrofuran, 65.2 mL, 130 mmol). The resulting solution was stirred at ambient temperature for 48 hours. The reaction was concentrated. The residual solid was partitioned between ethyl acetate (130 mL) and 60 ml saturated aqueous sodium bicarbonate. The aqueous layer was washed with ethyl acetate (75 mL). The combined organic layers were washed with brine, dried over MgSO$_4$, filtered, and concentrated. The concentrate was purified by flash chromatography on an 80 g silica gel column using an AnaLogix IntelliFlash 280 system eluting with a gradient of from 0% to 7% methanol in CH$_2$Cl$_2$ to provide the title compound. MS (DCI(+)) m/e 195.1 (M+H)$^+$.

Example 85B 3-(2-(dimethylamino)ethyl)aniline

In a 250 mL stainless steel pressure bottle, EXAMPLE 85A (5.02 g, 25.8 mmol) in methanol (70 mL) was treated with 5% Pd—C (wet, 1.40 g, 25.8 mmol) and the suspension was shaken under 30 psi of hydrogen for 1.3 hours at ambient temperature. The mixture was filtered through a nylon membrane and concentrated to provide the title compound. MS (DCI(+)) m/e 165.1 (M+H)$^+$.

Example 85C 4-(6-chloroimidazo[2,1-b]thiazol-5-yl)-N-(3-(2-(dimethylamino)ethyl)phenyl)pyrimidin-2-amine The title compound was prepared according to the procedure of EXAMPLE 80F, substituting EXAMPLE 85B for EXAMPLE 80B. MS: (ESI(+)) m/e 398.9 (M+H)$^+$.

Example 85D

4-{6-[4-(benzyloxy)-3-methoxyphenyl]imidazo[2,1-b][1,3]thiazol-5-yl}-N-{3-[2-(dimethylamino)ethyl]phenyl}pyrimidin-2-amine The trifluoroacetic acid salt of the title compound was prepared according to the procedure of EXAMPLE 78D, substituting EXAMPLE 85C for EXAMPLE 78C and 4-(benzyloxy)-3-methoxyphenylboronic acid for 4-benzyloxyphenylboronic acid. (ESI(+)) m/e 577.2 (M+H)$^+$; $^1$H NMR (500 MHz, DMSO-d$_6$) δ ppm 9.73 (s, 1H), 9.53 (bs, 1H), 8.86 (bs, 1H), 8.30 (d, 1H), 7.72 (s, 1H), 7.59 (d, 1H), 7.51-7.48 (m, 2H), 7.43 (t, 2H), 7.36 (t, 1H), 7.30 (t, 1H), 7.21 (s, 1H), 7.15-7.10 (m, 2H), 6.93 (d, 1H), 6.67 (d, 1H), 5.15 (s, 2 H), 3.76 (s, 3H), 3.33-3.29 (m, 2H), 2.97-2.94 (m, 2H), 2.85 (s, 6H).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:

1. A compound of formula (I)

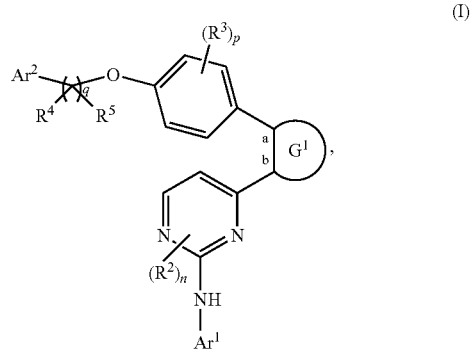

or a pharmaceutically acceptable salt, or a combination thereof, wherein

G$^1$ is formula (i), (ii), (iii), or (iv)

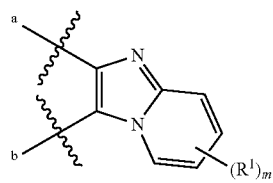

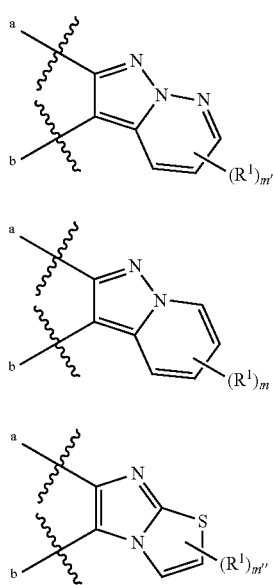

m is 0, 1, 2, 3, or 4;
m' is 0, 1, 2, or 3;
m" is 0, 1, or 2;
n is 0, 1, or 2;
p is 0, 1, 2, 3, or 4;
$R^1$, $R^2$, and $R^3$ are optional substituents, and if present, are each independently alkyl, halogen, —O(alkyl), —O(haloalkyl), or haloalkyl;
a and b designate the points of attachment at which formula (i), (ii), (iii), (iv) are bound to formula (I);
$R^4$ and $R^5$, at each occurrence, are each independently hydrogen, alkyl, halogen, or haloalkyl;
q is 1, 2, 3, or 4;
$Ar^1$ is aryl or heteroaryl; each of which is independently unsubstituted or substituted with 1, 2, 3, 4, or 5 substituents as represented by T, wherein each T is selected from the group consisting of oxo, alkyl, alkenyl, alkynyl, halogen, haloalkyl, CN, $NO_2$, $G^2$, —$OR^6$, —$OC(O)R^7$, —$SR^6$, —$S(O)R^7$, —$S(O)_2R^7$, —$S(O)_2N(R^8)(R^9)$, —$N(R^8)(R^9)$, —$N(R^8)C(O)R^7$, —$N(R^8)C(O)OR^7$, —$N(R^8)S(O)_2R^7$, —$N(R^8)C(O)N(R^8)(R^9)$, —$N(R^8)C(O)$—$(C_{1-6}$ alkylenyl)-$N(R^8)(R^9)$, —$N(R^8)S(O)_2N(R^8)(R^9)$, —$C(O)R^6$, —$C(O)OR^6$, —$C(O)N(R^8)(R^9)$, —$(C_{1-6}$ alkylenyl)-$G^2$, —$(C_{1-6}$ alkylenyl)-$OR^6$, —$(C_{1-6}$ alkylenyl)-$OC(O)R^7$, —$(C_{1-6}$ alkylenyl)-$SR^6$, —$(C_{1-6}$ alkylenyl)-$S(O)R^7$, —$(C_{1-6}$ alkylenyl)-$S(O)_2R^7$, —$(C_{1-6}$ alkylenyl)-$S(O)_2N(R^8)(R^9)$, —$(C_{1-6}$ alkylenyl)-$N(R^8)(R^9)$, —$(C_{1-6}$ alkylenyl)-$N(R^8)C(O)R^7$, —$(C_{1-6}$ alkylenyl)-$N(R^8)C(O)OR^7$, —$(C_{1-6}$ alkylenyl)-$N(R^8)S(O)_2R^7$, —$(C_{1-6}$ alkylenyl)-$N(R^8)C(O)N(R^8)(R^9)$, —$(C_{1-6}$ alkylenyl)-$N(R^8)S(O)_2N(R^8)(R^9)$, —$(C_{1-6}$ alkylenyl)-$C(O)R^6$, —$(C_{1-6}$ alkylenyl)-$C(O)OR^6$, and —$(C_{1-6}$ alkylenyl)-$C(O)N(R^8)(R^9)$,
two substituents on the vicinal carbon atoms of $Ar^1$, together with the carbon atoms to which they are attached, optionally form a monocyclic 5- or 6-membered heterocycle containing one or two heteroatoms selected from N(H), O, S, S(O), or $S(O)_2$, wherein each of the monocyclic ring is optionally substituted with 1, 2, 3, or 4 alkyl groups;

each occurrence of $R^6$ and $R^9$ are each independently hydrogen, alkyl, haloalkyl, —$(C_{1-6}$ alkylenyl)-CN, —$(C_{1-6}$ alkylenyl)-OH, —$(C_{1-6}$ alkylenyl)-C(O)OH, $G^3$, or —$(C_{1-6}$ alkylenyl)-$G^3$;
each occurrence of $R^7$ is independently alkyl, haloalkyl, —$(C_{1-6}$ alkylenyl)-CN, —$(C_{1-6}$ alkylenyl)-OH, $G^3$, or —$(C_{1-6}$ alkylenyl)-$G^3$;
each occurrence of $R^8$ is independently hydrogen, alkyl, or haloalkyl;
each occurrence of $G^2$ is independently aryl, heteroaryl, heterocycle, cycloalkyl, or cycloalkenyl, each of which is independently unsubstituted or substituted with 1, 2, 3, 4, or 5 substituents selected from the group consisting of $G^3$, —$(C_{1-6}$ alkylenyl)-$G^3$, and $R^{10}$,
each occurrence of $G^3$ is independently aryl, heteroaryl, heterocycle, cycloalkyl, or cycloalkenyl, each of which is independently unsubstituted or substituted with 1, 2, 3, 4, or 5 $R^{10}$ groups;
$Ar^2$ is aryl or heteroaryl, each of which is independently unsubstituted or substituted with 1, 2, 3, 4, or 5 $R^{10}$ groups;
each occurrence of $R^{10}$ is independently alkyl, alkenyl, alkynyl, halogen, haloalkyl, oxo, CN, $NO_2$, —$OR^{Z1}$, —$OC(O)R^{Z2}$, —$SR^{Z1}$, —$S(O)R^{Z2}$, —$S(O)_2R^{Z2}$, —$S(O)_2N(R^{Z3})(R^{Z4})$, —$N(R^{Z3})(R^{Z4})$, —$N(R^{Z3})C(O)R^{Z2}$, —$N(R^{Z3})C(O)OR^{Z2}$, —$N(R^{Z3})S(O)_2R^{Z2}$, —$N(R^{Z3})C(O)N(R^{Z3})(R^{Z4})$, —$N(R^{Z3})S(O)_2N(R^{Z3})(R^{Z4})$, —$C(O)R^{Z1}$, —$C(O)OR^{Z1}$, —$C(O)N(R^{Z3})(R^{Z4})$, —$(C_{1-6}$ alkylenyl)-$OR^{Z1}$, —$(C_{1-6}$ alkylenyl)-$OC(O)R^{Z2}$, —$(C_{1-6}$ alkylenyl)-$SR^{Z1}$, —$(C_{1-6}$ alkylenyl)-$S(O)R^{Z2}$, —$(C_{1-6}$ alkylenyl)-$S(O)_2R^{Z2}$, —$(C_{1-6}$ alkylenyl)-$S(O)_2N(R^{Z3})(R^{Z4})$, —$(C_{1-6}$ alkylenyl)-$N(R^{Z3})(R^{Z4})$, —$(C_{1-6}$ alkylenyl)-$N(R^{Z3})C(O)R^{Z2}$, —$(C_{1-6}$ alkylenyl)-$N(R^{Z3})C(O)OR^{Z2}$, —$(C_{1-6}$ alkylenyl)-$N(R^{Z3})S(O)_2R^{Z2}$, —$(C_{1-6}$ alkylenyl)-$N(R^{Z3})C(O)N(R^{Z3})(R^{Z4})$, —$(C_{1-6}$ alkylenyl)-$N(R^{Z3})S(O)_2N(R^{Z3})(R^{Z4})$, —$(C_{1-6}$ alkylenyl)-$C(O)R^{Z1}$, —$(C_{1-6}$ alkylenyl)-$C(O)OR^{Z1}$, or —$(C_{1-6}$ alkylenyl)-$C(O)N(R^{Z3})(R^{Z4})$,
each occurrence of $R^{Z1}$, $R^{Z3}$, and $R^{Z4}$, are each independently hydrogen, alkyl, or haloalkyl; and
each occurrence of $R^{Z2}$ is independently alkyl or haloalkyl.

2. The compound according to claim 1 having formula (I) or a pharmaceutically acceptable salt thereof, wherein $Ar^2$ is optionally substituted phenyl.

3. The compound according to claim 1 having formula (I-i) or a pharmaceutically acceptable salt thereof

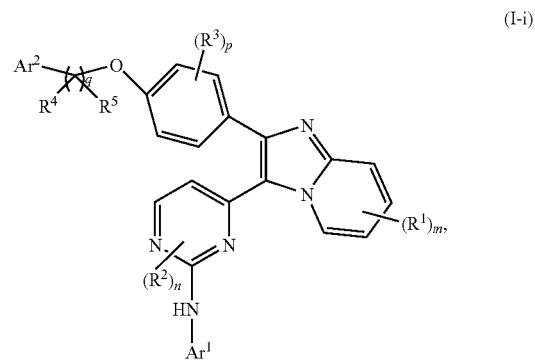

wherein $R^1$, $R^2$, $R^3$, $R^4$, $R^5$, m, n, p, q, $Ar^1$, and $Ar^2$ are as set forth in claim 1.

4. The compound according to claim 3 having formula (I-i), or a pharmaceutically acceptable salt thereof, wherein Ar² is optionally substituted phenyl.

5. The compound according to claim 3 having formula (I-i), or a pharmaceutically acceptable salt thereof, wherein Ar² and Ar¹ are optionally substituted phenyl.

6. The compound according to claim 3 having formula (I-i), or a pharmaceutically acceptable salt thereof, wherein Ar² is optionally substituted phenyl, and Ar¹ is optionally substituted heteroaryl.

7. The compound according to claim 1 having formula (I-ii) or a pharmaceutically acceptable salt thereof

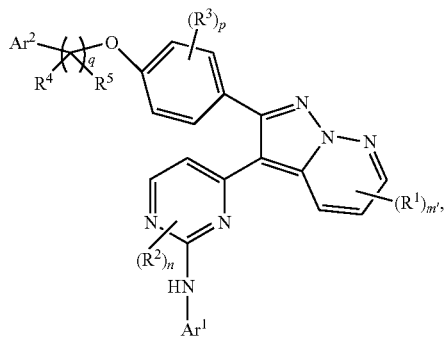

(I-ii)

wherein $R^1$, $R^2$, $R^3$, $R^4$, $R^5$, m', n, p, q, $Ar^1$, and $Ar^2$ are as set forth in claim 1.

8. The compound according to claim 7 having formula (I-ii), or a pharmaceutically acceptable salt thereof, wherein Ar² is optionally substituted phenyl.

9. The compound according to claim 7 having formula (I-ii), or a pharmaceutically acceptable salt thereof, wherein Ar² and Ar¹ are optionally substituted phenyl.

10. The compound according to claim 1 having formula (I-iii) or a pharmaceutically acceptable salt thereof

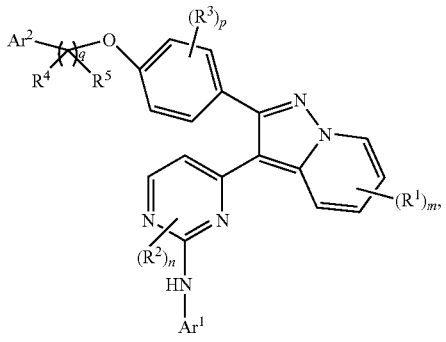

(I-iii)

wherein $R^1$, $R^2$, $R^3$, $R^4$, $R^5$, m, n, p, q, $Ar^1$, and $Ar^2$ are as set forth in claim 1.

11. The compound according to claim 10 having formula (I-iii), or a pharmaceutically acceptable salt thereof, wherein Ar² is optionally substituted phenyl.

12. The compound according to claim 10 having formula (I-iii), or a pharmaceutically acceptable salt thereof, wherein Ar² and Ar¹ are optionally substituted phenyl.

13. The compound according to claim 1 having formula (I-iv) or a pharmaceutically acceptable salt thereof

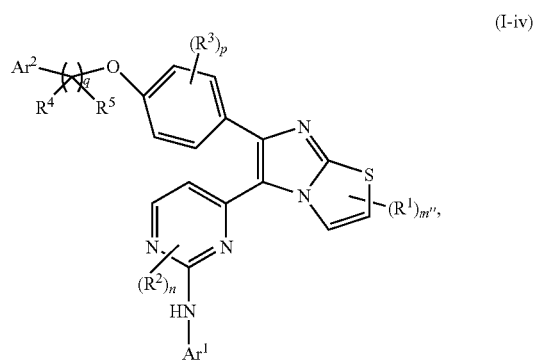

(I-iv)

wherein $R^1$, $R^2$, $R^3$, $R^4$, $R^5$, m'', n, p, q, $Ar^1$, and $Ar^2$ are as set forth in claim 1.

14. The compound according to claim 13 having formula (I-iv), or a pharmaceutically acceptable salt thereof, wherein Ar² is optionally substituted phenyl.

15. The compound according to claim 13 having formula (I-iv), or a pharmaceutically acceptable salt thereof, wherein Ar² and Ar¹ are optionally substituted phenyl.

16. The compound according to claim 1 or a pharmaceutically acceptable salt thereof, selected from the group consisting of 4-{2-[4-(benzyloxy)phenyl]imidazo[1,2-a]pyridin-3-yl}-N-{3-[2-(dimethylamino)ethyl]phenyl}pyrimidin-2-amine;

4-{2-[4-(benzyloxy)phenyl]imidazo[1,2-a]pyridin-3-yl}-N-(2-methoxy-4-morpholin-4-ylphenyl)pyrimidin-2-amine;

4-{2-[4-(benzyloxy)phenyl]imidazo[1,2-a]pyridin-3-yl}-N-(2-methoxyphenyl)pyrimidin-2-amine;

4-{2-[4-(benzyloxy)phenyl]imidazo[1,2-a]pyridin-3-yl}-N-[3-(methylsulfonyl)phenyl]pyrimidin-2-amine;

3-[(4-{2-[4-(benzyloxy)phenyl]imidazo[1,2-a]pyridin-3-yl}pyrimidin-2-yl)amino]-N,N-dimethylbenzenesulfonamide;

4-{2-[4-(benzyloxy)phenyl]imidazo[1,2-a]pyridin-3-yl}-N-[4-(methylsulfonyl)phenyl]pyrimidin-2-amine;

4-{2-[4-(benzyloxy)phenyl]imidazo[1,2-a]pyridin-3-yl}-N-phenylpyrimidin-2-amine;

4-{2-[4-(benzyloxy)-2-fluorophenyl]imidazo[1,2-a]pyridin-3-yl}-N-{3-[2-(dimethylamino)ethyl]phenyl}pyrimidin-2-amine;

4-{2-[4-(benzyloxy)-3-fluorophenyl]imidazo[1,2-a]pyridin-3-yl}-N-{3-[2-(dimethylamino)ethyl]phenyl}pyrimidin-2-amine;

4-{2-[4-(benzyloxy)-2-methylphenyl]imidazo[1,2-a]pyridin-3-yl}-N-{3-[2-(dimethylamino)ethyl]phenyl}pyrimidin-2-amine;

4-{2-[4-(benzyloxy)-3-chlorophenyl]imidazo[1,2-a]pyridin-3-yl}-N-{3-[2-(dimethylamino)ethyl]phenyl}pyrimidin-2-amine;

4-{2-[4-(benzyloxy)-3-methoxyphenyl]imidazo[1,2-a]pyridin-3-yl}-N-{3-[2-(dimethylamino)ethyl]phenyl}pyrimidin-2-amine;

4-{2-[4-(benzyloxy)phenyl]imidazo[1,2-a]pyridin-3-yl}-N-{2-methoxy-4-[4-(4-methylpiperazin-1-yl)piperidin-1-yl]phenyl}pyrimidin-2-amine;

4-{2-[4-(benzyloxy)phenyl]imidazo[1,2-a]pyridin-3-yl}-N-(5-methyl-1H-pyrazol-3-yl)pyrimidin-2-amine;

4-{2-[4-(benzyloxy)phenyl]imidazo[1,2-a]pyridin-3-yl}-N-(3-cyclopropyl-1H-pyrazol-5-yl)pyrimidin-2-amine;

N-{3-[2-(dimethylamino)ethyl]phenyl}-4-(2-{4-[(2-methoxybenzyl)oxy]phenyl}imidazo[1,2-a]pyridin-3-yl)pyrimidin-2-amine;

N-{3-[2-(dimethylamino)ethyl]phenyl}-4-(2-{4-[(4-methoxybenzyl)oxy]phenyl}imidazo[1,2-a]pyridin-3-yl)pyrimidin-2-amine;

N-{3-[2-(dimethylamino)ethyl]phenyl}-4-(2-{4-[(2-fluorobenzyl)oxy]phenyl}imidazo[1,2-a]pyridin-3-yl)pyrimidin-2-amine;

N-{3-[2-(dimethylamino)ethyl]phenyl}-4-(2-{4-[(3-fluorobenzyl)oxy]phenyl}imidazo[1,2-a]pyridin-3-yl)pyrimidin-2-amine;

N-{3-[2-(dimethylamino)ethyl]phenyl}-4-(2-{4-[(4-fluorobenzyl)oxy]phenyl}imidazo[1,2-a]pyridin-3-yl)pyrimidin-2-amine;

N-{3-[2-(dimethylamino)ethyl]phenyl}-4-{2-[4-(1-phenylethoxy)phenyl]imidazo[1,2-a]pyridin-3-yl}pyrimidin-2-amine;

4-{2-[4-(benzyloxy)phenyl]imidazo[1,2-a]pyridin-3-yl}-N-(4-chloro-2-methoxyphenyl)pyrimidin-2-amine;

4-{2-[4-(benzyloxy)-3-methoxyphenyl]imidazo[1,2-a]pyridin-3-yl}-N-[4-(2-pyrrolidin-1-ylethyl)phenyl]pyrimidin-2-amine;

4-{2-[4-(benzyloxy)-3-methoxyphenyl]imidazo[1,2-a]pyridin-3-yl}-N-[3-(2-pyrrolidin-1-ylethyl)phenyl]pyrimidin-2-amine;

4-{2-[4-(benzyloxy)-3-methoxyphenyl]imidazo[1,2-a]pyridin-3-yl}-N-(3-morpholin-4-ylphenyl)pyrimidin-2-amine;

4-{2-[4-(benzyloxy)phenyl]imidazo[1,2-a]pyridin-3-yl}-N-(1-methyl-1H-pyrazol-4-yl)pyrimidin-2-amine;

2-{4-[(4-{2-[4-(benzyloxy)phenyl]imidazo[1,2-a]pyridin-3-yl}pyrimidin-2-yl)amino]-1H-pyrazol-1-yl}ethanol;

4-{2-[4-(benzyloxy)phenyl]imidazo[1,2-a]pyridin-3-yl}-N-(4-fluorophenyl)pyrimidin-2-amine;

4-{2-[4-(benzyloxy)phenyl]imidazo[1,2-a]pyridin-3-yl}-N-(2,4-difluorophenyl)pyrimidin-2-amine;

4-{2-[4-(benzyloxy)-3-methoxyphenyl]imidazo[1,2-a]pyridin-3-yl}-N-[3-(2-pyrrolidin-1-ylethoxy)phenyl]pyrimidin-2-amine;

2-[{3-[(4-{2-[4-(benzyloxy)-3-methoxyphenyl]imidazo[1,2-a]pyridin-3-yl}pyrimidin-2-yl)amino]phenyl}(ethyl)amino]ethanol;

4-{2-[4-(benzyloxy)-3-methoxyphenyl]imidazo[1,2-a]pyridin-3-yl}-N-[4-(1,1-dioxidothiomorpholin-4-yl)phenyl]pyrimidin-2-amine;

4-{2-[4-(benzyloxy)-3-methoxyphenyl]imidazo[1,2-a]pyridin-3-yl}-N-{4-[4-(dimethylamino)piperidin-1-yl]-2-methoxyphenyl}pyrimidin-2-amine;

4-{2-[4-(benzyloxy)-3-methoxyphenyl]imidazo[1,2-a]pyridin-3-yl}-N-[2-methoxy-5-(methylsulfonyl)phenyl]pyrimidin-2-amine;

4-{2-[4-(benzyloxy)phenyl]imidazo[1,2-a]pyridin-3-yl}-N-[2-methoxy-5-(methylsulfonyl)phenyl]pyrimidin-2-amine;

4-{2-[4-(benzyloxy)-3-methoxyphenyl]imidazo[1,2-a]pyridin-3-yl}-N-{4-[4-(dimethylamino)piperidin-1-yl]phenyl}pyrimidin-2-amine;

4-{2-[4-(benzyloxy)-3-methoxyphenyl]imidazo[1,2-a]pyridin-3-yl}-N-[1-(2-pyrrolidin-1-ylethyl)-1H-pyrazol-4-yl]pyrimidin-2-amine;

2-[(2-{3-[(4-{2-[4-(benzyloxy)-3-methoxyphenyl]imidazo[1,2-a]pyridin-3-yl}pyrimidin-2-yl)amino]phenyl}ethyl)(methyl)amino]ethanol;

4-{2-[4-(benzyloxy)-3-methoxyphenyl]imidazo[1,2-a]pyridin-3-yl}-N-(2-methoxy-4-morpholin-4-ylphenyl)pyrimidin-2-amine;

4-{2-[4-(benzyloxy)-3-methoxyphenyl]imidazo[1,2-a]pyridin-3-yl}-N-[2-methoxy-5-(trifluoromethyl)phenyl]pyrimidin-2-amine;

4-{2-[4-(benzyloxy)phenyl]imidazo[1,2-a]pyridin-3-yl}-N-[2-methoxy-5-(trifluoromethyl)phenyl]pyrimidin-2-amine;

$N^1$-(4-{2-[4-(benzyloxy)-3-methoxyphenyl]imidazo[1,2-a]pyridin-3-yl}pyrimidin-2-yl)-2-methoxy-$N^4,N^4$-dimethylbenzene-1,4-diamine;

4-{2-[4-(benzyloxy)-3-methoxyphenyl]imidazo[1,2-a]pyridin-3-yl}-N-{1-[2-(dimethylamino)ethyl]-1H-pyrazol-4-yl}pyrimidin-2-amine;

2-(4-{4-[(4-{2-[4-(benzyloxy)-3-methoxyphenyl]imidazo[1,2-a]pyridin-3-yl}pyrimidin-2-yl)amino]phenyl}piperazin-1-yl)ethanol;

1-({4-[(4-{2-[4-(benzyloxy)-3-methoxyphenyl]imidazo[1,2-a]pyridin-3-yl}pyrimidin-2-yl)amino]-3-methoxyphenyl}amino)-2-methylpropan-2-ol;

$N^1$-(4-{2-[4-(benzyloxy)-3-methoxyphenyl]imidazo[1,2-a]pyridin-3-yl}pyrimidin-2-yl)-2-methoxybenzene-1,4-diamine;

2-{4-[(4-{2-[4-(benzyloxy)-3-methoxyphenyl]imidazo[1,2-a]pyridin-3-yl}pyrimidin-2-yl)amino]-1H-pyrazol-1-yl}ethanol;

2-[{4-[(4-{2-[4-(benzyloxy)-3-methoxyphenyl]imidazo[1,2-a]pyridin-3-yl}pyrimidin-2-yl)amino]-3-methoxyphenyl}(methyl)amino]ethanol;

4-{2-[4-(benzyloxy)-3-(trifluoromethyl)phenyl]imidazo[1,2-a]pyridin-3-yl}-N-{3-[2-(dimethylamino)ethyl]phenyl}pyrimidin-2-amine;

4-{2-[4-(benzyloxy)-3-ethylphenyl]imidazo[1,2-a]pyridin-3-yl}-N-{3-[2-(dimethylamino)ethyl]phenyl}pyrimidin-2-amine;

4-{2-[4-(benzyloxy)-3-methoxyphenyl]imidazo[1,2-a]pyridin-3-yl}-N-(2-methoxy-4-thiomorpholin-4-ylphenyl)pyrimidin-2-amine;

4-{2-[4-(benzyloxy)-3-methoxyphenyl]imidazo[1,2-a]pyridin-3-yl}-N-(2-methoxy-5-morpholin-4-ylphenyl)pyrimidin-2-amine;

N-{4-[(4-{2-[4-(benzyloxy)-3-methoxyphenyl]imidazo[1,2-a]pyridin-3-yl}pyrimidin-2-yl)amino]-3-methoxyphenyl}glycine;

4-{2-[4-(benzyloxy)-3-methoxyphenyl]imidazo[1,2-a]pyridin-3-yl}-N-[1-(2-piperidin-1-ylethyl)-1H-pyrazol-4-yl]pyrimidin-2-amine;

4-{2-[4-(benzyloxy)-3-methoxyphenyl]imidazo[1,2-a]pyridin-3-yl}-N-[1-(2-morpholin-4-ylethyl)-1H-pyrazol-4-yl]pyrimidin-2-amine;

4-{2-[4-(benzyloxy)-3-methoxyphenyl]imidazo[1,2-a]pyridin-3-yl}-N-[2-methoxy-4-(4-thiomorpholin-4-ylpiperidin-1-yl)phenyl]pyrimidin-2-amine;

4-{2-[4-(benzyloxy)-3-methoxyphenyl]imidazo[1,2-a]pyridin-3-yl}-N-(2-methoxy-4-piperidin-4-ylphenyl)pyrimidin-2-amine;

4-{2-[4-(benzyloxy)-3-(trifluoromethoxy)phenyl]imidazo[1,2-a]pyridin-3-yl}-N-[3-(2-pyrrolidin-1-ylethyl)phenyl]pyrimidin-2-amine;

4-{2-[4-(benzyloxy)-3-methoxyphenyl]imidazo[1,2-a]pyridin-3-yl}-N-{5-[2-(dimethylamino)ethyl]-2-methoxyphenyl}pyrimidin-2-amine;

N-(4-{2-[4-(benzyloxy)-3-methoxyphenyl]imidazo[1,2-a]pyridin-3-yl}pyrimidin-2-yl)-2-methyl-1,2,3,4-tetrahydroisoquinolin-7-amine;

N-(4-{2-[4-(benzyloxy)-3-methoxyphenyl]imidazo[1,2-a]pyridin-3-yl}pyrimidin-2-yl)-1,2,3,4-tetrahydroisoquinolin-6-amine;

N-(4-{2-[4-(benzyloxy)-3-methoxyphenyl]imidazo[1,2-a]pyridin-3-yl}pyrimidin-2-yl)-1,2,3,4-tetrahydroisoquinolin-7-amine;

4-{2-[4-(benzyloxy)-3-methoxyphenyl]imidazo[1,2-a]pyridin-3-yl}-N-[4-(1,1-dioxidothiomorpholin-4-yl)-2-methoxyphenyl]pyrimidin-2-amine;

2-[{3-[(4-{2-[4-(benzyloxy)-3-methoxyphenyl]imidazo[1,2-a]pyridin-3-yl}pyrimidin-2-yl)amino]-4-methoxybenzyl}(methyl)amino]ethanol;

$N^1$-{4-[(4-{2-[4-(benzyloxy)-3-methoxyphenyl]imidazo[1,2-a]pyridin-3-yl}pyrimidin-2-yl)amino]phenyl}-$N^2$,$N^2$-dimethylglycinamide;

$N^1$-{3-[(4-{2-[4-(benzyloxy)-3-methoxyphenyl]imidazo[1,2-a]pyridin-3-yl}pyrimidin-2-yl)amino]phenyl}-$N^2$,$N^2$-dimethylglycinamide;

$N^1$-{3-[(4-{2-[4-(benzyloxy)phenyl]imidazo[1,2-a]pyridin-3-yl}pyrimidin-2-yl)amino]phenyl}-$N^2$,$N^2$-dimethylglycinamide;

4-{2-[4-(benzyloxy)-3-methylphenyl]imidazo[1,2-a]pyridin-3-yl}-N-{3-[2-(dimethylamino)ethyl]phenyl}pyrimidin-2-amine;

4-{2-[4-(benzyloxy)-3-methoxyphenyl]imidazo[1,2-a]pyridin-3-yl}-N-{4-[2-(dimethylamino)ethyl]phenyl}pyrimidin-2-amine;

1-{3-[(4-{2-[4-(benzyloxy)-3-methoxyphenyl]imidazo[1,2-a]pyridin-3-yl}pyrimidin-2-yl)amino]benzyl}pyrrolidin-3-ol;

$N^1$-{3-[(4-{2-[4-(benzyloxy)-3-methoxyphenyl]imidazo[1,2-a]pyridin-3-yl}pyrimidin-2-yl)amino]-4-methoxyphenyl}-$N^2$,$N^2$-dimethylglycinamide;

$N^1$-{3-[(4-{2-[4-(benzyloxy)phenyl]imidazo[1,2-a]pyridin-3-yl}pyrimidin-2-yl)amino]-4-methoxyphenyl}-$N^2$,$N^2$-dimethylglycinamide;

4-{2-[4-(benzyloxy)-3-methoxyphenyl]imidazo[1,2-a]pyridin-3-yl}-N-(2-methoxy-5-thiomorpholin-4-ylphenyl)pyrimidin-2-amine;

4-{2-[4-(benzyloxy)-3-methoxyphenyl]imidazo[1,2-a]pyridin-3-yl}-N-[5-(1,1-dioxidothiomorpholin-4-yl)-2-methoxyphenyl]pyrimidin-2-amine;

4-{2-[4-(benzyloxy)phenyl]pyrazolo[1,5-a]pyridin-3-yl}-N-{3-[2-(dimethylamino)ethyl]phenyl}pyrimidin-2-amine;

4-{2-[4-(benzyloxy)phenyl]pyrazolo[1,5-b]pyridazin-3-yl}-N-{3-[2-(dimethylamino)ethyl]phenyl}pyrimidin-2-amine;

4-{2-[4-(benzyloxy)phenyl]-6-fluoropyrazolo[1,5-a]pyridin-3-yl}-N-{3-[2-(dimethylamino)ethyl]phenyl}pyrimidin-2-amine;

4-{6-[4-(benzyloxy)phenyl]imidazo[2,1-b][1,3]thiazol-5-yl}-N-phenylpyrimidin-2-amine;

4-{6-[4-(benzyloxy)phenyl]imidazo[2,1-b][1,3]thiazol-5-yl}-N-(2-methoxyphenyl)pyrimidin-2-amine;

4-{6-[4-(benzyloxy)phenyl]imidazo[2,1-b][1,3]thiazol-5-yl}-N-{4-[4-(dimethylamino)piperidin-1-yl]-2-methoxyphenyl}pyrimidin-2-amine;

$N^1$-(4-{6-[4-(benzyloxy)-3-methoxyphenyl]imidazo[2,1-b][1,3]thiazol-5-yl}pyrimidin-2-yl)-2-methoxy-$N^4$,$N^4$-dimethylbenzene-1,4-diamine 4-{6-[4-(benzyloxy)-3-methoxyphenyl]imidazo[2,1-b][1,3]thiazol-5-yl}-N-[2-(pyrrolidin-1-ylmethyl)phenyl]pyrimidin-2-amine;

4-{6-[4-(benzyloxy)-3-methoxyphenyl]imidazo[2,1-b][1,3]thiazol-5-yl}-N-{4-[dimethylamino)methyl]phenyl}pyrimidin-2-amine;

4-{6-[4-(benzyloxy)-3-methoxyphenyl]imidazo[2,1-b][1,3]thiazol-5-yl}-N-{4-[4-(dimethylamino)piperidin-1-yl]-2-methoxyphenyl}pyrimidin-2-amine; and 4-{6-[4-(benzyloxy)-3-methoxyphenyl]imidazo[2,1-b][1,3]thiazol-5-yl}-N-{3-[2-(dimethylamino)ethyl]phenyl}pyrimidin-2-amine.

17. A pharmaceutical composition comprising a compound of claim 1 or pharmaceutically acceptable salt thereof, and one or more pharmaceutically acceptable carrier.

18. A method of treating cancer in a mammal comprising administering thereto a therapeutically effective amount of a compound of claim 1 or pharmaceutically acceptable salt thereof, wherein the cancer is bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer or thyroid cancer.

* * * * *